US007517855B2

(12) United States Patent
Ternansky et al.

(10) Patent No.: US 7,517,855 B2
(45) Date of Patent: Apr. 14, 2009

(54) PEPTIDES WHICH INHIBIT ANGIOGENESIS, CELL MIGRATION, CELL INVASION AND CELL PROLIFERATION, COMPOSITIONS AND USES THEREOF

(75) Inventors: Robert J. Ternansky, San Diego, CA (US); Stephanie A. Hopkins, Poway, CA (US); Won Hyung Yoon, San Diego, CA (US); Amy L. Allan, Encinitas, CA (US); Patricia L. Gladstone, San Diego, CA (US); Sean M. O'Hare, San Diego, CA (US); Fernando Donate, San Diego, CA (US); Andrew Mazar, San Diego, CA (US); Graham Parry, San Diego, CA (US); Marian Plunkett, San Diego, CA (US)

(73) Assignee: Attenuon, LLC, San Diego, CA (US)

( * ) Notice: Subject to any disclaimer, the term of this patent is extended or adjusted under 35 U.S.C. 154(b) by 0 days.

(21) Appl. No.: 10/723,144

(22) Filed: Nov. 25, 2003

(65) Prior Publication Data

US 2004/0162239 A1 Aug. 19, 2004

Related U.S. Application Data

(60) Provisional application No. 60/475,539, filed on Jun. 2, 2003, provisional application No. 60/429,174, filed on Nov. 25, 2002.

(51) Int. Cl.
| A61K 38/00 | (2006.01) |
| A61K 38/14 | (2006.01) |
| C07K 5/00 | (2006.01) |
| C07K 7/00 | (2006.01) |
| C07K 16/00 | (2006.01) |
| C07K 17/00 | (2006.01) |
| C07K 9/00 | (2006.01) |

(52) U.S. Cl. ............... 514/12; 514/13; 514/14; 514/15; 514/16; 514/17; 514/18; 530/324; 530/325; 530/326; 530/327; 530/328; 530/329; 530/330; 530/331

(58) Field of Classification Search ........................ None
See application file for complete search history.

(56) References Cited

U.S. PATENT DOCUMENTS

| 3,845,770 | A | 11/1974 | Theeuwes et al. |
| 3,916,899 | A | 11/1975 | Theeuwes et al. |
| 4,440,788 | A * | 4/1984 | Terayama et al. ............ 514/616 |
| 4,683,202 | A | 7/1987 | Mullis |
| 4,765,539 | A | 8/1988 | Noakes et al. |
| 5,112,598 | A | 5/1992 | Biesalski |
| 5,284,831 | A | 2/1994 | Kahl et al. |
| 5,443,816 | A | 8/1995 | Zamura et al. |
| 5,556,611 | A | 9/1996 | Biesalski |
| 5,561,220 | A | 10/1996 | Dean |
| 5,567,408 | A | 10/1996 | Zamora |
| 5,618,513 | A | 4/1997 | Srinivasan |
| 5,627,286 | A | 5/1997 | Ramalingam et al. |
| 5,639,725 | A | 6/1997 | O'Reilly et al. |
| 5,698,155 | A | 12/1997 | Grosswald et al. |
| 5,950,619 | A | 9/1999 | van der Linden et al. |
| 5,954,047 | A | 9/1999 | Amer et al. |
| 5,970,974 | A | 10/1999 | Van Der Linden et al. |
| 5,994,309 | A | 11/1999 | Mazar et al. |
| 6,001,965 | A | 12/1999 | Livant |
| 6,140,068 | A * | 10/2000 | Livant .......................... 435/29 |
| 6,225,284 | B1 | 5/2001 | Albert et al. |
| 6,472,369 | B1 * | 10/2002 | Livant ............................ 514/9 |
| 6,576,440 | B2 * | 6/2003 | Livant .......................... 435/29 |
| 7,148,196 | B2 | 12/2006 | Livant |
| 2002/0151501 | A1 | 10/2002 | Bowers et al. |
| 2003/0083264 | A1 * | 5/2003 | Livant ......................... 514/17 |
| 2004/0162239 | A1 * | 8/2004 | Allan et al. .................. 514/12 |
| 2005/0020810 | A1 * | 1/2005 | Ternansky et al. .......... 530/324 |

FOREIGN PATENT DOCUMENTS

| EP | 0 051 682 A1 | | 5/1982 |
| WO | WO98/30538 | * | 7/1998 |
| WO | WO 02/057786 | | 7/2002 |
| WO | WO 2004/063213 A2 | | 7/2004 |

OTHER PUBLICATIONS

Greene et al. Protective Groups in Organic Synthesis, Third Edition. Chapter 6: Protection fo the Thiol Group. 1999. John Wiley and Sons, Inc. pp. 454-493.*
Adelman et al., "In Vitro Deletional Mutagenesis for Bacterial Production of the 20,000-Dalton Form of Human Pituitary Growth Hormone," DNA (1983), 2:183-193.
Alderman, "A Review of Cellulose Ethers in Hydrophilic Matrices for Oral Controlled-Release Dosage Forms," Int. J. Pharm. Tech. & Prod. Mfr. (1984), 5(3) 1-9.
Almquist et al., "Synthesis and Biological Activity of a Ketomethylene Analogue of a Tripeptide Inhibitor of Angiotensin Converting Enzyme," J. Med. Chem. (1980), 23:1392.
Baldari et al., "A Novel Leader Peptide Which Allows Efficient Secretion of a Fragment of Human Interleukin 1β in Saccharomyces cerevisiae," EMBO J. (1987), 6:229-234.
Bamba et al., "Release Mechanisms in Gelforming Sustained Release Preparations," Int. J. Pharm. (1979), 2:307-315.
Beaucage et al., "Deoxynucleoside Phosphoramidities—A New Class of Key Intermediates for Deoxypolynucleotide Synthesis," Tetrahedron Lett. (1981), 22:1859.
Benjamin et al., "Selective Ablation of Immature Blood Vessels in Established Human Tumors Follows Vascular Endothelial Growth Factor Withdrawal," J. Clin. Invest. (1999), 103:159-165.

(Continued)

Primary Examiner—Cecilia Tsang
Assistant Examiner—Marcela M Cordero Garcia
(74) Attorney, Agent, or Firm—Jones Day

(57) ABSTRACT

The present invention relates generally to peptides, which inhibit angiogenesis, cell migration, cell invasion and cell proliferation, methods of making peptides, which inhibit angiogenesis, cell migration, cell invasion and cell proliferation, pharmaceutical compositions of these peptides and methods of using these peptides and pharmaceutical compositions of these peptides to treat diseases associated with aberrant vascularization.

9 Claims, 5 Drawing Sheets

OTHER PUBLICATIONS

Figure 1:
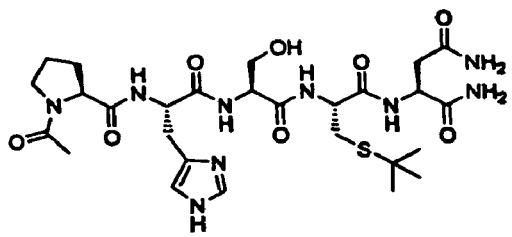
Figure 1:
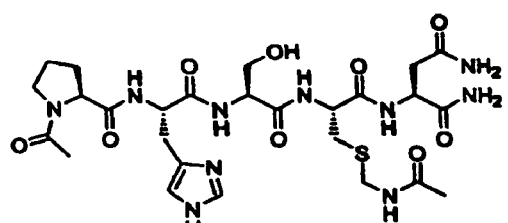
Figure 1:
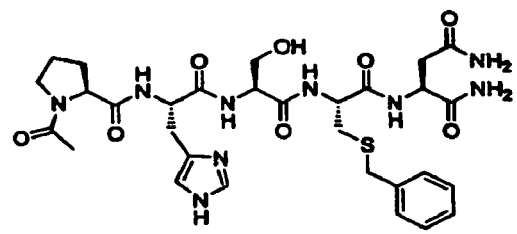
Figure 1:
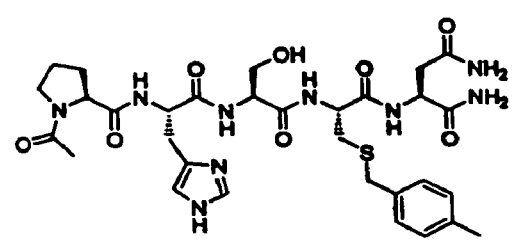
Figure 1:
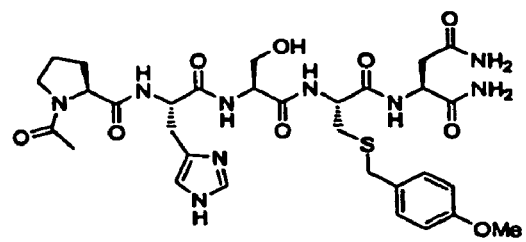
Figure 1:
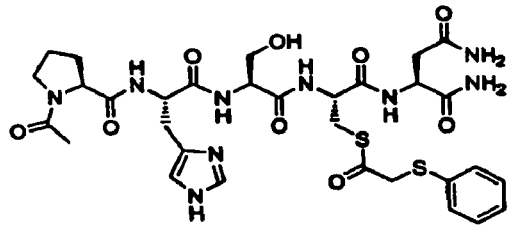

Blood et al., "Tumor Interactions with the Vasculature: Angiogenesis and Tumor Metastasis," *Biochim. Biophys. Acta* (1990), 1032:89-118.

Borgstrom et al., "Neutralizing Anti-Vascular Endothelial Growth Factor Antibody Completely Inhibits Angiogenesis and Growth of Human Prostate Carcinoma Micro Tumors In Vivo," *Prostate* (1998), 35:1-10.

Brooks et al., "Disruption of Angiogenesis by PEX, A Noncatalytic Metalloproteinase Fragment with Integrin Binding Activity," *Cell* (1998), 92:391-400.

Bruchez et al., "Semiconductor Nanocrystals as Fluorescent Biological Labels," *Science* (1998), 281:2013-2016.

Chambers et al., "Macrophage Colony-stimulating Factor Mediates Invasion of Ovarian Cancer Cells through Urokinase," *Canc. Res.* (1995), 55:1578-1585.

Chan et al, "Quantum Dot Bioconjugates for Ultrasensitive Nonisotopic Detection" *Science* (1998), 281:2016-2018.

Chorev et al., "Partially Modified Retro-Inverso-Enkephalinamides: Topochemical Long-Acting Analogs in vitro and in vivo," *Science* (1979), 204:1210-1212.

Crowley et al., "Prevention of Metastasis by Inhibition of the Urokinase Receptor," *Proc. Natl. Acad. Sci USA* (1993), 90:5021-5025.

During et al., "Controlled Release of dopamine from a Polymeric Brain Implant: In Vivo Characterization," *Ann. Neurol.* (1989) 25:351.

Edge, "Total Synthesis of a Human Leukocyte Interferon Gene," *Nature* (1981), 292:756-762.

Folkman, "Anti-Angiogenesis: New Concept for Therapy of Solid Tumors," *Ann. Surg.* (1972), 175:409-416.

Folkman, "The Influence of Angiogenesis Research on Management of Patients with Breast Cancer," *Breast Cancer Res. Treat.* (1995), 36(2):109-118.

Folkman, "Angiogenesis Inhibitors Generated by Tumors," *Mol. Med.* (1995), 1(2):120-122.

Giannis et al., "Peptidomimetics in Drug Design," *Adv. In Drug Res.* (1997), 29:1-78.

Gluzman, "SV40-Transformed Simian Cells Support the Replication of Early SV40 Mutants," *Cell* (1981), 23:175-182.

Goodson, "Medical Application of Controlled Release" 2:115-138 (1984).

Gorelik et al., "Control of Lung Metastasis Progression in Mice: Role of Growth Kinetics of 3LL Lewis Lung Carcinoma and Host Immune Reactivity," *J. Nat'l Canc. Inst.*, (1980), 65:1257-1264.

Gorelik et al., "Host's Immune State and Kinetics of Local Tumor Growth Control —Progression of Postoperative Lung Metastasis" *Rec. Results Canc. Res.* (1980), 75:20-28.

Hanahan et al., "Patterns and Emerging Mechanisms of the Angiogenic Switch during Tumorigenesis," *Cell* (1996), 86(3):353-364.

Hilgard et al., "Oral Anticoagulation in the Treatment of a Spontaneously Metastasising Murine Tumour (3LL)," *Br. J. Cancer* (1977), 35:78-86.

Holladay et al., "Synthesis of Hydroxyethlene and Ketomethylene Dipeptide Isosteres," *Tetrahedron Lett.* (1983), 24:4401-4404.

Howard et al., "Intracerebral drug delivery in rats with lesion-induced memory deficits," *J. Neurosurg.* (1989), 71:105-112.

Hruby, "Conformational Restrictions of Biologically Active Peptides Via Amino Acid Side Chain Groups," *Life Sci.* (1982), 4:189-199.

Hruby, "Conformational and Topographical Considerations in the Design of Biologically Active Peptides," *Biopolymers* (1993), 33:1073-1082.

Isakov et al., "An Immune Resonse against the Alloantigens of the 3LL Lewis Lung Carcinoma Prevents the Growth of Lung Metastases, but Not of Local Allografts," *Invasion Matas.* (1982) 2:12-32.

Jay, "Chemical Synthesis of a Biologically Active Gene for Human Immune Interferon-γ," *J. Biol. Chem* (1984), 259:6311-6317.

Jenning-White et al., "Synthesis of Ketomethylene Analogs of Dipeptides," *Tetrahedron Lett.* (1982), 23:2533-2534.

Kaufman et al., "Translational Efficiency of Polycistronic mRNAs and their Utilization to Express Heterologous Genes in Mammalian cells," *EMBO J.*, (1987), 6:187-195.

Kleinman et al., "Basement Membrane Complexes with Biological Activity," *Biochemistry* (1986), 25:312-318.

Kurjan et al., "Structure of a Yeast Pheromone Gene (MFα): A Putative α-Factor Precursor Contains Four Tandem Copies of Mature α-Factor," *Cell*, (1982), 30:933-943.

Langer et al., "Chemical and Physical Structure of Polymers as Carriers for Controlled Release of Bioactive Agents: A Review," *J. Macromol. Sci. Rev. Macromol Chem.*, (1983), 23:61.

Langer, "New Methods of Drug Delivery," *Science*, (1990), 249:1527-1533.

Levy et al., "Inhibition of Calcification of Bioprosthetic Heart Valves by Local Controlled-Release Diphosphonate," *Science*, (1985) 228:190.

Lucklow et al., "High Level Expression of Nonfused Foreign Genes with *Autographa californica* Nuclear Polyhedrosis Virus Expression Vectors," Virology (1989), 170:31-39.

Malave et al., "Influence of Inoculation Site on Development of the Lewis Lung Carcinoma and Suppressor Cell Activity in Syngeneic Mice," *J. Nat'l. Canc. Inst.* (1979), 62:83-88.

Matteucci et al., "Synthesis of Deoxyoligonucleotides on a Polymer Support," *J. Am. Chem Soc.* (1981), 103:3185.

Maxam et al., "Nucleic Acids," *Meth. Enzymol.* (1980), 65:499-560.

Merrifield, Solid Phase Peptide Synthesis. I. "The Synthesis of a Tetrapeptide," *J. Amer. Chem. Soc.* (1963), 85:2149-54.

Messing et al., "A System for Shotgun DNA Sequencing," *Nucleic Acids Res.* (1981), 9:309.

Millauer et al., "Dominant-Negative Inhibition of FIk-1 Suppress the Growth of Many Tumor Types in Vivo," Cancer Res. (1996), 56:1615-1620.

Min et al., "Urokinase Receptor Antagonists Inhibit Angiogenesis and Primary Tumor Growth in Syngeneic Mice," *Cancer Res.* (1996), 56:2428-2433.

Moore et al., "Design and Pharmacology of Peptide Mimetics," *Adv. In Pharmacol.* (1995), 33:91-141.

Nambair et al., "Total Synthesis and Cloning of a Gene Coding for the Ribonuclease S Protein," *Science* (1984), 223:1299-1301.

Nguyen et al., "Quantitation of Angiogenesis and Antiangiogenesis in the Chick Embryo Chorioallantoic Membrane," *Microvascular Res.* (1994), 47:31-40.

Odedra et al., "Low Molecular Weight Angiogenesis Factors," *Pharmac. Ther.* (1991), 49:111-124.

Olson et al., "Concepts and Progress in the Development of Peptide Mimetics," *J. Med. Chem.* (1993), 36:3039.

O'Reilly et al., "Endostatin: An Endogenous Inhibitor of Angiogensis and Tumor Growth," *Cell* (1997), 88:277-285.

O'Reilly et al., "Angiostatin: A Novel Angiogenesis Inhibitor That Mediates the Suppression of Metastases by a Lewis Lung Carcinoma," *Cell* (1994), 79:315-328.

Parish et al., (1992), "A Basement-Membrane Permeability Assay Which Correlates With The Metastatic Potential of Tumour Cells," *Int. J. Cancer* 52:378-383.

Passaniti et al., "A Simple, Quantitative Method for Assessing Angiogenesis and Antiangiogenic Agents Using Reconstructed Basement Membrane, Heparin, and Fibroblast Growth Factor," *Lab Invest.* (1992), 67:519-528.

Rabbani et al., "Prevention of Prostate-Cancer Metastasis *In Vivo* by a Novel Synthetic Inhibitor of Urokinase-Type Plasminogen Activator (uPA)" *Int. J. Cancer* (1995), 63:840-845.

Sanger, "DNA sequencing with chain-terminating inhibitors," *Proc. Natl. Acad. Sci. USA* (1977), 74:5463-5467.

Saudek et al., "A Premiminary Trial of the Programmable Implantable Medication System for Insulin Delivery," *N. Engl. J. Med.* (1989), 321:574.

Schnaper et al., "Plasminogen Activators Augment Endothelial Cell Organization In Vitro by Two Distinct Pathways," *J. Cell. Physiol.* (1995), 165:107-118.

Schockley et al., "Penetration of Tumor Tissue by Antibodies and Other Immunoproteins," *Ann. N.Y. Acad. Sci.* (1991), 617:367-382.

Schultz et al., "Expression and secretion in yeast of a 400-kDa envelope glycoprotein derived from Epstein—Barr virus," *Gene*, (1987),54:113-123.

Sefton, "Implantable Pumps," *CRC Crit. Ref. Biomed. Eng*, (1987), 14:201.

Smith et al., "Production of Human Beta Interferon in Insect Cells Infected with a Baculovirus Expression Vector," *Mol. Cell Biol.* (1983), 3:2156-2165.

Spatola, "Chemistry and Biochemistry of Amino Acids, Peptides and Proteins," B. Weinstein, (eds.), *Marcel Dekker*, New York, (1983) 267-357.

Spatola et al., "Structure-Activity Relationships of Enkephalins Containing Serially Replaced Thiomethylene Amide Bond Surrogates," *Life Sci.* (1986), 38:1243-1249.

Talmadge et al., "Enhanced Metastatic Potential of Tumor Cells Harvested From Spontaneous Metastases of Heterogeneous Murine Tumors," *J. Nat'l. Canc. Inst.* (1982), 69:975-980.

Thakur et al., "Indium-111-labeled leukocytes for the localization of abscess: preparation, analysis, tissue distribution, and comparison with gallium-67 citrate in dogs," *J. Lab. Clin. Med.* (1977), 89:217-228.

Treat et al., "Liposomes in the Therapy of Infectious Diseases and Cancer", *Lopez-Berestein and Fidler* (eds.), *Liss*, New York, pp. 353-365 (1989).

Verma et al., "Osmotically Controlled Oral Drug Delivery," *Drug Dev. Ind. Pharm.* (2000), 26:695-708.

Verschoyle et al., "Pharmacokinetics of Insotretinoin (ISO) in Rats following Oral Dosing or Aerosol Inhalation," *British J. Cancer* (1999), 80 Suppl. 2, 96.

Volpert et al., "Captopril Inhibits Angiogenesis and Slows the Growth of Experimental Tumors in Rats," *J. Clin. Invest.* (1996), 98:671-679.

Wiley et al., "Peptidomimetics Derived from Natural Products," *Med Res. Rev.* (1993), 13:327-384.

Xing et al., "Overexpression of Urokinase Receptor in Breast Cancer Cells Results In Increased Tumor Invasion, Growth and Metastasis," *Int. J. Cancer* (1996), 67:423-429.

Zoller et al., "Olignucleotide-directed mutagenesis using M13-derived vectors: an efficient and general procedure for the production of point mutations in any fragment of DNA," *Nucleic Acids Res.* (1982), 10:6487-6500.

Aboagye et al., "Use of positron emission tomography in anticancer drug development," Invest. New Drugs 2003, 21(2):169-181.

Akiyama et al., "Fibronectin and integrins in invasion and metastasis," Cancer Metastasis Rev. 1995, 14(3):173-189.

Bokel, "Integrins in development: moving on, responding to, and sticking to the extracellular matrix," Dev. Cell, 2002, 3(3):311-321.

Bornstein et al., "Matricellular proteins: extracellular modulators of cell function," Curr. Opin. Cell Biol. 2002, 14(5):608-616.

Cooper et al., "the role of alpha(v)beta(3) in prostate cancer progression," Neoplasia 2002, 4(3): 191-194.

Damiano, "Integrins as novel drug targets for overcoming innate drug resistance," Curr. Cancer Drug Targets 2002, 2(1):37-43.

Felding-Habermann, "Integrin adhesion receptors in tumor metastasis," Clin. Exp. Metastasis 2003, 20(3):203-213.

Felding-Habermann, "Integrin activation controls metastasis in human breast cancer," Proc. Natl. Acad. Sci. USA 2001, 98(4):1853-1858.

Geiger et al., "Transmembrane crosstalk between the extracellular matrix--cytoskeleton crosstalk," Nat. Rev. Mol. Cell Biol. 2001, 2(11):793-805.

Glaser et al., "Applications of positron-emitting halogens in PET oncology,"Int. J. Oncol. 2003, 22(2):253-267.

Herschman, "Molecular Imaging: Looking at Problems, Seeing Solutions," Science 2003, 302(5645): 605-608.

Hood et al., "Role of integrins in cell invasion and migration," Nat. Rev. Cancer 2002, 2(2): 91-100.

Kemperman et al., "The role of integrins and integrin activation in liver metastasis," Invasion Metastasis 1994-95, 14(1-6):98-108.

Kerr et al., "The alpha v integrin antagonists as novle anticancer agents: and update," Expert Opin. Investig. Drugs 2002, 11(12):1765-1774.

Kim et al., "Regulation of Angiogenesis in Vivo by Ligation of Integrin 5β1 with the Central Cell-Binding Domain of Fibronectin," Am. J. Pathol. 2000, 156(4):1345-1362.

Kumar, "Integrin alpha v beta 3 as a therapeutic target for blocking tumor-induced angiogenesis," Curr. Drug. Targets 2003, 4(2):123-131.

LaBat-Robert, "Fibronectin in Malignancy," Semin. Cancer Biol. 2002, 12(3):187-195.

Li et al., "Synthesis of polyethylene glycol (PEG) derivatives and PEGylated-peptide biopolymer conjugates," Biomacromolecules 2003, 4:1055-1067.

Liu et al., "Antiangiogenic therapy," Semin. Oncol. 2002, 29(3 Suppl. 11): 96-103.

Livant et al. "Anti-invasive, Antitumorigenic, and Antimetastatic Activities of the PHSCN Sequence in Prostate Carcinoma," Cancer Res. 2000, 60(2): 309-320.

Lohr et al., "Expression and function of receptors for extracellular matrix proteins in human ductal adenocarcinomas of the pancreas," Pancreas 1996, 12(3):248-259.

Merajver et al., "Copper Depletion as and Anti-Angiogenic Strategy in HER2-neu Transgenic," Proceedings of Special AACR Conference on Angiogenesis and Cancer 1998, Abstract #B-11, Jan. 22-24.

Metzner et al., "Evidence of the involvement of phosphatidylinositol 3-kinase in the migration, actin stress fiber formation, and alpha v beta 3-integrin-mediated adherence of human melanoma cells," J. Invest. Dermatol. 1996, 107(4): 597-602.

Nip et al., "The role of the integrin vitronectin receptor, alpha v beta 3 in melanoma metastasis," Cancer Metastasis Rev. 1995, 14(3): 241-252.

O'Brien et al., "Expression of the integrin alpha 5 subunit in HT29 colon carcinoma cells suppresses apoptosis triggered by serum deprivation," Exp. Cell Res. 1996, 224(1):208-213.

Pecheur et al., " Integrin alpha v beta 3 expression conferson tumor cells a greater propensity to metastasize to bone," FASEB J. 2002, 16(10): 1266-1268.

Platten et al., "Transforming growth factors beta(1) (TGF-beta(1)) and TGF-beta(2) promote glioma cell migration via Up-regulation of alpha(V)beta(3) integrin expression," Biochem. Biophys. Commun. 2000, 268(2): 607-611.

Rabb et al., "Alpha-V/beta-3 and alpha-V/beta-5 integrin distribution in neoplastic kidney," Am. J. Nephrol. 1996, 16(5):402-408.

Raleigh et al., "Pharmacokinetics of Isotrentinoin (ISO) in Rats Following Oral Dosing or Aerosol Inhalation," British J. Cancer, 1990, 80, Suppl. 2, 96.

Ruoslahti, "Fibronectin and its alpha 5 beta 1 integrin receptor in malignancy," Invasion Metastasis 1994; 14(1-6): 87-97.

Rust et al., "The Promise of Integrins as Effective Targets for Anticancer Agents," J.Biomed. Biotechnol. 2002, 2(3): 124-130.

Stoeltzing et al., "Inhibition of integrin alpha5beta 1 function with a small peptide (ATN-161) plus continuous 5-FU infusion reduces colorectal liver metastases and improves survival in mice," Int. J. Cancer 2003, 104(4):496-503.

Stupack et al., "Get a ligand, get a life: integrins, signaling and cell survival," J. Cell Sci. 2002, 115: 3729-38.

Tani et al., "Expression level of integrin alpha 5 on tumor cells affects the rate of metastasis to the kidney," Br, J. Cancer 2003, 88(2): 327-333.

Tucker, "Inhibitors of integrins," Curr. Opin. Pharmacol. 2002, 2(4): 394-402.

Van De Wiele et al., "Tumour angiogenesis pathways: related clinical issues and implications for nuclear medicine imaging," Eur. J. Nucl. Med. Mol. Imaging 2002, 29(5): 699-709.

Varner et al., "Tumor angiogenesis and the role of vascular cell integrin alphavbeta3," Import. Adv. Oncol. 1996, 69-87.

Livant et al., 2000, "Anti-Invasive, Antitumorigenic, and Antimetastatic Activities of the PHSCN sequence in Prostate Carcinoma," Cancer Res. 60(2): 309-320.

Supplemental Partial European Search Report issued Dec. 12, 2007 in connection with European Application No. EP 03812058.0.

Office Action mailed on Aug. 11, 2005 for U.S. Appl. No. 10/722,843 filed on Nov. 25, 2003.

Office Action mailed on Nov. 1, 2006 for U.S. Appl. No. 10/722,843 filed on Nov. 25, 2003.

Office Action mailed on Jun. 13, 2007 for U.S. Appl. No. 10/722,843 filed on Nov. 25, 2003.

* cited by examiner 1 (SEQ ID NO: 12)

2 (SEQ ID NO: 46)

3 (SEQ ID NO: 3)

4 (SEQ ID NO: 4)

5 (SEQ ID NO: 9)

6 (SEQ ID NO: 20)

7 (SEQ ID NO: 11)

8 (SEQ ID NO: 5)

9 (SEQ ID NO: 6)

10 (SEQ ID NO: 40)

11 (SEQ ID NO: 28)

12 (SEQ ID NO: 29)

13 (SEQ ID NO: 22)

14 (SEQ ID NO: 23)

15 (SEQ ID NO: 18)

16 (SEQ ID NO: 21)

17 (SEQ ID NO: 24)

18 (SEQ ID NO: 25)

30 (SEQ ID NO: 34)

31 (SEQ ID NO: 33)

32 (SEQ ID NO: 36)

33 (SEQ ID NO: 48)

34 (SEQ ID NO: 49)

35 (SEQ ID NO: 50)

PEPTIDES WHICH INHIBIT ANGIOGENESIS, CELL MIGRATION, CELL INVASION AND CELL PROLIFERATION, COMPOSITIONS AND USES THEREOF

This application claims the benefit under 35 U.S.C. § 119 (e) from U.S. Provisional Application Ser. No. 60/429,174, filed Nov. 25, 2002 and U.S. Provisional Application Ser. No. 60/475,539, filed Jun. 2, 2003 which are herein incorporated by reference in their entirety.

1. FIELD

The present invention relates generally to peptides, which inhibit angiogenesis, cell migration, cell invasion and cell proliferation, methods of making peptides, which inhibit angiogenesis, cell migration, cell invasion and cell proliferation, pharmaceutical compositions of these peptides and methods of using these peptides and pharmaceutical compositions thereof to treat diseases associated with aberrant vascularization.

2. BACKGROUND

Most forms of cancer are derived from solid tumors (Shockley et al., *Ann. N.Y. Acad. Sci.* 1991, 617: 367–382), which have proven resistant in the clinic to therapies such as the use of monoclonal antibodies and immunotoxins. Anti-angiogenic therapy for the treatment of cancer developed from the recognition that solid tumors require angiogenesis (i.e., new blood vessel formation) for sustained growth (Folkman, *Ann. Surg.* 1972, 175: 409–416; Folkman, *Mol. Med.* 1995, 1(2): 120–122; Folkman, *Breast Cancer Res. Treat.* 1995, 36(2): 109–118; Hanahan et al., *Cell* 1996, 86(3): 353–364). Efficacy of anti-angiogenic therapy in animal models has been demonstrated (Millauer et al., *Cancer Res.* 1996, 56:1615–1620; Borgstrom et al., *Prostrate* 1998, 35:1–10; Benjamin et al., *J. Clin. Invest.* 1999, 103: 159–165; Merajver et al., *Proceedings of Special AACR Conference on Angiogenesis and Cancer* 1998, Abstract #B-11, January 22–24) in the art. In the absence of angiogenesis, internal cell layers of solid tumors are inadequately nourished. Further, angiogenesis (i.e., aberrant vascularization) has now also been shown to be required for the growth of non-solid, hematological tumors and has been implicated in numerous other diseases (e.g., ocular neovascular disease, macular degeneration, rheumatoid arthritis, etc.).

Contrastingly, normal tissue does not require angiogenesis except under specialized circumstances (e.g., wound repair, proliferation of the internal lining of the uterus during the menstrual cycle, etc.). Accordingly, a requirement for angiogenesis is a significant difference between tumor cells and normal tissue. Importantly, the dependency of tumor cells on angiogenesis, when compared to normal cells, is quantitatively greater than differences in cell replication and cell death between normal tissue and tumor tissue, which are often exploited in cancer therapy.

Tumor angiogenesis can be initiated by cytokines such as vascular endothelial growth factor and/or fibroblast growth factor, which bind to specific receptors on endothelial cells in the local vasculature under hypoxic conditions. The activated endothelial cells secrete enzymes which remodel the associated tissue matrix and modulate expression of adhesion molecules such as integrins. Following matrix degradation, endothelial cells proliferate and migrate toward the tumor, which results in the generation and maturation of new blood vessels.

Interestingly, protein fragments, such as endostatin, kringle 5 and PEX, which inhibit angiogenesis, are produced by degradation of matrix proteins (O'Reilly et al., *Cell* 1997, 88:277–285; O'Reilly et al., *Cell,* 994, 79:315–328; Brooks et al., *Cell,* 1998, 92:391–400). Accordingly, these protein fragments may inhibit new angiogenesis, thus preventing tumor growth and metastasis.

However, protein fragments have significant drawbacks associated with their use (i.e., are difficult and expensive to produce in large quantities, poor pharmacological properties, susceptible to degradation, etc.). One approach has been to identify small peptide fragments of these larger proteins, which still retain a significant portion of the anti-angiogenic activity of the parent protein.

Although the search for peptides that inhibit angiogenesis has provided compounds with significant effectiveness in preventing growth of new blood vessels, molecules with superior activity profiles are still needed. Accordingly, novel peptides are needed to fully explore the potential of peptides in preventing angiogenesis. The novel peptides may have longer plasma half-lives, more resistance to degradation, increased bio-availability, higher affinity, greater selectivity, etc. in comparison to peptides described in the art (Livant, U.S. Pat. No. 6,001,965; Livant, U.S. Pat. No. 6,472,369). Such novel peptides may be effective in treating various diseases associated with angiogenesis such as cell migration, cell invasion and cell proliferation.

3. SUMMARY

The present invention satisfies these and other needs by providing peptides which inhibit angiogenesis, cell migration, cell invasion and cell proliferation, methods of making these peptides, pharmaceutical compositions of these peptides and methods of using these peptides and pharmaceutical compositions of these peptides to treat diseases associated with aberrant vascularization.

In a first aspect the present invention provides a compound of structural

Formula (I):

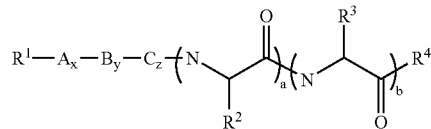

or a pharmaceutically available salt, solvate, hydrate or N-oxide thereof wherein:

a, b, x, y and z are 0 or 1;
A is a cyclic amino acid;
B is a basic amino acid;
C is a small amino acid;
$R^1$ is alkyl, substituted alkyl, acyl, substituted acyl, alkylsulfonyl, substituted alkylsulfonyl, arylalkyl, substituted arylalkyl, arylsulfonyl, substituted arylsulfonyl, heteroalkyl, substituted heteroalkyl, heteroarylsulfonyl, substituted heteroarylsulfonyl, heteroarylalkyl, substituted heteroarylalkyl, oxycarbonyl or substituted oxycarbonyl;
$R^2$ is alkyl, $-(CH_2)_mS(O)_nR^5$, $-(CH_2)_mS(O)_n-S(O)_oR^5$ or $-(CMe)_mS(O)_nR^5$
m is 1, 2, 3 or 4;
n and o are independently 0, 1 or 2;
$R^3$ is $-CH_2CONH_2$ or $-CH_2CH_2CONH_2$;
$R^4$ is alkyl, $-NR^6R^7$ or $-OR^8$;

$R^5$ is alkyl, substituted alkyl, acyl, substituted acyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, oxycarbonyl or substituted oxycarbonyl;

$R^6$ and $R^7$ are independently hydrogen or alkyl; and $R^8$ is alkyl, substituted alkyl, aryl substituted aryl, arylalkyl, substituted arylalkyl, heteroalkyl, substituted heteroalkyl, heteroaryl, substituted heteroaryl, heteroarylalkyl or substituted heteroarylalkyl;

with the provisos that:

$R^5$ is not methyl when m is 1;

a is 1 unless A is proline, B is histidine, C is serine and b is 0 when a is 0; and $R^2$ is —$(CH2)_mS(O)_nR^5$ or —$(CH_2)_mS(O)_n$—$S(O)_oR^5$ unless b, x, y and z are 1.

In a second aspect, the present invention pharmaceutical compositions of compounds are provided. The pharmaceutical compositions generally comprise one or more compounds or pharmaceutically acceptable salts, hydrates, solvates or N-oxides thereof and a pharmaceutically acceptable vehicle. The choice of vehicle will depend upon, among other factors, the desired mode of administration.

In a third aspect, the present invention provides methods for treating or preventing diseases or disorders characterized by aberrant vascularization. The methods generally involve administering to a patient in need of such treatment or prevention a therapeutically effective amount of a compound and/or pharmaceutical composition thereof.

4. BRIEF DESCRIPTION OF THE DRAWINGS

Figure 2:
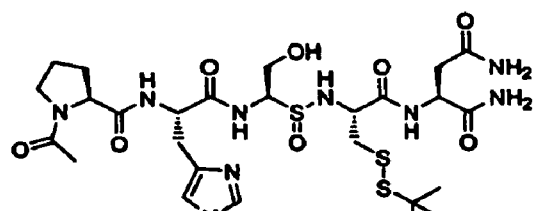
Figure 2:
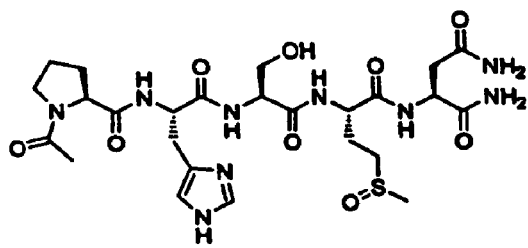
Figure 2:
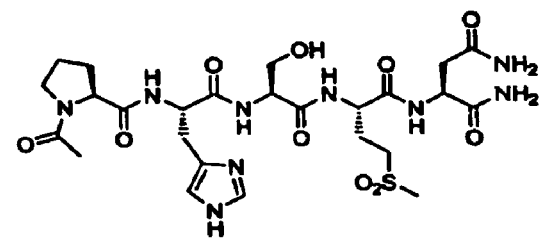
Figure 2:
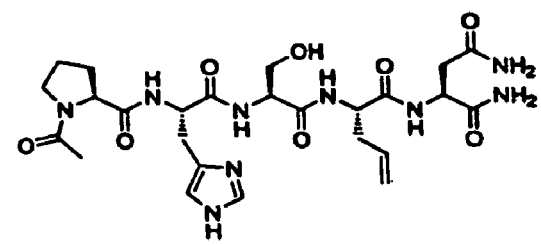
Figure 2:
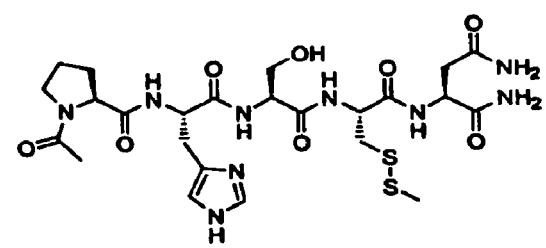
Figure 2:
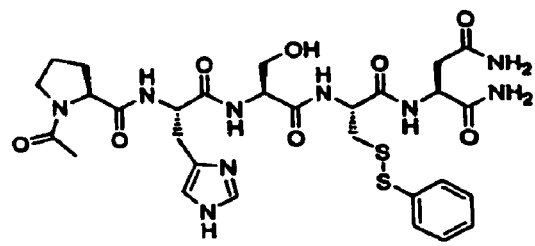
Figure 3:
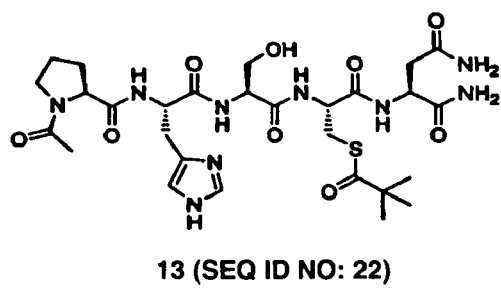
Figure 3:
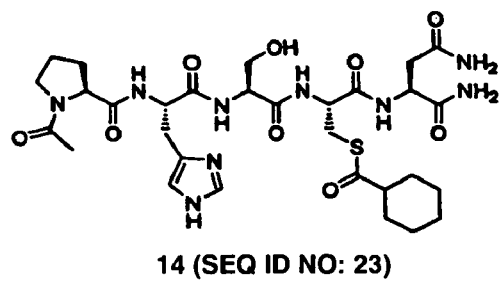
Figure 3:
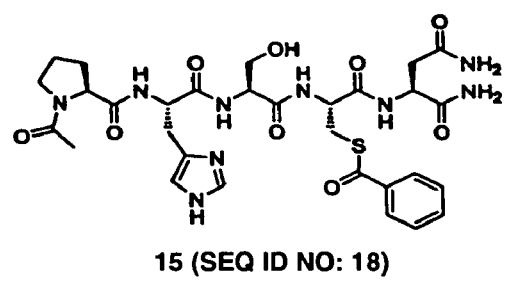
Figure 3:
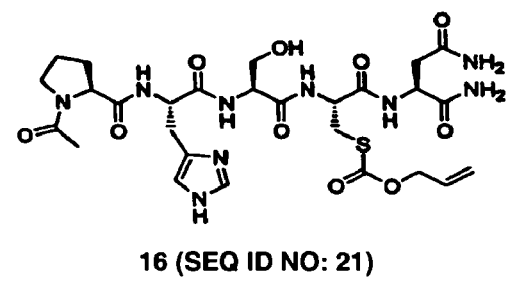
Figure 3:
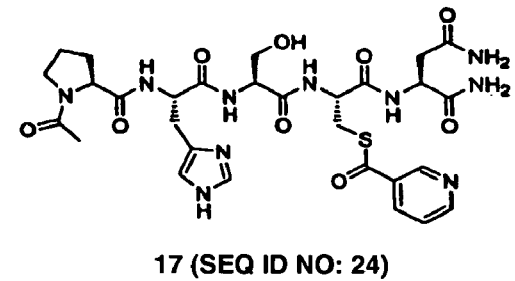
Figure 3:
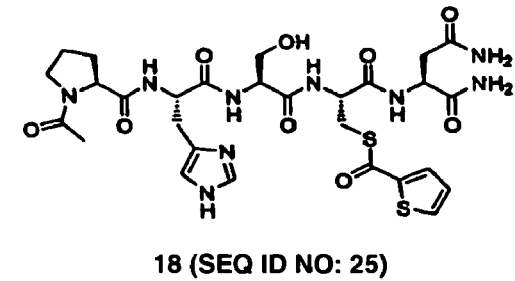
Figure 4:
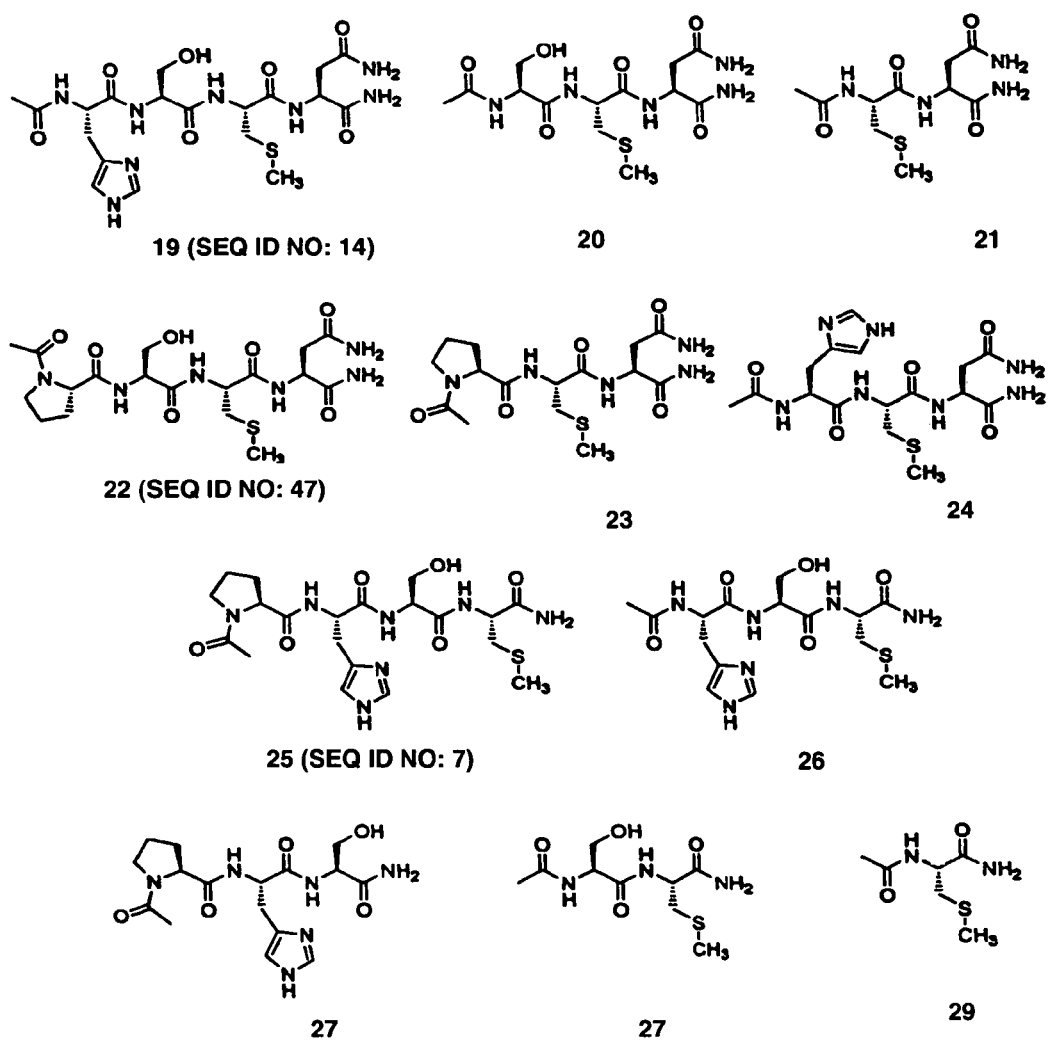
Figure 5:
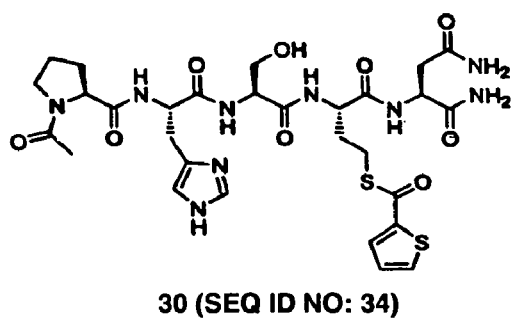
Figure 5:
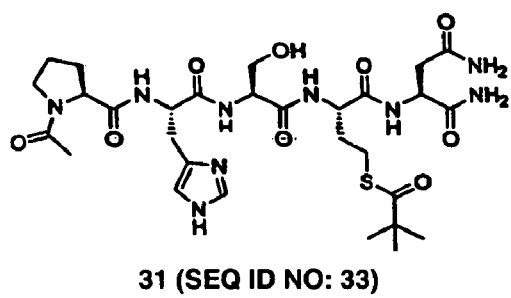
Figure 5:
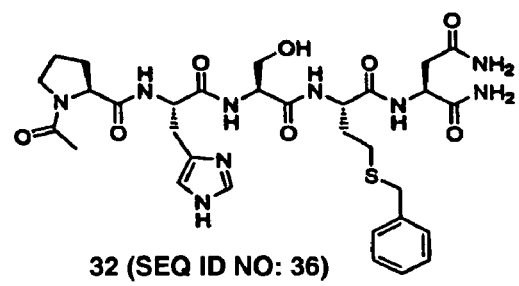
Figure 5:
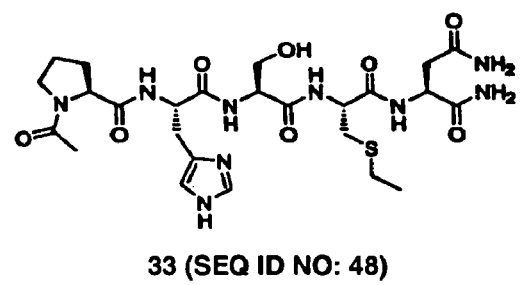
Figure 5:
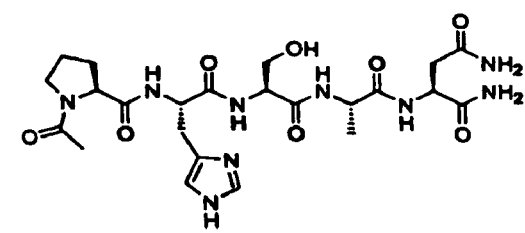
Figure 5:
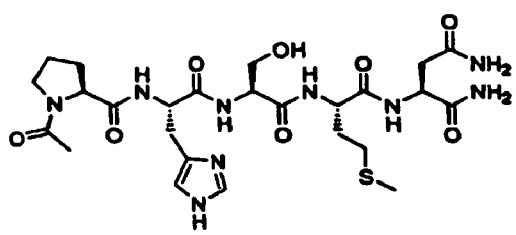

FIGS. 1–5 illustrate exemplary compounds of the invention.

5. DETAILED DESCRIPTION

5.1 Definitions

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl; prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms, even more preferably, from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —$C(O)R^{30}$, where $R^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Alkoxy" by itself or as part of another substituent refers to a radical —$OR^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkylsulfonyl" refers to a radical —$S(O)_2R^{32}$ where $R^{32}$ is an alkyl or cycloalkyl group as defined herein. Representative examples include, but are not limited to, methylsulfonyl, ethylsulfonyl, propylsulfonyl, butylsulfonyl and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably from 6 to 12 carbon atoms.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$–$C_{30}$) arylalkyl, e.g., the alkanyl, alkenyl or alkynyl moiety of the arylalkyl group is ($C_1$–$C_{10}$) and the aryl moiety is ($C_6$–$C_{20}$), more preferably, an arylalkyl group is ($C_6$–$C_{20}$) arylalkyl, e.g., the alkanyl, alkenyl or alkynyl moiety of the arylalkyl group is ($C_1$–$C_8$) and the aryl moiety is ($C_6$–$C_{12}$).

"Diagnostically effective amount" refers to the amount of an compound that, when administered to a patient for detection of a disease, is sufficient to detect the disease. The "diagnostically effective amount" will vary depending on the compound, the disease and its severity and the age, weight, etc., of the patient to be treated.

"Effective amount" refers to the amount of a compound that, when administered for example, to detect, induce or inhibit a particular property or condition is sufficient to detect the to detect, induce or inhibit the property or condition. The "effective amount" will vary depending on the antibody and the particular property or condition.

"Compounds" refers to compounds disclosed herein including those encompassed by the generic formula disclosed herein and compounds whose structure is disclosed herein. The compounds specifically include any multimeric forms of the amino acid sequences disclosed herein, therapeutic conjugates thereof and diagnostic conjugates thereof. The compounds may be identified either by their chemical structure and/or chemical name. When the chemical structure and chemical name conflict, the chemical structure is determinative of the identity of the compound. The compounds may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds also include isotopically labeled compounds where one or more atoms have an atomic mass different from the atomic mass conventionally found in nature. Examples of isotopes that may be incorporated into compounds of the invention include, but are not limited to, $^2H$, $^3H$, $^{13}C$, $^{14}C$, $^{15}N$, $^{18}O$, $^{17}O$, $^{31}P$, $^{32}P$ and $^{35}S$. Compounds may exist in unsolvated forms as well as solvated forms, including hydrated forms and as N-oxides. In general, the hydrated, solvated and N-oxide forms are within the scope of the present invention. Certain compounds may exist in multiple crystalline or amorphous forms. In general, all physical forms are equivalent for the uses contemplated by the present invention and are intended to be within the scope of the present invention. Further, it should be understood, when partial structures of compounds are illustrated, that brackets indicate the point of attachment of the partial structure to the rest of the molecule.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. Preferably, the cycloalkyl group is ($C_3$–$C_{10}$) cycloalkyl, more preferably ($C_3$–$C_7$) cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thuranes, imidazolidine, morpholine, piperazine, piperidine, pyrazolidine, pyrrolidine, quinuclidine, and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —NR$^{34}$R$^{35}$, =N—N=, —N=N—, —N=N—NR$^{36}$R$^{37}$, —PR$^{38}$—, —P(O)$_2$—, —POR$^{39}$—, —O—P(O)$_2$—, —SO—, —SO$_2$—, —SnR$^{40}$R$^{41}$— and the like, where R$^{34}$, R$^{35}$, R$^{36}$, R$^{37}$, R$^{38}$, R$^{39}$, R$^{40}$ and R$^{41}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5–20 membered heteroaryl, more preferably from 5–10 membered heteroaryl. Preferred heteroaryl groups are those derived from thiophene, pyrrole, benzothiophene, benzofuran, indole, pyridine, quinoline, imidazole, oxazole and pyrazine "Heteroarylsulfonyl" refers to a radical —S(O)$_2$R$^{42}$ where R$^{42}$ is an heteroaryl group as defined herein. Representative examples include, but are not limited to, pyridylsulfonyl, indolylsulfonyl, imidazolylsulfonyl and the like.

"Heteroarylalkyl" by itself or as part of another substituent refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6–30 membered heteroarylalkyl, e.g., the alkanyl, alkenyl or alkynyl moiety of the heteroarylalkyl is 1–10 membered and the heteroaryl moiety is a 5–20-membered heteroaryl, more preferably, 6–20 membered heteroarylalkyl, e.g., the alkanyl, alkenyl or alkynyl moiety of the heteroarylalkyl is 1–8 membered and the heteroaryl moiety is a 5–12-membered heteroaryl.

"Oxycarbonyl" by itself or as part of another substituent refers to a radical —C(O)—OR$^{43}$ where R$^{43}$ represents an alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl substituted heteroaryl, heteroarylalkyl or substituted heteroarylalkyl group as defined herein. Representative examples include, but are not limited to, methoxycarbonyl, piperdineoxycarbonyl, phenyloxycarbonyl, benzyloxycarbonyl and the like.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutical composition" refers to at least one compound and a pharmaceutically acceptable vehicle, with which the compound is administered to a patient.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound is administered.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently, although not necessarily, pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, enamine, imine, N-phosphonyl, N-phosphoryl or N-sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1–8 (John Wiley and Sons, 1971–1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are independently replaced with the same or different substituent(s). Typical substituents include, but are not limited to, —M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O$_2$)O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is independently a halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. Preferably, substituents include —M, —$R^{60}$, =O, —$OR^{60}$, —$SR^{60}$, —$S^-$, =S, —$NR^{60}R^{61}$, =$NR^{60}$, —$CF$, —CN, —OCN, —SCN, —NO, —$NO_2$, =$N_2$, —$N_3$, —$S(O)_2R^{60}$, —$OS(O_2)O^-$, —$OS(O)_2R^{60}$, —$P(O)(O^-)_2$, —$P(O)(OR^{60})$ $(O^-)$, —$OP(O)(OR^{60})(OR^{61})$, —$C(O)R^{60}$, —$C(S)R^{60}$, $C(O)$ $OR^{60}$, —$C(O)NR^{60}R^{61}$, —$C(O)O^-$, —$NR^{62}C(O)NR^{60}R^{61}$, more preferably, —M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)$ $(OR^{60})(O^-)$, —$OP(O)(OR^{60})(OR^{61})$, —$C(O)R^{60}$, —$C(O)$ $OR^{60}$, —$C(O)NR^{60}R^{61}$, —$C(O)O^-$, most preferably, —M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

5.2 Compounds

In a first aspect, the present invention provides as compound of structural

Formula (I):

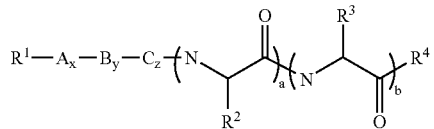

or a pharmaceutically available salt, solvate, hydrate or N-oxide thereof wherein:

a, b, x, y and z are 0 or 1;
A is a cyclic amino acid;
B is a basic amino acid;
C is a small amino acid;
$R^1$ is alkyl, substituted alkyl, acyl, substituted acyl, alkylsulfonyl, substituted alkylsulfonyl, arylalkyl, substituted arylalkyl, arylsulfonyl, substituted arylsulfonyl, heteroalkyl, substituted heteroalkyl, heteroarylsulfonyl, substituted heteroarylsulfonyl, heteroarylalkyl, substituted heteroarylalkyl, oxycarbonyl or substituted oxycarbonyl;
$R^2$ is alkyl, —$(CH_2)_mS(O)_nR^5$, —$(CH_2)_mS(O)_n$—$S(O)_oR^5$ or —$(CMe)_mS(O)_nR^5$
m is 1, 2, 3 or 4;
n and o are independently 0, 1 or 2;
$R^3$ is —$CH_2CONH_2$ or —$CH_2CH_2CONH_2$;
$R^4$ is alkyl, —$NR^6R^7$ or —$OR^8$;
$R^5$ is alkyl, substituted alkyl, acyl, substituted acyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, oxycarbonyl or substituted oxycarbonyl;
$R^6$ and $R^7$ are independently hydrogen or alkyl; and
$R^8$ is alkyl, substituted alkyl, aryl substituted aryl, arylalkyl, substituted arylalkyl, heteroalkyl, substituted heteroalkyl, heteroaryl, substituted heteroaryl, heteroarylalkyl or substituted heteroarylalkyl;
with the provisos that:
$R^5$ is not methyl when m is 1;
a is 1 unless A is proline, B is histidine, C is serine and b is 0 when a is 0; and
$R^2$ is —$(CH2)_mS(O)_nR^5$ or —$(CH_2)_mS(O)_n$—$S(O)_oR^5$ unless b, x, y and z are 1.

Cyclic amino acids include, for example, natural amino acids (e.g., proline) and unnatural amino acids (e.g., the four and six membered analogues of proline). Basic amino acids include, but are not limited to, natural amino acids such as arginine, histidine and lysine and unnatural amino acids such as homolysine and orthinine. Small amino acids include, for example, glycine, serine, alanine and threonine.

The use of unnatural amino acids in compounds is specifically contemplated. Such amino acids include, for example, the D-amino acids of the naturally occurring amino acids, β-alanine, 3-aminopropionic acid, 2,3 diaminopropionic acid, 4-aminobutyric acid, etc., sarcosine, orthinine, N-methyl glycine, citrulline, t-butyl alanine, homoarginine, etc.

One or amide bonds in compounds may be optionally replaced by isosteres such as —$CH_2$—NH—, —$CH_2$—S—, —$CH_2$—S(O)—, —$CH_2$—$S(O)_2$—, —$COCH_2$—, —CH=CH—, $CH(OH)CH_2$ which are well known in the art (see, e.g., Spatola, "Chemistry and Biochemistry of Amino Acids, Peptides and Proteins," B. Weinstein, (eds.), Marcel Dekker, N.Y., 1983; Spatola et al., *Life Sci.* 1986, 38:1243–1249; Almquist et al., *J. Med. Chem.* 1980, 23:1392; Holladay et al., *Tetrahedron Lett.* 1983, 24:4401; Hruby, *Life Sci.* 1982, 4; 189:199; Jennings-White et al., *Tetrahedron Lett.* 1982, 23:2533; Hruby, *Biopolymers* 1993; 33:1073–1082; Wiley et al., *Med. Res. Rev.* 1993 13:327–384; Moore et al., *Adv. in Pharmacol* 1995, 33:91–141; Giannis et al., 1997, *Adv. in Drug Res.* 29:1–78). The peptides may also contain peptide mimetics such as those described in Olson et al., *J. Med. Chem.* 1993, 36:3039 and Chorev et al, *Science* 1979, 204:1210.

In a second embodiment, A is proline, B is histidine, C is serine and $R^3$ is —$CH_2CONH_2$.

Preferably, in these first two embodiments, $R^1$ is acyl, substituted acyl, arylalkyl, substituted arylalkyl, oxycarbonyl or substituted oxycarbonyl. More preferably, $R^1$ is acyl, substituted acyl, oxycarbonyl or substituted oxycarbonyl.

In one embodiment of the first two embodiments, $R^2$ is —$(CH_2)_mS(O)_nR^5$ or —$(CH_2)_mS(O)_n$—$S(O)_oR^5$ and m is 1 or 2. In another embodiment of the first two embodiments, $R^4$ is $NR^7R^8$ and $R^7$ and $R^8$ are hydrogen.

In one embodiment of the first embodiment, a, b, x, y and z are 1. In another embodiment, x is 0 and a, b, y and z are 1. In still another embodiment, x and y are 0 and a, b and z are 1. In still another embodiment, x, y and z are 0 and a and b are 1. In still another embodiment, x, z, a and b are 1 and y is 0. In still another embodiment, x, a and b are 1 and y and z are 0. In still another embodiment, y, a and b are 1 and x and z are 0. In still another embodiment, x, y, z and a are 1 and b is 0. In still another embodiment, y, z and a are 1 and x and b are 0. In still another embodiment, x, y, z and b are 1 and a is 0. In still another embodiment, z and a are 1 and x, y and b are 0. In still another embodiment, a is 1 and x, y, z and b are 0. In still another embodiment, A is a D amino acid. In still another embodiment, A, B and C are L amino acids and the α carbons adjacent to $R^2$ and $R^3$, respectively have the L configuration.

In a third embodiment, A is proline, B is histidine, C is serine and $R^3$ is —$CH_2CONH_2$, $R^1$ is acyl, substituted acyl, oxycarbonyl and substituted oxycarbonyl, a, b, x, y and z are 1, m is 1 or 2, and $R^4$ is $NR^7R^8$ and $R^7$ and $R^8$ are hydrogen. Preferably, $R^1$ is acyl, more preferably, $R^1$ is —$C(O)CH_3$ and $R^2$ is alkyl. Preferably, $R^2$ is allyl or methyl.

In a more specific embodiment of the third embodiment, $R^1$ is —$C(O)CH_3$, $R^2$ is —$(CH_2)_mS(O)_nR^5$ and m is 1. In one embodiment, n is 0 and $R^5$ is alkyl or substituted alkyl. In another embodiment, n is 0 and $R^5$ is arylalkyl or substituted arylalkyl. In still another embodiment, n is 0 and $R^5$ is acyl or substituted acyl. In still another embodiment, n is 0 and $R^5$ is oxycarbonyl or substituted oxycarbonyl.

In another more specific embodiment of the third embodiment, $R^1$ is —$C(O)CH_3$, $R^2$ is —$(CH_2)_mS(O)_n$—$S(O)_oR^5$ and m is 1. Preferably, n and o are 0 and $R^5$ is alkyl or aryl.

In still another more specific embodiment of the third embodiment, $R^1$ is —$C(O)CH_3$, $R^2$ is —$(CH_2)_mS(O)_nR^5$ and m is 2. In one embodiment, n is 0 and $R^5$ is alkyl or arylalkyl. In another embodiment, n is 1 or 2 and $R^5$ is alkyl. In still another embodiment, n is 0 and $R^5$ is acyl.

In a fourth embodiment, A is proline, B is histidine, C is serine and $R^3$ is —$CH_2CONH_2$, $R^1$ is acyl, substituted acyl, oxycarbonyl and substituted oxycarbonyl, m is 1 or 2 and $R^4$ is $NR^7R^8$ and $R^7$ and $R^8$ are hydrogen. In one embodiment, x is 0 and a, b, y and z are 1. In another embodiment, x and y are 0 and a, b and z are 1. In still another embodiment, x, y and z are 0 and a and b are 1. In still another embodiment, y is 0 and a, b, x and z are 1. In still another embodiment, y and z are 0 and a, b and x are 1. In still another embodiment, x and z are 0 and a, b and y are 1. In still another embodiment, $R^1$ is 0 and a, x, y and z are 1. In still another embodiment, b and x are 0 and a, y and z are 1. In still another embodiment, b, x and y are 0 and a and z are 1. In still another embodiment, b, x, y and z are 0 and a is 1. Preferably, in the above embodiment, $R^1$ is acyl, $R^2$ is —$(CH_2)_mS(O)_nR^5$, m is 1 and $R^5$ is alkyl In a fifth embodiment, where A is proline, B is histidine, C is serine and $R^3$ is —$CH_2CONH_2$, a is 0 and b, x, y and z are 1.

FIGS. 1–5 illustrate exemplary compounds of structural formula (I). Another exemplary compound of the invention is Ac-Pro-His-Ser-Cys(β,β-dimethyl)-Asn-$NH_2$ (SEQ ID NO: 1).

Covalent modifications of the compounds of formula (I) are within the scope of the invention and may improve the solubility, absorption, biological half life, etc. Such modifications may be effected by selective reaction of specific amino acid residues with organic reagents. For example, histidine residues may be selectively reacted with diethylpyrocarbonate at pH 5.5–7 and p-bromophenacyl bromide at pH 6.0. Residues containing free amino groups may be selectively reacted with carboxylic acid anhydrides, imidoesters, pyridoxal phosphate, trinitrobenzenesulfonic acid, O-methylisourea, 2,4 pentanedione, glyoxylate, etc. Arginyl residues may be selectively reacted with phenylglyoxal, and various diones. Glutaminyl and asparaginyl residues may be deaminated under mildly acidic conditions to provide the corresponding glutamyl and aspartyl residues. Proline and lysine may be selectively hydroxylated while serine and threonine residues may be selectively phosphorylated. The α-amino groups of histidine and lysine may be selectively methylated (Creighton, *Proteins: Structure and Molecule Properties,* W. H. Freeman & Co., San Francisco, pp. 79–86 (1983)).

Derivatization with bi-functional cross-linking agents (e.g., 1-bis(diazoacetyl)-2-phenylethane, glutaraldehyde, N-hydroxy-succinimide esters, esters of 4-azidosalicylic acid, homobifunctional imidoesters (e.g., disuccinimidyl esters such as 3,3'-dithiobis(succinimidylpropionate)), bifunctional maleimides (e.g., bis-N-maleimido-1,8-octane, etc.) may be used to link compounds with water-insoluble support matrices or other macromolecular carriers. Photoactivatable agents such as methyl-3-[(p-azidophenyl)dithio] propioimidate may also be used to attach compounds with water-insoluble support matrices. Alternatively, compounds may be directly reacted with reactive water-insoluble matrices (e.g., cyanogen bromide-activated carbohydrates).

The present invention also includes longer peptides comprised of repeating units of the amino acid sequences of the compounds of structural formula (I). In one embodiment, the repeating unit of such a multimer is the amino acid sequence of a compound where a, b, x, y, and z are 1. In another embodiment, the repeating unit is the amino acid sequence of a compound of structural formula (I) where only one of a, b, x, y, and z is 0 and the rest are 1.

A multimer may be comprised of either the same or different combinations of repeating units comprised of amino acid sequences of compounds of structural formula (I). Such multimeric peptides can be made by either by chemical synthesis or by recombinant DNA techniques, followed by chemical modification of the cysteine residues. Preferably, the synthetic multimers have 2 to 12 repeats, more preferably, 2 to 8 repeats of the core peptide sequence. Accordingly, the total number of amino acids in the multimer should not exceed about 110 residues (or the equivalents, when including linkers or spacers).

A preferred multimer has the formula $P^1_n$ where $P^1$ is a pentapeptide, n is 2 to 8. In another embodiment, a multimer has the formula $(P^1—X_m)_n—P^2$ where $P^1$ and $P^2$ are pentapeptides. $P^1$ and $P^2$ may be the same or different and each $P^1$ may represent a different pentapeptide derivative of structural formula (I). X is $C_1$–$C_5$ alkyl, $C_1$–$C_5$ polyether containing up to 4 oxygen atoms or $Gly_z$ wherein, z=1–6, m =0 or 1 and n=1–7.

A preferred recombinantly produced peptide multimer has the formula: $(P^1—Gly_z)_n—P^2$ where $P^1$ and $P^2$ are pentapeptides which are the same or different and each $P^1$ in the multimer may be a different pentapeptide, n=1–100 and z=0–6. The multimer may be optionally functionalized at both the N— and C-termini.

Compounds of structural formula (I) may be modified by the covalent attachment of any type of molecule as long as the modification does not prevent or inhibit biological function (i.e., inhibition or prevention of angiogenesis, cell invasion, cell proliferation, etc.). For example, a compound of structural formula (I) may be modified by glycosylation, acetylation, pegylation, phosphorylation, amidation, proteolytic cleavage, linkage to cellular ligand or protein, etc. Preferably, compounds of structural formula (I) are conjugated to a therapeutic agent or a diagnostic agent either directly or through a linking moiety.

Preferably, the linking moiety is first attached to a diagnostic or therapeutic agent to form a linking moiety intermediate which is then further attached to a compound of structural formula (I). As will be apparent to the skilled artisan, the linking moiety can also be first attached to a compound of structural formula (I) to form a linking moiety intermediate which can then be attached to a diagnostic agent or therapeutic agent.

Typically, a linking moiety will include a linker and a linking group for conjugating a therapeutic agent or diagnostic agent to a peptide. The nature of the linker will depend upon the particular application and the type of conjugation desired as the linker may be hydrophilic or hydrophobic, long or short, rigid or flexible. The linker may be optionally substituted with one or more linking groups which may be either the same or different, accordingly providing polyvalent linking moieties which are capable of conjugating multiple therapeutic agents or diagnostic agents with a antibody.

A wide variety of linkers comprised of stable bonds suitable for spacing linking groups from the amino nitro compound are known in the art, and include by way of example and not limitation, alkyl, heteroalkyl, acyclic heteroatomic bridges, aryl, arylaryl, arylalkyl, heteroaryl, heteroaryl-heteroaryl, substituted heteroaryl-heteroaryl, heteroarylalkyl, heteroaryl-heteroalkyl and the like. Thus, the linker may include single, double, triple or aromatic carbon-carbon bonds, nitrogen-nitrogen bonds, carbon-nitrogen, carbon-oxygen bonds and/or carbon-sulfur bonds. Accordingly, functionalities such as carbonyls, ethers, thioethers, carboxamides, sulfonamides, ureas, urethanes, hydrazines, etc. may be included in a linker.

Choosing a suitable linker is within the capabilities of those of skill in the art. For example, where a rigid linker is desired, the linker may be rigid polyunsaturated alkyl or an aryl, biaryl, heteroaryl, etc. Where a flexible linker is desired, the linker may be a flexible peptide such as Gly-Gly-Gly or a flexible saturated alkanyl or heteroalkanyl. Hydrophilic linkers may be, for example, polyalcohols or polyethers such as polyalkyleneglycols. Hydrophobic linkers may be, for example, alkyls or aryls.

Preferably, a linking group is capable of mediating formation of a covalent bond with complementary reactive functionality of, for example, a compound of structural formula (I) to provide the therapeutic agent or diagnostic agent conjugated to the peptide. Accordingly, the linking group may be any reactive functional group known to those of skill in the art that will react with common chemical groups found in peptides (e.g., amino, sulfhydryl, hydroxyl, carboxylate, imidizaloyl, guandinium, amide, etc.). Accordingly, the linking group may be, for example, a photochemically activated group, an electrochemically activated group, a free radical donor, a free radical acceptor, a nucleophilic group or an electrophilic group. However, those of skill in the art will recognize that a variety of functional groups which are typically unreactive under certain reaction conditions can be activated to become reactive. Groups that can be activated to become reactive include, e.g., alcohols, carboxylic acids and esters, including salts thereof.

The linking group may be —$NHR^1$, —$NH_2$, —OH, —SH, halogen, —CHO, —$R^1CO$, —$SO_2H$, —$PO_2H$, —$N_3$, —CN, —$CO_2H$, —$SO_3H$, —$PO_3H$, —$PO_2(OR^1)H$, —$CO_2R^1$, —$SO_3R^1$ or —$PO(OR^1)_2$ where $R^1$ is alkyl. Preferably, the linking group is —$NHR^1$, —$NH_2$, —OH, —SH, —CHO, —$CO_2H$, $R^1CO$—, halogen and —$CO_2R^1$.

Some embodiments of the linker and the linking group include, for example, compounds where the linker is —$(CH_2)_n$—, n is an integer between 1 and 8, the linking group is —$NH_2$, —OH, —$CO_2H$, and —$CO_2R^1$ and the corresponding analogues where any suitable hydrogen is substituted. Other embodiments of the linking moiety include any amino acid, which may be, for example, a D or L amino acid. Thus, the linking moiety may be a dipeptide, a tripeptide or a tetrapeptide comprised of any combination of amino acids. The polarity of the peptide bond in these peptides may be either C—N or N—C.

Therapeutic agents and diagnostic agents may be linked to compounds of structural formula (I) directly using a variety of conventional reactions known to the skilled artisan. For example, condensation reagents (e.g., carbodiimides, carbonyldiimidazoles, etc.) may be used to form an amide bond linkage between an amino group of the therapeutic or diagnostic agent and the carboxylic acid groups of residues such as glutamic acid, aspartic acid and the C-terminal carboxyl group of a compound of structural formula (I).

Similar methods may be used to attach therapeutic agents and diagnostic agents containing a linker and linking group to compounds of structural formula (I). For example, diagnostic agents and therapeutic agents containing a linker and linking group may be attached to the amino group of lysine, the carboxylic acid groups of glutamic acid and aspartic acid, the sulfhydryl group of cysteine, the hydroxyl groups of threonine and serine and the various moieties of aromatic amino acids of compounds of structural formula (I) using conventional approaches known to the skilled artisan. In general, selection of an appropriate strategy for conjugating diagnostic agents or therapeutic agents to a compound of structural formula (I) either directly or through a linker and linking group is well within the ambit of the skilled artisan.

Therapeutic agents which can be conjugated to compounds of structural formula (I) include, but are not limited to, radionuclides, protein toxins (e.g., ricin, *Pseudomonas* exotoxin, diptheria toxin, saporin, pokeweed antiviral protein, bouganin, etc.), cytotoxic cancer agents, camptothecins (e.g., 9-nitrocamptothecin (9NC), 9-aminocamptothecin (9AC), 10-aminocamptothecin, 9-chlorocamptothecin, 10,11-methylendioxycamptothecin, irinothecin, aromatic camptothecin esters, alkyl camptothecin esters, topotecan, (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione methanesulfonate dihydrate (DX-8951f), 7-[(2-trimethyl-silyl)ethyl]-20(S)camptothecin (BNP1350), Rubitecan, Exatecan, Lurtotecan, Diflomotecan and other homocamptothecins, etc.), taxanes (e.g., taxol), epithilones, calicheamycins, hydroxy urea, cytarabine, cyclophosamide, ifosamide, nitrosureas, cisplatin, mitomycins maytansines, carboplatin, dacarbazine, procarbazine, etoposides, tenoposide, bleomycin, doxurobicin, 2-pyrrolinodoxurobicin, daunomycin, idarubican, daunorubicin, dactinomycin, plicamycin, mitoxantrone, asparginase, dihydroxy anthracine dione, mithrimycin, actinomycin D, 1-dehydrotestosterone, cytochlasins, vinblastine, vincristine, vinorelbine, paclitaxel, docetaxel, gramicidin D, glucocorticoids, anthracyclines, procaine, teracaine, lidocaine, propanolol, puromycin, methotrexate, 6-mercaptopurine, 6-thioguanine, mustard toxins, anthyrimycin, paclitaxel, alkylating agents (e.g., mechoremethamine, thioepa chlorambucil, melphalan, carmustine, loustine, cyclothosphamide, busulfan, dibromomannitol, streptozotocin, etc.) homologues and analogues thereof. Preferably, the therapeutic agent is a cytotoxic cancer agent, such as, for example, a taxane, a camptothecin, an epithilone or a anthracycline. In one embodiment, the therapeutic agent is doxorubicin. In another embodiment the therapeutic agent is a radionuclide.

The term "diagnostically labeled" means that a compound of structural formula (I) has an attached diagnostically detectable label. Many different labels exist in the art and methods of labeling are well known the skilled artisan. General classes of labels, which can be used in the present invention, include but are not limited to, radioactive isotopes, paramagnetic isotopes, compounds which can be imaged by positron emission tomography (PET), fluorescent or colored compounds, compounds which can be imaged by magnetic resonance, chemiluminescent compounds, bioluminescent compounds, etc. Suitable detectable labels include, but are not limited to, radioactive, fluorescent, fluorogenic or chromogenic labels. Useful radiolabels (radionuclides), which are detected simply by gamma counter, scintillation counter or autoradiography include, but are not limited to, $^3$H, $^{125}$I, $^{131}$I, $^{35}$S and $^{14}$C.

Methods and compositions for complexing metals to peptides are well known in the art. The metals are preferably detectable metal atoms, including radionuclides, and are complexed to proteins and other molecules (See, e.g., U.S. Pat. Nos. 5,627,286, 5,618,513, 5,567,408, 5,443,816 and 5,561,220).

Common fluorescent labels include, but are not limited to, fluorescein, rhodamine, dansyl, phycoerythrin, phycocyanin, allophycocyanin, o-phthaldehyde and fluorescamine (Haugland, *Handbook of Fluorescent Probes and Research Chemicals,* Sixth Ed., Molecular Probes, Eugene, Oreg., 1996) may be used to label compounds of structural formula (I). Fluorescein, fluorescein derivatives and fluorescein-like molecules such as Oregon Green™ and its derivatives, Rhodamine Green™ and Rhodol Green™, are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green™ derivatives with substituents on the nitrogens are preferred labeling reagents. This group includes the tetramethylrhodamines, X-rhodamines and Texas Red™ derivatives. Other preferred fluorophores are those excited by ultraviolet light. Examples include, but are not limited to, cascade blue, coumarin derivatives, naphthalenes (of which dansyl chloride is a member), pyrenes and pyridyloxazole derivatives.

Inorganic materials such as semiconductor nanocrystals (Bruchez, et al., 1998, *Science* 281:2013–2016) and quantum dots, e.g., zinc-sulfide-capped Cd selenide (Chan, et al., *Science* 1998, 281:2016–2018) may also be used as diagnostic labels.

Compounds of structural formula (I) can also be labeled with fluorescence-emitting metals such as $^{152}$Eu or others of the lanthanide series. These metals can be attached to compounds of structural formula (I) through acyl chelating groups such as diethylenetriaminepentaacetic acid (DTPA), ethylene-diamine-tetraacetic acid (EDTA), etc.

Radionuclides may be attached to compounds of structural formula (I) either directly or indirectly using an acyl chelating group such as DTPA and EDTA for in vivo diagnosis. The chemistry of chelation is well known in the art and varying ranges of chelating agent to peptide may be used to provide the labeled peptide. Of course, the labeled peptide must retain the biological activity of the native peptide.

Any radionuclide having diagnostic or therapeutic value can be used as the radiolabel in the present invention. In a preferred embodiment, the radionuclide is a γ-emitting or beta-emitting radionuclide, for example, one selected from the lanthanide or actinide series of the elements. Positron-emitting radionuclides, e.g. $^{68}$Ga or $^{64}$Cu, may also be used. Suitable gamma-emitting radionuclides include those which are useful in diagnostic imaging applications. The gamma-emitting radionuclides preferably have a half-life of from 1 hour to 40 days, preferably from 12 hours to 3 days. Examples of suitable gamma-emitting radionuclides include $^{67}$Ga, $^{111}$In, $^{99m}$Tc, $^{169}$Yb and $^{186}$Re. Most preferably, the radionuclide is $^{99m}$Tc.

Examples of preferred radionuclides (ordered by atomic number) are $^{67}$Cu, $^{67}$Ga, $^{68}$Ga, $^{72}$As, $^{89}$Zr, $^{90}$Y, $^{97}$Ru, $^{99}$Tc, $^{111}$In, $^{123}$I, $^{125}$I, $^{131}$I, $^{169}$Yb, $^{186}$Re, and $^{201}$Tl. Though limited work have been done with positron-emitting radiometals as labels, certain proteins, such as transferrin and human serum albumin, have been labeled with $^{68}$Ga.

A number of metals (not radioisotopes) useful for magnetic resonance imaging include gadolinium, manganese, copper, iron, gold and europium. Gadolinium is most preferred. Generally, the amount of labeled peptide needed for detectability in diagnostic use will vary depending on considerations such as age, condition, sex, and extent of disease in the patient, contraindications, if any, and other variables, and is to be adjusted by the individual physician or diagnostician. Dosage can vary from 0.01 mg/kg to 100 mg/kg.

Compounds of structural formula (I) may also be detected by coupling to a phosphorescent or a chemiluminescent compound, as is well known to the skilled artisan. Preferred chemiluminescent compounds include but are not limited to, luminol, isoluminol, theromatic acridinium ester, imidazole, acridinium salt and oxalate ester. Similarly, bioluminescent compounds may be used to detect antibodies and/or conjugates thereof and include, but are not limited to, luciferin, luciferase and aequorin.

Colorimetric detection, based on chromogenic compounds which have, or result in, chromophores with high extinction coefficients may also be used to detect compounds of structural formula (I).

5.3 Synthesis of Compounds of Structural Formula (I)

Compounds of structural formula (I) may be obtained via conventional synthetic methods. Starting materials useful for preparing compounds and intermediates thereof are commercially available or can be prepared by well-known synthetic methods.

Peptides may be prepared using solid-phase synthesis such as that generally described by Merrifield, *J. Amer. Chem. Soc.* 1963, 85:2149–54 using automated equipment, which may be purchased from chemical suppliers (e.g., Applied Biosystems, Foster City, Calif.). Solid-phase peptide synthesis may be initiated from the C-terminus of the peptide by coupling a protected α-amino acid (either Boc or FMOC protected), to a suitable resin. Such a starting material can be prepared by attaching an α-amino-protected amino acid by an ester linkage to a chloromethylated resin, hydroxymethyl resin, BHA resin, MBHA resin or a Rink resin. Such methods, well-known in the art, are disclosed, for example, in U.S. Pat. No. 5,994,309. Alternatively, compounds may be made by solution phase synthesis using protected α-amino acids (see e.g., Bodanszky, "Methods of Peptide Synthesis," Springer Verlag, N.Y., 1984). As is apparent to those of skill in the art, unnatural amino acids can be easily employed in the above standard methods of chemical synthesis and may be made by conventional methods know to those of skill in the art.

The skilled artisan will appreciate that two general synthetic strategies exist for synthesis of compounds of structural formula (I). Compounds with sulfur containing amino acids may be synthesized either directly by incorporation of the appropriate sulfur containing amino acid into a standard method of chemical synthesis as described above or indirectly by selective functionalization of an appropriate thiol containing peptide precursor and, if necessary, selective oxidation of the resultant thioether containing peptide. Methods for selectively functionalizing free thiols (e.g., selective alkylation, acylation, disulfide formation, etc.) in the presence of diverse organic functionality are well known to the skilled artisan as are methods of oxidizing sulfides to sulfoxides (e.g., $NaBO_3$, acetonitrile: water, $NaIO_4$, acetonitrile: water, etc.) and sulfones (e.g., $H_2O_2$, $HCO_2H$).

5.4 Assays for Compounds

Those of skill in the art will appreciate that the in vitro and in vivo assays useful for measuring the activity of compounds described herein are illustrative rather than comprehensive.

5.4.1 Assay for Endothelial Cell Migration

For endothelial cell (EC) migration, transwells are coated with type I collagen (50 μg/mL) by adding 200 μL of the collagen solution per transwell, then incubating overnight at 37° C. The transwells are assembled in a 24-well plate and a chemoattractant (e.g., FGF-2) is added to the bottom chamber in a total volume of 0.8 mL media. ECs, such as human umbilical vein endothelial cells (HUVEC), which have been detached from monolayer culture using trypsin, are diluted to a final concentration of about $10^6$ cells/mL with serum-free media and 0.2 mL of this cell suspension is added to the upper chamber of each transwell. Inhibitors to be tested may be added to both the upper and lower chambers and the migration is allowed to proceed for 5 hrs in a humidified atmosphere at 37° C. The transwells are removed from the plate stained using DiffQuik®. Cells which did not migrate are removed from the upper chamber by scraping with a cotton swab and the membranes are detached, mounted on slides, and counted under a high-power field (400×) to determine the number of cells migrated.

5.4.2 Biological Assay of Anti-Invasive Activity

The ability of cells such as ECs or tumor cells (e.g., PC-3 human prostatic carcinoma) cells to invade through a reconstituted basement membrane (Matrigel®) in an assay known as a Matrigel® invasion assay system has been described in detail in the art (Kleinman et al., *Biochemistry* 1986, 25: 312–318; Parish et al., 1992, *Int. J Cancer* 52:378–383). Matrigel® is a reconstituted basement membrane containing type IV collagen, laminin, heparin sulfate proteoglycans such as perlecan, which bind to and localize bFGF, vitronectin as well as transforming growth factor-β (TGFβ), urokinase-type plasminogen activator (uPA), tissue plasminogen activator (tPA) and the serpin known as plasminogen activator inhibitor type 1 (PAI-1) (Chambers et al., *Canc. Res.* 1995, 55:1578–1585). It is accepted in the art that results obtained in this assay for compounds which target extracellular receptors or enzymes are predictive of the efficacy of these compounds in vivo (Rabbani et al., *Int. J. Cancer* 1995, 63: 840–845).

Such assays employ transwell tissue culture inserts. Invasive cells are defined as cells which are able to traverse through the Matrigel® and upper aspect of a polycarbonate membrane and adhere to the bottom of the membrane. Transwells (Costar) containing polycarbonate membranes (8.0 μm pore size) are coated with Matrigel® (Collaborative Research), which has been diluted in sterile PBS to a final concentration of 75 μg/mL (60 μL of diluted Matrigel® per insert), and placed in the wells of a 24-well plate. The membranes are dried overnight in a biological safety cabinet, then rehydrated by adding 100 μL of DMEM containing antibiotics for 1 hour on a shaker table. The DMEM is removed from each insert by aspiration and 0.8 mL of DMEM/10% FBS/antibiotics is added to each well of the 24-well plate such that it surrounds the outside of the transwell ("lower chamber"). Fresh DMEM/antibiotics (100 μL), human Glu-plasminogen (5 μg/mL), and any inhibitors to be tested are added to the top, inside of the transwell ("upper chamber"). The cells which are to be tested are trypsinized and resuspended in DMEM/antibiotics, then added to the top chamber of the transwell at a final concentration of 800,000 cells/mL. The final volume of the upper chamber is adjusted to 200 μL. The assembled plate is then incubated in a humid 5% $CO_2$ atmosphere for 72 hours. After incubation, the cells are fixed and stained using DiffQuik® (Giemsa stain) and the upper chamber is then scraped using a cotton swab to remove the Matrigel® and any cells which did not invade through the membrane. The membranes are detached from the transwell using an X-acto® blade, mounted on slides using Permount® and cover-slips, then counted under a high-powered (400×) field. An average of the cells invaded is determined from 5–10 fields counted and plotted as a function of inhibitor concentration.

5.4.3 Tube-Formation Assays of Anti-Angiogenic Activity

Endothelial cells, for example, human umbilical vein endothelial cells (HUVEC) or human microvascular endothelial cells (HMVEC) which can be prepared or obtained commercially, are mixed at a concentration of $2 \times 10^5$ cells/mL with fibrinogen (5 mg/mL in phosphate buffered saline (PBS) in a 1:1 (v/v) ratio. Thrombin is added (5 units/ mL final concentration) and the mixture is immediately transferred to a 24-well plate (0.5 mL per well). The fibrin gel is allowed to form and then VEGF and bFGF are added to the wells (each at 5 ng/mL final concentration) along with the test compound. The cells are incubated at 37° C. in 5% $CO_2$ for 4 days at which time the cells in each well are counted and classified as either rounded, elongated with no branches, elongated with one branch, or elongated with 2 or more branches. Results are expressed as the average of 5 different wells for each concentration of compound. Typically, in the presence of angiogenic inhibitors, cells remain either rounded or form undifferentiated tubes (e.g. 0 or 1 branch). This assay is recognized in the art to be predictive of angiogenic (or anti-angiogenic) efficacy in vivo (Min et al., *Cancer Res.* 1996, 56: 2428–2433).

In an alternate assay, endothelial cell tube formation is observed when endothelial cells are cultured on Matrigel® (Schnaper et al., *J. Cell. Physiol.* 1995, 165:107–118). Endothelial cells ($1 \times 10^4$ cells/well) are transferred onto Matrigel®-coated 24-well plates and tube formation is quantitated after 48 hrs. Inhibitors are tested by adding them either at the same time as the endothelial cells or at various time points thereafter. Tube formation can also be stimulated by adding (a)

angiogenic growth factors such as bFGF or VEGF, (b) differentiation stimulating agents (e.g., PMA) or (c) a combination of these.

While not wishing to be bound by theory, this assay models angiogenesis by presenting to the endothelial cells a particular type of basement membrane, namely the layer of matrix which migrating and differentiating endothelial cells might be expected to first encounter. In addition to bound growth factors, the matrix components found in Matrigel® (and in basement membranes in situ) or proteolytic products thereof may also be stimulatory for endothelial cell tube formation which makes this model complementary to the fibrin gel angiogenesis model previously described (Blood et al., *Biochim. Biophys. Acta* 1990, 1032:89–118; Odedra al., *Pharmac. Ther.* 1991, 49:111–124).

5.4.4. Assays for Inhibition of Proliferation

The ability of compounds to inhibit the proliferation of EC's may be determined in a 96-well format. Type I collagen (gelatin) is used to coat the wells of the plate (0.1–1 mg/mL in PBS, 0.1 mL per well for 30 minutes at room temperature). After washing the plate (3×w/PBS), 3–6,000 cells are plated per well and allowed to attach for 4 hrs (37° C./5% $CO_2$) in Endothelial Growth Medium (EGM; Clonetics) or M199 media containing 0.1–2% FBS. The media and any unattached cells are removed at the end of 4 hrs and fresh media containing bFGF (1–10 ng/mL) or VEGF (1–10 ng/mL) is added to each well. Compounds to be tested are added last and the plate is allowed to incubate (37° C./5% $CO_2$) for 24–48 hrs. MTS (Promega) is added to each well and allowed to incubate from 1–4 hrs. The absorbance at 490 nm, which is proportional to the cell number, is then measured to determine the differences in proliferation between control wells and those containing test compounds.

A similar assay system can be set up with cultured adherent tumor cells. However, collagen may be omitted in this format. Tumor cells (e.g., 3,000–10,000/well) are plated and allowed to attach overnight. Serum free medium is then added to the wells, and the cells are synchronized for 24 hrs. Medium containing 10% FBS is then added to each well to stimulate proliferation. Compounds to be tested are included in some of the wells. After 24 hrs, MTS is added to the plate and the assay developed and read as described above.

5.4.5 Assays of Cytotoxicity

The anti-proliferative and cytotoxic effects of compounds may be determined for various cell types including tumor cells, ECs, fibroblasts and macrophages. This is especially useful when testing a compound which has been conjugated to a therapeutic moiety such as a radiotherapeutic or a toxin. For example, a conjugate of one of the compounds with Bolton-Hunter reagent which has been iodinated with $^{131}I$ would be expected to inhibit the proliferation of cells expressing an PHSCN binding site/receptor (most likely by inducing apoptosis). Anti-proliferative effects would be expected against tumor cells and stimulated endothelial cells but, under some circumstances not quiescent endothelial cells or normal human dermal fibroblasts. Any anti-proliferative or cytotoxic effects observed in the normal cells may represent non-specific toxicity of the conjugate.

A typical assay would involve plating cells at a density of 5–10,000 cells per well in a 96-well plate. The compound to be tested is added at a concentration 10× the $IC_{50}$ measured in a binding assay (this will vary depending on the conjugate) and allowed to incubate with the cells for 30 minutes. The cells are washed 3× with media, then fresh media containing [$^3H$]thymidine (1 µCi/mL) is added to the cells and they are allowed to incubate at 37° C. in 5% $CO_2$ for 24 and 48 hours. Cells are lysed at the various time points using 1 M NaOH and counts per well determined using a β-counter. Proliferation may be measured non-radioactively using MTS reagent or CyQuant® to measure total cell number. For cytotoxicity assays (measuring cell lysis), a Promega 96-well cytotoxicity kit is used. If there is evidence of anti-proliferative activity, induction of apoptosis may be measured using TumorTACS (Genzyme).

5.4.6 Caspase-3 Activity

The ability of compounds to promote apoptosis of EC's may be determined by measuring activation of caspase-3. Type I collagen (gelatin) is used to coat a P100 plate and $5×10^5$ ECs are seeded in EGM containing 10% FBS. After 24 hours (at 37° C. in 5% $CO_2$) the medium is replaced by EGM containing 2% FBS, 10 ng/ml bFGF and the desired test compound. The cells are harvested after 6 hours, cell lysates prepared in 1% Triton and assayed using the EnzChek®Caspase-3 Assay Kit #1 (Molecular Probes) according to the manufactures' instructions.

5.4.7. Corneal Angiogenesis Model

The protocol used is essentially identical to that described by Volpert et al., *J. Clin. Invest.* 1996, 98:671–679. Briefly, female Fischer rats (120–140 gms) are anesthetized and pellets (5 µl) comprised of Hydron®, bFGF (150 nM), and the compounds to be tested are implanted into tiny incisions made in the cornea 1.0–1.5 mm from the limbus. Neovascularization is assessed at 5 and 7 days after implantation. On day 7, animals are anesthetized and infused with a dye such as colloidal carbon to stain the vessels. The animals are then euthanized, the corneas fixed with formalin, and the corneas flattened and photographed to assess the degree of neovascularization. Neovessels may be quantitated by imaging the total vessel area or length or simply by counting vessels.

5.4.8 Matrigel® Plug Assay

This assay is performed essentially as described by Passaniti et al., 1992, *Lab Invest.* 67:519–528. Ice-cold Matrigel® (e.g., 500 µL) (Collaborative Biomedical Products, Inc., Bedford, Mass.) is mixed with heparin (e.g., 50 µg/ml), FGF-2 (e.g., 400 ng/ml) and the compound to be tested. In some assays, bFGF may be substituted with tumor cells as the angiogenic stimulus. The Matrigel® mixture is injected subcutaneously into 4–8 week-old athymic nude mice at sites near the abdominal midline, preferably 3 injections per mouse. The injected Matrigel® forms a palpable solid gel. Injection sites are chosen such that each animal receives a positive control plug (such as FGF-2+heparin), a negative control plug (e.g., buffer+heparin) and a plug that includes the compound being tested for its effect on angiogenesis, e.g., (FGF-2+heparin+compound). All treatments are preferably run in triplicate. Animals are sacrificed by cervical dislocation at about 7 days post injection or another time that may be optimal for observing angiogenesis. The mouse skin is detached along the abdominal midline, and the Matrigel® plugs are recovered and scanned immediately at high resolution. Plugs are then dispersed in water and incubated at 37° C. overnight. Hemoglobin (Hb) levels are determined using Drabkin's solution (e.g., obtained from Sigma) according to the manufacturers' instructions. The amount of Hb in the plug is an indirect measure of angiogenesis as it reflects the amount of blood in the sample. In addition, or alternatively, animals may be injected prior to sacrifice with a 0.1 ml buffer (preferably PBS) containing a high molecular weight dextran to which is conjugated a fluorophore. The amount of fluorescence in the dispersed plug, determined fluorimetrically, also serves as a measure of angiogenesis in the plug. Staining with mAb anti-CD31 (CD31 is "platelet-endothelial cell adhesion molecule or PECAM") may also be used to confirm neovessel formation and microvessel density in the plugs.

5.4.9 Chick Chorioallantoic Membrane (CAM) Angiogenesis Assay

This assay is performed essentially as described by Nguyen et al., *Microvascular Res.* 1994, 47:31–40. A mesh containing either angiogenic factors (bFGF) or tumor cells plus inhibitors is placed onto the CAM of an 8-day old chick embryo and the CAM observed for 3–9 days after implantation of the sample. Angiogenesis is quantitated by determining the percentage of squares in the mesh which contain blood vessels.

5.4.10 In Vivo Assessment of Angiogenesis Inhibition and Anti-Tumor Effects Using the Matrigel® Plug Assay with Tumor Cells In this assay, tumor cells, for example $1–5 \times 10^6$ cells of the 3LL Lewis lung carcinoma or the rat prostate cell line Mat-LyLu, are mixed with Matrigel® and then injected into the flank of a mouse following the protocol described in Sec. B., above. A mass of tumor cells and a powerful angiogenic response can be observed in the plugs after about 5 to 7 days. The anti-tumor and anti-angiogenic action of a compound in an actual tumor environment can be evaluated by including it in the plug. Measurement is then made of tumor weight, Hb levels or fluorescence levels (of a dextran-fluorophore conjugate injected prior to sacrifice). To measure Hb or fluorescence, the plugs are first homogenize with a tissue homogenizer.

5.4.11 Xenograft Model of Subcutaneous (s.c.) Tumor Growth

Nude mice are inoculated with MDA-MB-231 cells (human breast carcinoma) or another appropriate human tumor cell line and Matrigel® ($1 \times 10^6$ cells in 0.2 mL) s.c. in the right flank of the animals. The tumors are staged to 200 mm3 and then treatment with a test composition is initiated (100 □g/animal/day given q.d. IP). Tumor volumes are obtained every other day and the animals are sacrificed after 2–6 weeks of treatment. The tumors are excised, weighed and paraffin embedded. Histological sections of the tumors are analyzed by H and E, anti-CD31, Ki-67, TUNEL, CD6 or other immunohistochemical staining.

5.4.12 Xenograft Model of Metastasis

The compounds are also tested for inhibition of late metastasis using an experimental metastasis model (Crowley et al., *Proc. Natl. Acad. Sci. USA* 1993, 90 5021–5025). Late metastasis involves the steps of attachment and extravasation of tumor cells, local invasion, seeding, proliferation and angiogenesis. Human prostatic carcinoma cells (PC-3) transfected with a reporter gene, preferably the green fluorescent protein (GFP) gene, but as an alternative with a gene encoding the enzymes chloramphenicol acetyl-transferase (CAT), luciferase or LacZ, are inoculated into nude mice. This approach permits utilization of either of these markers (fluorescence detection of GFP or histochemical colorimetric detection of enzymatic activity) to follow the fate of these cells. Cells are injected, preferably iv, and metastases identified after about 14 days, particularly in the lungs but also in regional lymph nodes, femurs and brain. This mimics the organ tropism of naturally occurring metastases in human prostate cancer. For example, GFP-expressing PC-3 cells ($1 \times 10^6$ cells per mouse) are injected iv into the tail veins of nude (nu/nu) mice. Animals are treated with a test composition at 100 µg/animal/day given q.d. IP. Single metastatic cells and foci are visualized and quantitated by fluorescence microscopy or light microscopic histochemistry or by grinding the tissue and quantitative colorimetric assay of the detectable label.

5.4.13. Inhibition of Spontaneous Metastasis In Vivo by PHSCN and Functional Derivatives The rat syngeneic breast cancer system employs Mat BIII rat breast cancer cells (Xing et al., *Int. J. Cancer* 1996, 67:423–429). Tumor cells, for example, about $10^6$ suspended in 0.1 mL PBS, are inoculated into the mammary fat pads of female Fisher rats. At the time of inoculation, a 14-day Alza osmotic mini-pump is implanted intraperitoneally to dispense the test compound. The compound is dissolved in PBS (e.g., 200 mM stock), sterile filtered and placed in the minipump to achieve a release rate of about 4 mg/kg/day. Control animals receive vehicle (PBS) alone or a vehicle control peptide in the minipump. Animals are sacrificed at about day 14. In the rats treated with the compounds of the present invention, significant reductions in the size of the primary tumor and in the number of metastases in the spleen, lungs, liver, kidney and lymph nodes (enumerated as discrete foci) may be observed. Histological and immunohistochemical analysis reveal increased necrosis and signs of apoptosis in tumors in treated animals. Large necrotic areas are seen in tumor regions lacking neovascularization. Human or rabbit PHSCN (SEQ ID NO: 2) and their derivatives to which $^{131}$I is conjugated (either 1 or 2 I atoms per molecule of peptide) are effective radiotherapeutics and are found to be at least twofold more potent than the unconjugated polypeptides. In contrast, treatment with control peptides fails to cause a significant change in tumor size or metastasis.

5.4.14. 3LL Lewis Lung Carcinoma: Primary Tumor Growth

This tumor line arose spontaneously as carcinoma of the lung in a C57BL/6 mouse (Malave et al., *J. Nat'l. Canc. Inst.* 1979, 62:83–88). It is propagated by passage in C57BL/6 mice by subcutaneous (sc) inoculation and is tested in semi-allogeneic C57BL/6×DBA/2 $F_1$ mice or in allogeneic C3H mice. Typically six animals per group for subcutaneously (sc) implant, or ten for intramuscular (im) implant are used. Tumor may be implanted sc as a 2–4 mm fragment, or im or sc as an inoculum of suspended cells of about $0.5–2 \times 10^6$-cells. Treatment begins 24 hours after implant or is delayed until a tumor of specified size (usually approximately 400 mg) can be palpated. The test compound is administered ip daily for 11 days Animals are followed by weighing, palpation, and measurement of tumor size. Typical tumor weight in untreated control recipients on day 12 after im inoculation is 500–2500 mg. Typical median survival time is 18–28 days. A positive control compound, for example cyclophosphamide at 20 mg/kg/injection per day on days 1–11 is used. Results computed include mean animal weight, tumor size, tumor weight, survival time. For confirmed therapeutic activity, the test composition should be tested in two multi-dose assays.

5.4.15 3LL Lewis Lung Carcinoma: Primary Growth and Metastasis Model

This assay is well known in the art (Gorelik et al., *J. Nat'l. Canc. Inst.* 1980, 65:1257–1264; Gorelik et al., *Rec. Results Canc. Res.* 1980, 75:20–28; Isakov et al., *Invasion Metas.* 2:12–32 (1982); Talmadge et al., *J. Nat'l. Canc. Inst.* 1982, 69:975–980; Hilgard et al., *Br. J. Cancer* 1977, 35:78–86). Test mice are male C57BL/6 mice, 2–3 months old. Following sc, im, or intra-footpad implantation, this tumor produces metastases, preferentially in the lungs. With some lines of the tumor, the primary tumor exerts anti-metastatic effects and must first be excised before study of the metastatic phase (see also U.S. Pat. No. 5,639,725).

Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95–99% (by trypan blue dye exclusion). Viable tumor cells ($3 \times 10^{4-5 \times 10^6}$) suspended in 0.05 ml PBS are injected subcutaneously, either in the dorsal region or into one hind foot pad of C57BL/6 mice. Visible tumors appear after 3–4 days after dorsal sc injection of $10^6$ cells. The day of tumor appearance and the diameters of established tumors are measured by caliper every two days. The treatment is given as one to five doses of peptide or derivative, per week. In another embodiment, the peptide is delivered by osmotic minipump.

In experiments involving tumor excision of dorsal tumors, when tumors reach about 1500 mm³ in size, mice are randomized into two groups: (1) primary tumor is completely excised; or (2) sham surgery is performed and the tumor is left intact. Although tumors from 500–3000 mm³ inhibit growth of metastases, 1500 mm³ is the largest size primary tumor that can be safely resected with high survival and without local regrowth. After 21 days, all mice are sacrificed and autopsied.

Lungs are removed and weighed. Lungs are fixed in Bouin's solution and the number of visible metastases is recorded. The diameters of the metastases are also measured using a binocular stereoscope equipped with a micrometer-containing ocular under 8× magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125}$IdUrd into lung cells (Thakur et al., *J. Lab. Clin. Med.* 1977, 89:217–228). Ten days following tumor amputation, 25 µg of fluorodeoxyuridine is inoculated into the peritoneums of tumor-bearing (and, if used, tumor-resected mice). After 30 min, mice are given 1 µCi of $^{125}$IdUrd (iododeoxyuridine). One day later, lungs and spleens are removed and weighed, and a degree of $^{125}$IdUrd incorporation is measured using a gamma counter.

In mice with footpad tumors, when tumors reach about 8–10 mm in diameter, mice are randomized into two groups: (1) legs with tumors are amputated after ligation above the knee joints; or (2) mice are left intact as nonamputated tumor-bearing controls. (Amputation of a tumor-free-leg in a tumor-bearing mouse has no known effect on subsequent metastasis, ruling out possible effects of anesthesia, stress or surgery). Mice are killed 10–14 days after amputation. Metastases are evaluated as described above.

Statistics: Values representing the incidence of metastases and their growth in the lungs of tumor-bearing mice are not normally distributed. Therefore, non-parametric statistics such as the Mann-Whitney U-Test may be used for analysis.

Study of this model by Gorelik et al., supra, showed that the size of the tumor cell inoculum determined the extent of metastatic growth. The rate of metastasis in the lungs of operated mice was different from primary tumor-bearing mice. Thus in the lungs of mice in which the primary tumor had been induced by inoculation of larger doses of 3LL cells ($1-5 \times 10^6$) followed by surgical removal, the number of metastases was lower than that in nonoperated tumor-bearing mice, though the volume of metastases was higher than in the nonoperated controls. Using $^{125}$IdUrd incorporation as a measure of lung metastasis, no significant differences were found between the lungs of tumor-excised mice and tumor-bearing mice originally inoculated with $10^6$ 3LL cells. Amputation of tumors produced following inoculation of $10^5$ tumor cells dramatically accelerated metastatic growth. These results were in accord with the survival of mice after excision of local tumors. The phenomenon of acceleration of metastatic growth following excision of local tumors had been repeatedly observed (for example, see U.S. Pat. No. 5,639,725). These observations have implications for the prognosis of patients who undergo cancer surgery.

5.5 Recombinant DNA Methods

General methods of molecular biology have been amply described in the art (Sambrook, et al., *Molecular Cloning: A Laboratory Manual,* 2nd (or later) Edition, Cold Spring Harbor Press, Cold Spring Harbor, N.Y., 1989; Ausube et al., *Current Protocols in Molecular Biology,* Vol. 2, Wiley-Interscience, New York, (current edition); Kriegler, *Gene Transfer and Expression: A Laboratory Manual* (1990); Glover, D M, editor, *DNA Cloning: A Practical Approach,* vol. I & II, IRL Press, 1985; Alberts et al., *Molecular Biology of the Cell,* 2nd (or later) Ed., Garland Publishing, Inc., New York, N.Y. (1989); Watson et al., *Recombinant DNA,* 2nd (or later) Ed., Scientific American Books, New York, 1992; and Old et al., *Principles of Gene Manipulation: An Introduction to Genetic Engineering,* 2nd (or later) Ed., University of California Press, Berkeley, Calif. (1981)).

Unless otherwise indicated, a particular nucleic acid sequence is intended to encompasses conservative substitution variants thereof (e.g., degenerate codon substitutions) and a complementary sequence. The term "nucleic acid" is synonymous with "polynucleotide" and is intended to include a gene, a cDNA molecule, an mRNA molecule, as well as a fragment of any of these such as an oligonucleotide, and further, equivalents thereof (explained more fully below). Sizes of nucleic acids are stated either as kilobases (kb) or base pairs (bp). These are estimates derived from agarose or polyacrylamide gel electrophoresis (PAGE), from nucleic acid sequences which are determined by the user or published. Protein size is stated as molecular mass in kilodaltons (kDa) or as length (number of amino acid residues). Protein size is estimated from PAGE, from sequencing, from presumptive amino acid sequences based on the coding nucleic acid sequence or from published amino acid sequences.

Specifically, DNA molecules encoding the amino acid sequence corresponding to the peptide multimers of the present invention, or active variants thereof, can be synthesized by the polymerase chain reaction (PCR) (see, for example, U.S. Pat. No. 4,683,202) using primers derived the sequence of the protein disclosed herein. These cDNA sequences can then be assembled into a eukaryotic or prokaryotic expression vector and the resulting vector can be used to direct the synthesis of the fusion polypeptide or its fragment or derivative by appropriate host cells, for example COS or CHO cells.

The term "nucleic acid" as used herein is intended to include such fragments or equivalents. The nucleic acid sequences of this invention can be DNA or RNA. Prokaryotic or eukaryotic host cells transformed or transfected to express the multimers are within the scope of the invention. For example, the peptide multimer may be expressed in bacterial cells such as *E. coli,* insect cells (baculovirus), yeast, or mammalian cells such as Chinese hamster ovary cells (CHO) or human cells (which are preferred for human therapeutic use of the transfected cells). Other suitable host are known to those skilled in the art. Expression in eukaryotic cells leads to partial or complete glycosylation and/or formation of relevant inter- or intra-chain disulfide bonds of the recombinant polypeptide. Examples of vectors for expression in yeast *S. cerevisiae* include pYepSec1 (Baldari et al., 1987, *EMBO J.* 6:229–234), pMFa (Kuijan et al., 1982 *Cell* 30:933–943), pJRY88 (Schultz et al., 1987, *Gene* 54:113–123), and pYES2 (Invitrogen Corporation, San Diego, Calif.). Baculovirus vectors available for expression of proteins in cultured insect cells (SF 9 cells) include the pAc series (Smith et al., 1983, *Mol. Cell Biol.* 3:2156–2165) and the pVL series (Lucklow et al., (1989) *Virology* 170:31–39). Generally, COS cells (Gluzman, 1981 *Cell* 23:175–182) are used in conjunction with such vectors as pCDM 8 (Aruffoet al., supra, for transient amplification/expression in mammalian cells, while CHO (dhfr-negative CHO) cells are used with vectors such as pMT2PC (Kaufman et al., 1987, *EMBO J.* 6:187–195) for stable amplification/expression in mammalian cells. The NS0 myeloma cell line (a glutamine synthetase expression system.) is available from Celltech Ltd.

Construction of suitable vectors containing the desired coding and control sequences employs standard ligation and restriction techniques which are well understood in the art. Isolated plasmids, DNA sequences, or synthesized oligonucleotides are cleaved, tailored, and re-ligated in the form desired. The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500–1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, *Nature* 1981, 292:756; Nambair et al., *Science* 1984, 223:1299; and Jay, *J. Biol. Chem.* 1984, 259:6311.

Synthetic oligonucleotides are prepared by either the phosphotriester method as described by references cited above or the phosphoramidite method as described by Beaucage et al., *Tetrahedron Lett.* 1981, 22:1859; and Matteucci et al., *J. Am. Chem. Soc.* 1981, 103:3185 and can be prepared using commercially available automated oligonucleotide synthesizers. Kinase treatment of single strands prior to annealing or for labeling is achieved using well-known methods.

Once the components of the desired vectors are thus available, they can be excised and ligated using standard restriction and ligation procedures. Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. If desired, size separation of the cleaved fragments may be performed by polyacrylamide gel or agarose gel electrophoresis using standard techniques. A general description of size separations is found in *Meth. Enzymol.* (1980) 65:499–560.

Any of a number of methods are used to introduce mutations into the coding sequence to generate variants if these are to be produced recombinantly. These mutations include simple deletions or insertions, systematic deletions, insertions or substitutions of clusters of bases or substitutions of single bases. Modifications of the DNA sequence are created by site-directed mutagenesis, a well-known technique for which protocols and reagents are commercially available (Zoller et al., *Nucleic Acids Res.* 1982, 10:6487–6500 and Adelman et al., *DNA* 1983, 2:183–193)). The isolated DNA is analyzed by restriction and/or sequenced by the dideoxy nucleotide method of Sanger, *Proc. Natl. Acad. Sci. USA* 1977, 74:5463) as further described by Messing et al., *Nucleic Acids Res.* 1981, 9:309, or by the method of Maxam et al., *Meth. Enzymol,* supra.

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts. In fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

5.6 Therapeutic Uses

In accordance with the invention, a compound and/or pharmaceutical composition thereof is administered to a patient, preferably a human, suffering from a disease characterized by aberrant vascularization. Aberrant vascularization includes abnormal neovascularization such as the formation of new blood vessels, larger blood vessels, more branched blood vessels and any other mechanism, which inappropriate or increased blood carrying capacity to a diseased tissue or site. The compounds and/or pharmaceutical compositions thereof may be used to treat aberrant vascularization.

Preferably, diseases characterized by aberrant vascularization include cancer (e.g., any vascularized tumor, preferably, a solid tumor, including but not limited to, carcinomas of the lung, breast, ovary, stomach, pancreas, larynx, esophagus, testes, liver, parotid, bilary tract, colon, rectum, cervix, uterus, endometrium, kidney, bladder, prostrate, thyroid, squamous cell carcinomas, adenocarcinomas, small cell carcinomas, melanomas, gliomas, neuroblastomas, sarcomas (e.g., angiosarcomas, chondrosarcomas)), arthritis, diabetes, arteriosclerosis, arteriovenous, malformations, corneal graft neovascularization, delayed wound healing, diabetic retinopathy, age related macular degeneration, granulations, burns, hemophilic joints, rheumatoid arthritis, hypertrophic scars, neovascular glaucoma, nonunion fractures, Osier Weber Syndrome, psoriasis, pyogenic, granuloma, retrolental fibroplasia, pterygium, scleroderma, trachoma, vascular adhesions, ocular neovascularization, parasitic diseases, hypertrophy following surgery, inhibition of hair growth, macular degeneration (including both wet and dry type), rheumatoid arthritis and osteoarthritis. More preferably, diseases characterized by aberrant vascularization include cancer, macular degeneration and rheumatoid arthritis.

Also contemplated are methods for treating a patient having a disease or condition associated with undesired cell migration, invasion, proliferation comprising administering to the subject an therapeutically effective amount of a compound and/or a pharmaceutical composition thereof. In the above methods, the patient has a tumor, and angiogenesis inhibition results in reduction in size or growth rate of the tumor or destruction of the tumor. Preferably, the subject is a human.

Other examples of diseases or conditions against which the above methods may be effective include primary growth of a solid tumor, leukemia or lymphoma, tumor invasion, metastasis or growth of tumor metastases; benign hyperplasia; atherosclerosis, myocardial angiogenesis; post-balloon angioplasty vascular restinosis, neointima formation following vascular trauma, vascular graft restinosis, coronary collateral formation, deep venous thrombosis, ischemic limb angiogenesis; telangiectasia, pyogenic granuloma, corneal disease, rubeosis, neovascular glaucoma, diabetic and other retinopathy, retrolental fibroplasias, diabetic neovascularization, macular degeneration, endometriosis, arthritis, fibrosis associated with a chronic inflammatory condition, traumatic spinal cord injury including ischemia, scarring or fibrosis, lung fibrosis, chemotherapy-induced fibrosis; wound healing with scarring and fibrosis, peptic ulcers, a bone fracture, keloids, or a disorder of vasculogenesis, hematopoiesis, ovulation, menstruation, pregnancy or placentation associated with pathogenic cell invasion or with angiogenesis.

A preferred disease or condition to be treated by the above methods are tumor growth, invasion or metastasis, particularly brain tumors. Examples of such brain tumors are astrocytoma, anaplastic astrocytoma, glioblastoma, glioblastoma multiformae, pilocytic astrocytoma, pleiomorphic xanthoastrocytoma, subependymal giant cell astrocytoma, fibrillary astrocytoma, gemistocytic astrocytoma, protoplasmic astrocytoma, oligodendroglioma, anaplastic oligodendroglioma, ependymoma, anaplastic ependymoma, myxopapillary ependymoma, subependymoma, mixed oligoastrocytoma and malignant oligoastrocytoma.

The above methods may also be used to treat uterine diseases such as endometriosis and pathogenic ocular neovascularization associated with, or a cause of, proliferative diabetic retinopathy, neovascular age-related macular degeneration, retinopathy of prematurity, sickle cell retinopathy or retinal vein occlusion.

Further, in certain embodiments, compounds and/or pharmaceutical compositions thereof are administered to a patient, preferably a human, as a preventative measure against various diseases or disorders characterized by aberrant vascularization. Thus, the compounds and/or pharmaceutical compositions thereof may be administered as a preventative measure to a patient having a predisposition for a disease characterized by aberrant vascularization. Accordingly, the compounds and/or pharmaceutical compositions thereof may be used for the prevention of one disease or disorder and concurrently treating another (e.g., preventing arthritis while treating cancer).

The suitability of the compounds and/or pharmaceutical compositions thereof in treating or preventing various diseases or disorders characterized by aberrant vascularization may be assayed by methods described herein and in the art. Accordingly, it is well with the capability of those of skill in the art to assay and use the compounds and/or pharmaceutical compositions thereof to treat or prevent diseases or disorders characterized by aberrant vascularization.

5.7 Diagnostic Uses and Methods

A compound and/or a pharmaceutical composition thereof is administered to a patient, preferably a human, in a diagnostically effective amount to detect or image a disease such as those listed in Section 5.6 above. Further, compounds and/or pharmaceutical compositions thereof may be used to detect or image diseases or conditions associated with undesired cell migration, invasion or prolifersation such as those listed above in Section 5.6 by administering to a subject an diagnostically effective amount of a compound and/or a pharmaceutical composition thereof.

Compounds may be diagnostically labeled and used, for example, to detect cell migration, cell invasion and cell proliferation. The disposition of a compound during and after binding may be followed in vitro or in vivo by using an appropriate method to detect the label. Diagnostically labeled compounds may be utilized in vivo for diagnosis and prognosis, for example, to image occult metastatic foci or for other types of in situ evaluations. For diagnostic applications, compounds may include bound linker moieties, which are well known to those of skill in the art In situ detection of the labeled compound may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

For diagnostic in vivo radioimaging, the type of detection instrument available is a major factor in selecting a radionuclide. The radionuclide chosen must have a type of decay which is detectable by a particular instrument. In general, any conventional method for visualizing diagnostic imaging can be utilized in accordance with this invention. Another factor in selecting a radionuclide for in vivo diagnosis is that its half-life be long enough so that the label is still detectable at the time of maximum uptake by the target tissue, but short enough so that deleterious irradiation of the host is minimized. In one preferred embodiment, a radionuclide used for in vivo imaging does not emit particles, but produces a large number of photons in a 140–200 keV range, which may be readily detected by conventional gamma cameras.

In vivo imaging may be used to detect occult metastases which are not observable by other methods. Compounds of the present invention may be used in diagnostic, prognostic or research procedures in conjunction with any appropriate cell, tissue, organ or biological sample of a desired animal species. By the term "biological sample" is intended any fluid or other material derived from the body of a normal or diseased subject, such as blood, serum, plasma, lymph, urine, saliva, tears, cerebrospinal fluid, milk, amniotic fluid, bile, ascites fluid, pus and the like. Also included within the meaning of this term is a organ or tissue extract and a culture fluid in which any cells or tissue preparation from the subject has been incubated.

Useful doses are defined as effective amount of a compound for the particular diagnostic measurement. Thus, an effective amount means an amount sufficient to be detected using the appropriate detection system e.g., magnetic resonance imaging detector, gamma camera, etc. The minimum detectable amount will depend on the ratio of labeled compound specifically bound to a tumor (signal) to the amount of labeled compound either bound non-specifically or found free in plasma or in extracellular fluid.

The amount of a composition to be administered depends on the precise compound selected, the disease or condition, the route of administration, and the judgment of the skilled imaging professional. Generally, the amount of a compound needed for detectability in diagnostic use will vary depending on considerations such as age, condition, sex, and extent of disease in the patient, contraindications, if any, and other variables, and is to be adjusted by the individual physician or diagnostician. Dosage can vary from 0.01 mg/kg to 100 mg/kg.

5.8 Therapeutic/Prophylactic Administration

The compounds and/or pharmaceutical compositions thereof may be advantageously used in human medicine. As previously described in Section 5.6 above, compounds of structural Formula (I) and/or pharmaceutical compositions thereof are useful for the treatment or prevention of various diseases or disorders characterized by aberrant vascularization.

When used to treat or prevent the above disease or disorders, compounds and/or pharmaceutical compositions thereof may be administered or applied singly, or in combination with other agents. The compounds and/or pharmaceutical compositions thereof may also be administered or applied singly, in combination with other pharmaceutically active agents (e.g., other anti-cancer agents, other anti-angiogenic agents such as chelators as zinc, penicillamine, thiomolybdate etc.), including other compounds.

The current invention provides methods of treatment and prophylaxis by administration to a patient of a therapeutically effective amount of a compound and/or pharmaceutical composition thereof. The patient may be an animal, is more preferably, a mammal and most preferably, a human.

The present compounds and/or pharmaceutical compositions thereof, may be administered orally. The compounds and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems (e.g., encapsulation in liposomes, microparticles, microcapsules, capsules, etc.) may be used to administer a compound and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds and/or pharmaceutical compositions thereof into the bloodstream.

In specific embodiments, it may be desirable to administer one or more compounds and/or pharmaceutical composition thereof locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of cancer or arthritis.

In certain embodiments, it may be desirable to introduce one or more compounds and/or pharmaceutical compositions thereof into the central nervous system by any suitable route, including intraventricular, intrathecal and epidural injection. Intraventricular injection may be facilitated by an intraventricular catheter, for example, attached to a reservoir, such as an Ommaya reservoir.

A compound and/or pharmaceutical composition thereof may also be administered directly to the lung by inhalation. For administration by inhalation, a compound and/or pharmaceutical composition thereof may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas) may be used to deliver compounds of the directly to the lung.

Alternatively, a Dry Powder Inhaler ("DPI") device may be used to administer a compound and/or pharmaceutical composition thereof to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator may be formulated containing a powder mix of a compound and a suitable powder base such as lactose or starch for these systems.

Another type of device that may be used to deliver a compound and/or pharmaceutical composition thereof to the lung is a liquid spray device supplied, for example, by Aradigm Corporation, Hayward, Calif. Liquid spray systems use extremely small nozzle holes to aerosolize liquid drug formulations that may then be directly inhaled into the lung.

In one embodiment, a nebulizer is used to deliver a compound and/or pharmaceutical composition of thereof to the lung. Nebulizers create aerosols from liquid drug formulations by using, for example, ultrasonic energy to form fine particles that may be readily inhaled (see e.g., Verschoyle et al., *British J. Cancer,* 1999, 80, Suppl. 2, 96, which is herein incorporated by reference). Examples of nebulizers include devices supplied by Batelle Pulmonary Therapeutics, Columbus, Ohio (See, Armer et al., U.S. Pat. No. 5,954,047; van der Linden et al., U.S. Pat. No. 5,950,619; van der Linden et al., U.S. Pat. No. 5,970,974).

In another embodiment, an electrohydrodynamic ("EHD") aerosol device is used to deliver a compound and/or pharmaceutical composition thereof to the lung. EHD aerosol devices use electrical energy to aerosolize liquid drug solutions or suspensions (see e.g., Noakes et al., U.S. Pat. No. 4,765,539). The electrochemical properties of the formulation may be important parameters to optimize when delivering a compound and/or pharmaceutical composition thereof to the lung with an EHD aerosol device and such optimization is routinely performed by one of skill in the art. EHD aerosol devices may more efficiently deliver drugs to the lung than existing pulmonary delivery technologies.

In another embodiment, the compounds and/or pharmaceutical compositions thereof can be delivered in a vesicle, in particular a liposome (see Langer, 1990, Science, 249:1527–1533; Treat et al., in "Liposomes in the Therapy of Infectious Disease and Cancer," Lopez-Berestein and Fidler (eds.), Liss, N.Y., pp. 353–365 (1989); see generally "Liposomes in the Therapy of Infectious Disease and Cancer," Lopez-Berestein and Fidler (eds.), Liss, N.Y., pp. 353–365 (1989)).

In another embodiment, the compounds and/or pharmaceutical compositions thereof can be delivered via sustained release systems, preferably, oral sustained release systems. In one embodiment, a pump may be used (Langer, supra; Sefton, 1987, CRC Crit. Ref. Biomed. Eng. 14:201; Saudek et al., 1989, N. Engl. J. Med. 321:574).

In another embodiment, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, N.Y. (1984); Langert al., 1983, J Macromol. Sci. Rev. Macromol Chem. 23:61; Levy et al., 1985, Science 228: 190; During et al., 1989, Ann. Neurol. 25:351; Howard et al., 1989, J. Neurosurg. 71:105). In another embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropyl methylcellulose). Other preferred cellulose ethers have been described (Alderman, Int. J. Pharm. Tech. & Prod. Mfr. 1984, 5(3) 1–9). Factors affecting drug release are well known to the skilled artisan and have been described in the art (Bamba et al., Int. J. Pharm. 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm. 2000, 26:695–708). In still another embodiment, OROS™ osmotic devices are used for oral sustained release delivery devices (Theeuwes et al., U.S. Pat. No. 3,845,770; Theeuwes et al., U.S. Pat. No. 3,916,899).

In yet another embodiment, a controlled-release system can be placed in proximity of the target of the compounds and/or pharmaceutical composition thereof, thus requiring only a fraction of the systemic dose (see, e.g., Goodson, in "Medical Applications of Controlled Release," supra, vol. 2, pp. 115–138 (1984)). Other controlled-release systems discussed in Langer, 1990, Science 249:1527–1533 may also be used.

5.9 Pharmaceutical Compositions

The present pharmaceutical compositions contain a therapeutically effective amount of one or more compounds, preferably, in purified form, together with a suitable amount of a pharmaceutically acceptable vehicle, so as to provide the form for proper administration to a patient. When administered to a patient, the compounds and pharmaceutically acceptable vehicles are preferably sterile. Water is a preferred vehicle when the compounds are administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995).

For topical administration, compounds may be formulated as solutions, gels, ointments, creams, suspensions, etc. as is well-known in the art. Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In one embodiment, the compounds are formulated in accordance with routine procedures as a pharmaceutical composition adapted for intravenous administration to human beings. Typically, compounds for intravenous administration are solutions in sterile isotonic aqueous buffer. For injection, a compound may be formulated in aqueous solutions, preferably, in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent. Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the compound is administered by infusion, it can be dispensed, for example, with an infusion bottle containing sterile pharmaceutical grade water or saline. When a compound is administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g. polyethylene glycol) oils, alcohols, slightly acidic buffers between pH 4 and pH 6 (e.g., acetate, citrate, ascorbate at between about 5.0 mM to about 50.0 mM), etc. Additionally, flavoring agents, preservatives, coloring agents, bile salts, acylcamitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

A compound may also be formulated in rectal or vaginal pharmaceutical compositions such as suppositories or retention enemas, e.g., containing conventional suppository bases such as cocoa butter or other glycerides.

In addition to the formulations described previously, a compound may also be formulated as a depot preparation. Such long acting formulations may be administered by implantation (for example subcutaneously or intramuscularly) or by intramuscular injection. Thus, for example, a compound may be formulated with suitable polymeric or hydrophobic materials (for example as an emulsion in an acceptable oil) or ion exchange resins, or as sparingly soluble derivatives, for example, as a sparingly soluble salt.

When a compound is acidic, it may be included in any of the above-described formulations as the free acid or a pharmaceutically acceptable salt. Pharmaceutically acceptable salts substantially retain the activity of the free acid, may be prepared by reaction with bases and tend to be more soluble in aqueous and other protic solvents than the corresponding free acid form.

5.10 Doses

A compound and/or pharmaceutical composition thereof, will generally be used in an amount effective to achieve the intended purpose. For use to treat or prevent diseases or disorders characterized by aberrant vascularization compounds and/or pharmaceutical compositions thereof, are administered or applied in a therapeutically effective amount.

The amount of a compound that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In one embodiment, compounds are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

Suitable dosage ranges for oral administration are dependent on the potency of the drug, but are generally about 0.001 mg to about 200 mg of a compound of the invention per kilogram body weight. Dosage ranges may be readily determined by methods known to the artisan of ordinary skill.

Suitable dosage ranges for intravenous (i.v.) administration are about 0.01 mg to about 100 mg per kilogram body weight. Suitable dosage ranges for intranasal administration are generally about 0.01 mg/kg body weight to about 10 mg/kg body weight. Suppositories generally contain about 0.01 milligram to about 50 milligrams of a compound of the invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well-known in the art.

Compounds of the invention are preferably assayed in vitro and in vivo, as described above, for the desired therapeutic or prophylactic activity, prior to use in humans. For example, in vitro assays can be used to determine whether administration of a specific compound or a combination of compounds are preferred for treating cancer. Compounds may also be demonstrated to be effective and safe using animal model systems.

Preferably, a therapeutically effective dose of a compound described herein will provide therapeutic benefit without causing substantial toxicity. Toxicity of compounds may be determined using standard pharmaceutical procedures and may be readily ascertained by the skilled artisan. The dose ratio between toxic and therapeutic effect is the therapeutic index. Compounds will preferably exhibit particularly high therapeutic indices in treating disease and disorders. The dosage of a compound described herein will preferably be within a range of circulating concentrations that include an effective dose with little or no toxicity.

5.11 Combination Therapy

In certain embodiments, the compounds and/or pharmaceutical compositions thereof can be used in combination therapy with at least one other therapeutic agent. The compound and/or pharmaceutical composition thereof and the therapeutic agent can act additively or, more preferably, synergistically. In one embodiment, a compound and/or pharmaceutical composition thereof is administered concurrently with the administration of another therapeutic agent, which may be part of the same pharmaceutical composition or a different pharmaceutical composition. In another embodiment, a pharmaceutical composition is administered prior or subsequent to administration of another therapeutic agent.

In particular, in one preferred embodiment, compounds and/or pharmaceutical compositions thereof can be used in combination therapy with other chemotherapeutic agents (e.g., alkylating agents (e.g., nitrogen mustards (e.g., cyclophosphamide, ifosfamide, mechlorethamine, melphalen, chlorambucil, hexamethylmelamine, thiotepa), alkyl sulfonates (e.g., busulfan), nitrosoureas, triazines), antimetabolites (e.g., folic acid analogs, pyrimidine analogs (e.g., fluorouracil, floxuridine, cytosine arabinoside, etc.), purine analogs (e.g., mercaptopurine, thiogunaine, pentostatin, etc.), natural products (e.g., vinblastine, vincristine, etoposide, tertiposide, dactinomycin, daunorubicin, doxurubicin, bleomycin, mithrmycin, mitomycin C, L-asparaginase, interferon alpha), platinum coordination complexes (e.g., cis-platinum, carboplatin, etc.), mitoxantrone, hydroxyurea, procarbazine, hormones and antagonists (e.g., prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, etc.), anti-angiogenesis agents or inhibitors (e.g., angiostatin, retinoic acids and paclitaxel, estradiol derivatives, thiazolopyrimidine derivatives, etc.), apoptosis-inducing agents (e.g., antisense nucleotides that block oncogenes which inhibit apoptosis, tumor suppressors, TRAIL, TRAIL polypeptide, Fas-associated factor 1, interleukin-1β-converting enzyme, phosphotyrosine inhibitors, RXR retinoid receptor agonists, carbostyril derivatives, etc.) and chelators (penicillamine, zinc, trientine, etc.)).

5.12 Therapeutic Kits

The current invention provides therapeutic kits comprising compounds and/or pharmaceutical compositions of the invention. The therapeutic kits may also contain other compounds (e.g., chemotherapeutic agents, natural products, hormones or antagonists, anti-angiogenesis agents or inhibitors, apoptosis-inducing agents or chelators) and/or pharmaceutical compositions of these other compounds.

Therapeutic kits may have a single containers which contains compounds and/or pharmaceutical compositions thereof with or without other components (e.g., other compounds or pharmaceutical compositions of these other compounds) or may have distinct container for each component. Preferably, therapeutic kits of the invention include a compound and/or a pharmaceutical composition thereof packaged for use in combination with the co-administration of a second compound (preferably, a chemotherapeutic agent, a natural product, a hormone or antagonist, a anti-angiogenesis agent or inhibitor, a apoptosis-inducing agent or a chelator) and/or a pharmaceutical composition thereof. The components of the kit may be pre-complexed or each component may be in a separate distinct container prior to administration to a patient.

The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid.

Preferably, a therapeutic kit will contain apparatus (e.g., one or more needles, syringes, eye droppers, pipette, etc.), which enables administration of the components of the kit.

6. EXAMPLES

The invention is further defined by reference to the following examples, which describe in detail, preparation of compounds of the invention and methods for assaying for biological activity. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

| | |
|---|---|
| AcCN = | acetonitrile |
| Boc = | tert-butyloxycarbonyl |
| CPM = | counts per minute |
| DMF = | N,N-dimethylformamide |
| DMSO = | dimethylsulfoxide |
| Fmoc = | 9-fluorenylmethyloxycarbonyl |
| g = | gram |
| h = | hour |
| HBTU = | O-Benzotriazole, N, N, N, N, tetramethyl uronium hexafluoro phosphate |
| HBSS = | Hank's buffered saline solution |
| HOBT = | N-hydroxybenxotriazole |
| HPLC = | high pressure liquid chromatography |
| L = | liter |
| LC/MS = | liquid chromatography/mass spectroscopy |
| M = | molar |
| min = | minute |
| mL = | milliliter |
| mmol = | millimoles |
| NHS = | N-hydroxysuccinimide |
| NMM = | N-methyl morpholine |
| TFA = | trifluoroacetic acid |
| TIS = | triisopropylsilane |
| TLC = | thin layer chromatography |
| μL = | microliter |
| μM = | micromolar |
| v/v = | volume to volume |

6.1 Example 1

Standard Resin Bound Amino Acid Coupling

Rink Amide AM resin (Novabiochem) was treated with 20% piperidine in DMF (1 mL per 100 mg of resin) for three minutes with agitation and the reaction mixture was filtered and washed once with DMF. This step was repeated an additional two times. The Rink resin was then washed three times with DMF, three times with methanol and three times with dichloromethane. The desired Fmoc protected, tritylated amino acid (4 eq.), HBTU (4 eq.), and HOBt (4 eq.) were dissolved in DMF (1 mL per 100 mg of resin) and added to the above resin, followed by the addition of (NMM) (8 eq.) and the mixture was agitated for 1 hour. The reaction mixture was filtered and the resin was washed three times with DMF, three times with methanol and three times with dichloromethane. This coupling step was repeated until peptide synthesis was complete. The acetylation of the N-terminus was performed either by coupling with Ac-Pro-OH (4 eq.), HBTU (4 eq.), HOBT (4 eq.) and NMM (8 eq.) or by deprotecting the terminal Fmoc group and capping with acetic anhydride (5 eq.) and pyridine (5 eq.). The N-acetylated peptide on Rink Amide AM resin was treated with TFA/TIS/water (95:2.5:2.5, 1 mL per 100 mg of resin) and agitated for 1 hour. The reaction mixture was filtered, the resin was washed once with TFA/TIS/water and three times with dichloromethane. The solvent was removed in vacuo and the resulting residue was triturated three times with ether.

6.2 Example 2

Purification of Peptides

The crude peptide, dissolved in a minimum amount of methanol and water, was purified by preparative reverse phase HPLC (Beckman) with a Phenomenex Synergi hydro-reverse phase C18 column (250 mm×21.2 mm). The peptide was eluted using a gradient from 0–50% B over 15 min with a flow rate of 20 mL/min, where solvent A was water containing 0.1% TFA and solvent B was acetonitrile containing 0.1% TFA. Detection was at 220 nm. Fractions >95% pure by analytical HPLC analysis (Phenomenex hydro reverse phase (250 mm×4.6 mm) using gradient 6–66%) were combined, concentrated to a volume of about 2–4 ml by evaporation in vacuo and lyophilized. Samples were redissolved in water and transferred to a tared 2 dram vial and lyophilized a second time. A shoulder was often observed for these peptides and was presumed to be due to a conformer.

6.3 Example 3

Purification of Peptides

The crude peptide dissolved in a minimum amount of methanol and water was loaded onto a prep column: Phenomenex Synergi hydro-RP C 18, (250 mm×21.2 mm). The peptide was eluted using a gradient from 0–50% AcN/0.1% TFA and milliQ $H_2O$/0.1% TFA. Fractions greater than 95% pure by analytical HPLC analysis (Phenomenex hydro RP 250 mm×4.6 mm using gradient 6–66% AcN/0.1% TFA and milliQ $H_2O$/0.1% TFA) were combined, concentrated to a volume of about 2–4 ml by rotary evaporation, and lyophilized. Samples were redissolved in water in a tared 2 dram vial and lyophilized a second time.

6.4 Example 4

Standard Resin Bound Amino Acid Coupling

Rink Amide AM resin (Novabiochem) was treated with 20% piperidine in DMF (1 mL per 100 mg of resin) for three minutes with nitrogen agitation or vibration and the reaction mixture was filtered and washed with DMF once. This step was repeated an additional two times. The resin was washed three times with DMF, three times with methanol and three times with dichloromethane. The desired Fmoc protected amino acid (3 eq.), HBTU (4 eq.), and HOBt (7 eq.) were dissolved in DMF (1 mL per 100 mg of resin) and added to the above resin, followed by the addition of NMM (8 eq.) was and the mixture was agitated for 1 hour. The reaction mixture was filtered and the resin was washed three times with DMF, three times with methanol and three times with dichloromethane. The amino acid coupling step was then repeated. The acetylation of the N-terminus was performed either by coupling with Ac-Pro-OH (3 eq.), HBTU (4 eq.), HOBT (7 eq.) and NMM (8 eq.) or by deprotecting the terminal Fmoc group and capping with acetic anhydride (5 eq.) and pyridine (5 eq.). The N-acetylated peptide on Rink Amide AM resin was treated with TFA/TIS/water (95:2.5:2.5, 1 mL per 100 mg of resin) and agitated with nitrogen or vibration for 1 hour. The reaction mixture was filtered, the resin was washed once with TFA/TIS/water and three times with dichloromethane. The solvent was removed in vacuo and the resulting residue was triturated three times with ether.

6.5 Example 5

Peptide Acylation

The appropriate N-acyl peptide amide was suspended in DMF (0.05M). NMM (2.0 eq.) was added followed by the acyl chloride (4.0 eq.). The suspension became homogeneous after about 10 minutes. Analytical HPLC indicated loss of starting material after ~1 hour. The mixture was concentrated in vacuo, dissolved in water/methanol (heated if necessary for dissolution) and purified by preparative HPLC (see standard purification procedures in Examples 2 and 3).

6.6 Example 6

Peptide Alkylation

The appropriate N-acyl peptide amide was suspended in DMF (0.05 M). Cesium carbonate (2.0 eq.) was added followed by alkyl bromide (1.0 eq.). Once the reaction was complete, as judged by analytical HPLC, the mixture was concentrated in vacuo, dissolved in 1 N HCl and purified by preparative HPLC (see standard purification procedures in Examples 2 and 3).

6.7 Example 7

Disulfide Formation

The appropriate N-acyl peptide amide was suspended in DMF (0.05 M). The commercially available thiosulfate (1.2 eq.) was added. Once the reaction was complete, as judged by analytical HPLC, the mixture was concentrated in vacuo, dissolved in water/methanol and purified by preparative HPLC (see standard purification procedures in Examples 2 and 3).

6.8 Example 8

Thiocarbonate Formation

The appropriate N-acetyl peptide amide was dissolved in 5% aqueous $NaHCO_3$ (0.05 M) and cooled in an ice water bath. The appropriate chloroformate (1.2 eq.) was added. After 1 h, the reaction mixture was removed from the ice bath and stirred for an additional 2 hrs at room temperature (a precipitate formed). The reaction was then treated with 1 N HCl until pH<4 (paper) and directly purified by preparative HPLC (see standard purification procedures in Examples 2 and 3).

6.9 Example 9

Standard Resin Bound Amino Acid Coupling

The appropriate Rink Amide AM resin-bound Fmoc amino acid was added to a Buchner funnel with a side arm and treated with 20% piperidine in DMF (1 mL per 100 mg of resin) for five minutes with nitrogen agitation. The reaction mixture was filtered and this step was repeated. The resin was washed three times with DMF and three times with dichloromethane. DMF (1 mL per 100 mg of resin), the desired Fmoc protected amino acid (sidechains were protected with trityl) (4 eq.), HBTU (4 eq.), and HOBt (4 eq.) were added to the resin. N-methylmorpholine (8 eq.) was added and the mixture agitated with nitrogen for 1 hour. The reaction mixture was filtered and the resin was washed three times with DMF and three times with dichloromethane. The final coupling was performed with Ac-Pro-OH to provide acetyl capped peptides. The peptides were cleaved from the resin by treatment with TFA, TIS, $H_2O$ (95:2.5:2.5; 1–5 mL per 100 mg of resin) with $N_2$ agitation for 1 h. The reaction mixture was filtered and the resin was rinsed with a small volume of TFA. The solution was concentrated in vacuo and the resulting residue was triturated 3 times with ethyl ether.

6.10 Example 10

Acetyl-Pro-His-Ser-Cys(benzyl)-Asn-$NH_2$
(SEQ ID NO: 3)

This compound was prepared according to procedures of Examples 1 and 2 giving the title compound (74 mg, 97%) as a fine white powder. The NMR data indicated a mixture of two species in a ratio of about 80:20: $^1H$ NMR (300 MHz, DMSO-$d_6$) δ 8.96, 8.95 (d, d, 1 H, J=1.2 Hz), 7.90–8.45 (m, 4 H), 7.23–7.39 (m, 7 H), 7.13 (s, 1 H), 7.01 (s, 1 H), 6.91 (s, 1 H), 5.08 (bs, 1 H), 4.60–4.80 (m, 1 H), 4.25–4.53 (m, 5 H), 3.77 (s, 2 H), 3.64–3.66 (m, 2 H), 3.15–3.20 (m, 1 H), 2.93–3.01 (m, 1 H), 2.78–2.84 (dd, 1 H, J=5.4, 14.1 Hz), 2.56–2.67 (m, 1 H), 2.38–2.49 (dd, 1 H, J=7.5, 15.6 Hz), 2.00 (s, 3 H), 1.84 (m, 3 H); $^{13}C$ NMR (75 MHz, DMSO-$d_6$) δ 172.57, 171.8, 171.5, 170.2, 169.7, 169.6, 169.2, 138.2, 133.6, 129.4, 128.9, 128.3, 126.8, 117.0, 61.6, 59.3, 55.2, 52.7, 51.2, 49.8, 47.8, 36.8, 35.3, 32.8, 29.3, 24.3, 22.2, 21.8; MS m/z $(C_{30}H_{41}N_9O_8S+H)^+$ 688.8; Anal. Calcd for $C_{30}H_{41}N_9O_8S$: N, 18.33. Found: N, 14.52 (peptide content: 79%).

6.11 Example 11

Acetyl-Pro-His-Ser-Cys(4-methyl-benzyl)-Asn-$NH_2$
(SEQ ID NO: 4)

This compound was prepared according to the procedure of Examples 1 and 2 giving the title compound (87 mg, 99%) as a fine white powder. The NMR data indicated a mixture of two species in a ratio of about 80:20: $^1H$ NMR (300 MHz, DMSO-$d_6$) δ 8.96 (m, 1 H), 7.90–8.45 (m, 4 H), 6.91–7.09 (m, 7 H), 7.00 (s, 1 H), 6.91 (s, 1 H), 5.10 (bs, 1 H), 4.60–4.75 (m, 1 H), 4.46–4.50 (m, 2 H), 4.27–4.40 (m, 2 H), 3.72 (s, 2 H), 3.64 (m, 2 H), 3.50 (m, 2 H), 3.15–3.21 (m, 1 H), 2.93–3.02 (m, 1 H), 2.76–2.82 (m, 1 H), 2.56–2.65 (m, 1 H), 2.37–2.45 (m, 1 H), 2.62 (s, 3 H), 1.99 (s, 3 H), 1.73–1.86 (m, 3 H); $^{13}C$ NMR (75 MHz, DMSO-$d_6$) δ 172.5, 171.8, 171.5, 170.1, 169.6, 169.5, 169.1, 135.8, 135.0, 133.6, 129.3, 128.8, 128.7, 116.8, 61.6, 59.2, 55.1, 52.6, 51.2, 49.7, 47.7, 36.8, 34.9, 32.7, 29.2, 24.2, 22.1, 21.8, 20.6; MS m/z $(C_{31}H_{43}N_9O_8S+H)^+$ 703.0; Anal. Calcd for $C_{31}H_{43}N_9O_8S$: N, 17.96. Found: N, 14.21 (peptide content: 79%).

6.12 Example 12

Acetyl-Pro-His-Ser-Met(O)-Asn-$NH_2$
(SEQ ID NO: 5)

This compound was prepared according to the procedures of Examples 1 and 2 to provide the title compound (30 mg, 29%) as a fine white powder. The NMR data indicated a mixture of two species in a ratio of about 80:20: $^1H$ NMR (300 MHz, DMSO-$d_6$) δ 8.97 (s, 1 H), 7.95–8.44 (m, 5 H), 7.40 (s, 1 H), 7.35 (s, 1 H), 7.09 (s, 2 H), 6.91 (s, 1 H), 4.59–4.77 (m, 1 H), 4.25–4.49 (m, 4 H), 3.45–3.54 (m, 1 H), 3.26–3.37 (m, 1 H), 3.14–3.21 (m, 1 H), 2.95–3.03 (m, 1 H), 2.64–2.83 (m, 2 H), 2.52 (m, 3 H), 2.38–2.45 (m, 1 H), 2.00 (s, 3 H), 1.84–2.06 (m, 2 H), 1.68–1.83 (m, 4 H); $^{13}C$ NMR (75 MHz, DMSO-$d_6$) δ 172.7, 171.8, 171.5, 170.3, 170.1, 169.7, 169.2, 133.6, 129.3, 116.9, 61.4, 59.3, 55.1, 52.0, 51.2, 49.7, 49.0, 47.8, 37.8, 36.8, 29.3, 26.4, 24.9, 24.3, 22.3; MS m/z $(C_{25}H_{39}N_9O_9S+H)^+$ 642.9; Anal. Calcd for $C_{25}H_{39}N_9O_9S$: N, 19.64. Found: N, 14.79 (peptide content: 75%).

6.13 Example 13

Acetyl-Pro-His-Ser-Met($O_2$)-Asn-$NH_2$
(SEQ ID NO: 6)

This compound was prepared according to the procedure of Examples 1 and 2 to give the title compound (92.5 mg, 88%) as a fine white powder. The NMR data indicated a mixture of two species in a ratio of about 80:20: $^1H$ NMR (300 MHz, DMSO-d6) δ 8.68 (d, 1 H, J=1.4 Hz), 7.38 (m, 1 H), 4.73–4.86 (m, 2 H), 4.65 (dd, 1 H, J=5.3, 3.5 Hz), 4.50 (t, 1 H, J=5.4 Hz), 4.41 (dd, 1 H, J=5.1, 3.6 Hz), 3.93 (t, 2 H, J=5.7 Hz), 3.68 (t, 2 H, J=7.0 Hz), 3.37–3.42 (m, 3 H), 3.21–3.29 (m, 1 H), 3.18 (s, 3 H), 2.75–2.94 (m, 2 H), 2.42–2.47 (m, 1 H), 2.24–2.35 (m, 2 H), 2.17 (s, 3 H), 1.86–2.04 (m, 4 H); $^{13}C$ NMR (75 MHz, DMSO-$d_6$) δ 174.2, 174.1, 173.9, 172.7, 171.3, 171.2, 171.1, 132.9, 127.9, 116.7, 60.4, 59.6, 55.1, 51.6, 51.4, 49.8, 49.5, 48.2, 39.2, 35.7, 29.3, 25.5, 23.7, 23.1, 20.9; MS m/z $(C_{25}H_{39}N_9O_{10}S+H)^+$ 658.7; Anal. calcd for $C_{25}H_{39}N_9O_{10}S$: N, 19.17. Found: N, 14.80 (peptide content, 77%).

6.14 Example 14

Acetyl-His-Ser-Cys(methyl)-$NH_2$

This compound was prepared according to the procedure of Examples 1 and 2 giving the title compound (121.6 mg, 61%) as a fine white powder: $^1H$ NMR (300 MHz, DMSO-$d_6$) δ 14.1 (bs, 1 H), 8.96 (s, 1 H), 8.18–8.21 (d, 2 H, J=8.13 Hz), 8.10 (d, 1 H, J=6.8 Hz), 7.42 (s, 1 H), 7.37 (bs, 1 H), 7.25 (s, 1 H), 5.19 (bs, 1 H), 4.65–4.72 (m, 1 H), 4.32–4.42 (m, 2 H), 3.57–3.71 (m, 2 H), 2.68–3.13 (m, 4 H), 2.09 (s, 3 H), 1.85 (s, 3 H); $^{13}$C NMR (75 MHz, DMSO-d$_6$) δ 171.9, 170.1, 169.9, 169.5, 129.3, 116.8, 61.5, 55.0, 52.4, 51.4, 35.3, 27.1, 22.4, 15.2; MS m/z (C$_{15}$H$_{24}$N$_6$O$_5$S+H)$^+$ 401.5. Anal. calcd for C$_{15}$H$_{24}$N$_6$O$_5$S: N, 20.99. Found: N, 15.23 (peptide content, 72%).

6.15 Example 15

Acetyl-Cys(methyl)-NH$_2$

This compound was prepared according to the procedure of Examples 1 and 2 giving the title compound (9.7 mg, 26%) as a fine white powder: $^1$H NMR (300 MHz, D$_2$O) δ 4.55 (dd, 1 H, J=4.9, 3.4 Hz), 2.90–3.08 (m, 1 H), 2.20 (s, 3 H), 2.12 (s, 3 H); $^{13}$C NMR (75 MHz, D$_2$O) δ 174.8, 173.9, 52.0, 34.4, 21.2, 14.1; MS m/z (C$_6$H$_{12}$N$_2$O$_2$S+Na)$^+$ 199.3; Anal. calcd for C$_6$H$_{12}$N$_2$O$_2$S: N, 15.90. Found: 13.04 (peptide content: 82%).

6.16 Example 16

Acetyl-Pro-His-Ser-Cys(methyl)-NH$_2$
(SEQ ID NO: 7)

This compound was prepared according to the procedures of Examples 1 and 2 giving the title compounds (106.1 mg, 43%) as a fine white powder: $^1$H NMR (300 MHz, DMSO-d$_6$) δ 8.96–8.97 (m, 1 H), 7.85–8.46 (m, 3 H), 7.34–7.41 (m, 2 H), 7.24 (s, 1 H), 4.59–4.78 (m, 1 H), 4.25–4.42 (m, 3 H)3.64–3.69 (m, 1 H), 3.15–3.21 (m, 1 H), 2.93–3.02 (m, 1 H), 2.85 (dd, 1 H, J=5.0, 13.7 Hz), 2.65–2.72 (m, 1 H), 2.07 (s, 3 H), 2.00 (s, 3 H), 1.67–1.85 (m, 4 H); $^{13}$C NMR (75 MHz, DMSO-d$_6$) δ 171.9, 171.8, 169.8, 169.7, 169.1, 129.3, 116.6, 61.6, 60.2, 59.2, 55.0, 52.3, 51.2, 47.7, 38.6, 35.4, 29.3, 24.3, 22.3, 15.2; MS m/z (C$_{20}$H$_{31}$N$_7$O$_6$S+H)$^+$ 498.6; Anal. calcd for C$_{20}$H$_{31}$N$_7$O$_6$S: N, 19.71. Found: N, 14.79 (peptide content: 75%).

6.17 Example 17

Acetyl-Ser-Cys(methyl)-NH$_2$

This compound was prepared according to the procedure of Examples 1 and 2 giving the title compound (32.1 mg, 49%) as a fine white powder: $^1$H NMR (300 MHz, DMSO-d$_6$) δ 8.03 (d, 1 H, J=8.2 Hz), 7.98 (1 H, J=7.6 Hz), 7.35 (s, 1 H), 7.21 (s, 1 H), 5.03 (bs, 1 H), 4.27–4.38 (m, 2 H), 3.49–3.61 (m, 2 H), 2.85 (dd, 1 H, J=4.9, 13.7 Hz), 2.69 (dd, 1 H, J=8.5, 13.7 Hz), 2.06 (s, 3 H), 1.87 (s, 3 H); $^{13}$C NMR (75 MHz, DMSO-d$_6$) δ 172.0, 170.2, 169.5, 61.7, 55.0, 52.2, 35.3, 22.5, 15.1; MS m/z (C$_9$H$_{17}$N$_3$O$_4$S+Na)$^+$ 286.2; Anal. calcd for C$_9$H$_{17}$N$_3$O$_4$S: N, 15.96. Found: N, 15.31 (peptide content: 96%).

6.18 Example 18

Acetyl-Pro-His-Ser-Cys(4-MeO-Phenyl)-Asn-NH$_2$
(SEQ ID NO: 8)

This compound was prepared according to the procedure of Examples 1 and 2 except with the following modification: the monomer Fmoc-Cys(4-MeO-phenyl) was synthesized from Fmoc-Cys(4-MeO-Benzyl)-OH in 2 steps. The title compound was isolated as a fine white powder (28.0 mg, 50%): $^1$H NMR (300 MHz, DMSO-d$_6$) δ 8.90–8.92 (m, 1H), 8.42–8.51 (m, 1 H), 8.30 (d, 1 H, J=1 Hz), 8.09 (d, 1 H, J=1 H), 7.88 (m, 1 H), 7.33–7.39 (m, 4 H), 712 (s, 1 H), 6.98 (s, 1 H), 6.90 (m, 2 H), 6.51 (bs, 1 H), 5.04–5.19 (m, 1 H), 4.58–4.82 (m, 2 H), 4.23–4.47 (m, 4 H), 3.75 (s, 3 H), 3.59–3.71 (m, 2 H), 2.95–3.03 (m, 2 H), 2.36–2.44 (m, 1 H), 2.00 (s, 3 H), 167–1.95 (m, 4 H); $^{13}$C NMR (75 MHz, DMSO-d$_6$) δ 172.5, 171.9, 171.6, 170.3, 169.8, 169.4, 169.1, 158.7, 133.1, 129.5, 125.0, 116.9, 114.8, 61.6, 59.3, 55.2, 52.6, 51.3, 49.8, 47.8, 36.9, 36.7, 29.3, 26.5, 24.3, 22.2; MS m/z (C$_{30}$H$_{41}$N$_9$O$_9$S+H)$^+$ 704.8; Anal. calcd for C$_{30}$H$_{41}$N$_9$O$_9$S: N, 17.91. Found: N, 13.11 (peptide content: 73%).

6.19 Example 19

Acetyl-Pro-His-Ser-NH$_2$

This compound was prepared according to the procedure of Examples 1 and 2 giving the title compound (37.7 mg, 50%) as a fine white powder: $^1$H NMR (300 MHz, DMSO-d$_6$) δ 8.96 (d, 1 H, J=1.3 Hz), 8.24–8.43 (m, 1 H), 7.77–7.82 (m, 1 H), 7.37–7.42 (m, 2 H), 7.19 (m, 1 H), 4.57–4.76 (m, 2 H), 4.15–4.34 (m, 2 H), 3.63–3.64 (m, 2 H), 3.14–3.24 (m, 2 H), 2.95–3.05 (m, 1 H), 2.01 (s, 3 H), 1.67–1.91 (m, 4 H); $^{13}$C NMR (75 MHz, DMSO-d$_6$) δ 171.9, 171.8, 169.5, 169.2, 129.3, 116.9, 61.5, 59.3, 55.1, 51.4, 47.8, 29.3, 26.4, 24.3, 22.2; MS m/z (C$_{16}$H$_{24}$N$_6$O$_5$+H)$^+$ 381.4; Anal. calcd for C$_{16}$H$_{24}$N$_6$O$_5$: N, 22.09. Found: N, 14.50 (peptide content: 66%)

6.20 Example 20

Ac-Pro-His-Ser-Cys(pMeOBzl)-Asn-NH$_2$
(SEQ ID NO: 9)

This compound was prepared according to the procedure of Examples 1 and 2 and afforded 79.1 mg (46%) of the title compound as a white powder and as a mixture of two compounds in a ratio of 67:33: $^1$H NMR (300 MHz, DMSO-d$_6$) δ 8.97 (s, 1H), 8.46–8.19 (m, 3H), 8.00–7.90 (m, 1H), 7.39 (s, 1H), 7.35 (s, 1H), 7.25–7.21 (m, 2H), 7.13 (s, 1H), 7.01 (s, 1H), 6.91 (s, 1H), 6.87–6.82 (m, 2H), 4.79–4.25 (m, 17H, overlapping with water peak), 3.72–3.58 (m, 7H), 3.57–3.46 (m, 2H), 3.40–3.24 (m, 1H), 3.23–3.13 (m, 1H), 3.05–2.94 (m, 1H), 2.84–2.75 (m, 1H), 2.66–2.37 (m, 2H, overlapping with DMSO peak), 2.00 (s, 3H), 1.88–1.65 (m, 4H); $^{13}$C NMR (75 MHz, DMSO-d6) δ 172.5, 172.0, 171.8, 171.5, 170.1, 169.7, 169.64, 169.61, 169.56, 169.1, 168.5, 158.3, 158.1, 157.8, 133.8, 133.6, 130.0, 129.9, 129.4, 129.3, 116.9, 113.7, 61.6, 59.2, 55.1, 54.9, 52.6, 51.2, 49.7, 47.7, 36.8, 34.6, 32.7, 31.5, 29.2, 26.4, 24.3, 22.24, 22.17, 21.8; ES MS m/z (M+H)$^+$ 718.8. Anal. Calcd for C$_{31}$H$_{43}$N$_9$O$_9$S: N, 17.56. Found: N, 13.00 (peptide content: 74%).

6.21 Example 21

Ac-Pro-His-Ser-Cys(Ph)-Asn-NH$_2$ (SEQ ID NO: 10)

This compound was prepared according to the procedures of Examples 1 and 2 with the exception that the coupling of Fmoc-Cys(Ph)-OH to the resin bound tritylated asparagine was performed using half the equivalents of the reagents given in Example 1. The title compound (36.9 mg, 29%) was isolated as a white powder and as a mixture of two compounds in a ratio of 65:35: $^1$H NMR (300 MHz, DMSO-d6) δ 8.96 (s, 1H), 8.55–8.42 (m, 1H), 8.31 (d, J=8.3 Hz, 1H), 8.17 (d, J=7.9 Hz, 1H), 7.98–7.81 (m, 1H), 7.40–7.28 (m, 6H), 7.24–7.17 (m, 1H), 7.12 (s, 1H), 7.00 (s, 1H), 6.91 (s, 1H), 4.79–4.60 (m, 2H), 4.48–4.25 (m, 6H, overlapping with water peak), 3.71–3.46 (m, 4H), 3.42–3.28 (m, 2H), 3.23–3.08 (m, 2H), 3.05–2.93 (m, 1H), 2.56–2.36 (m, 2H, overlapping with DMSO peak), 2.00 (s, 3H), 1.89–1.65 (m, 4H); $^{13}$C NMR (75 MHz, DMSO-d6) δ 172.4, 172.0, 171.8, 171.5, 170.3, 169.74, 169.66, 169.2, 169.15, 169.08, 168.5, 158.1, 157.7, 135.5, 133.8, 133.5, 129.4, 129.3, 129.0, 128.6, 126.0, 116.8, 61.5, 60.2, 59.2, 55.1, 54.8, 52.5, 51.24, 51.17, 49.7, 47.7, 36.7, 34.6, 31.5, 29.2, 26.8, 26.4, 24.2, 22.23, 22.16, 21.7; ES MS m/z (M+H)$^+$ 674.7. Anal. Calcd for $C_{29}H_{39}N_9O8S$: N, 18.71. Found: N, 13.52 (peptide content: 72%).

6.22 Example 22

Acetyl-Pro-His-Ser-Cys(S-tBu)-Asn-NH$_2$ (SEQ ID NO: 11)

This compound was prepared according to the procedure of Examples 1 and 3 giving the title compound as a fine white powder. The NMR data indicated a mixture of two species in approximately 2:1 ratio: $^1$H NMR (300 MHz, MeOD-d$_4$) major conformer δ 8.77 (d, 1 H, J=1.4), 7.41 (br, 1 H), 4.77–4.57 (m, 3 H), 4.46–4.36 (m, 2 H), 3.95–3.80 (m, 2 H), 3.70–3.57 (m, 2 H), 3.39–3.14 (m, 2 H), 3.07–2.97 (m, 1 H), 2.79–2.65 (m, 3 H), 2.26–1.86 (m, 4 H), 2.21 (s, 3 H), 1.35 (s, 9 H) for the minor conformer 8.78 (d, J=1.4), 1.34 (s, 9); $^{13}$C NMR (75 MHz, MeOD-d$_6$) δ 175.0, 173.3, 172.7 (2 C), 172.2, 172.0 (2 C), 135.0, 130.8, 119.1, 62.9, 61.6, 57.5, 57.2, 53.5, 51.7, 42.3, 42.2, 37.7 (2 C), 31.1, 30.4 (3 C), 28.0, 26.0, 22.5 ; MS m/z $(C_{27}H_{43}N_9O_8S_2+H)^+$ 686.8; Anal. calcd for $C_{27}H_{43}N_9O_8S_2$: N, 18.38. Found : N, 13.87 (peptide content: 76%).

6.23 Example 23

Acetyl-Pro-His-Ser-Cys(tBu)-Asn-NH$_2$ (SEQ ID NO: 12)

This compound was prepared according to the procedure of Examples 1 and 3 giving the title compound (18.5 mg, 23%) as a fine white powder. The NMR data indicated a mixture of two species: $^1$H NMR (300 MHz, MeOD-d$_4$) major conformer δ 8.78 (br s, 1 H), 7.42 (br s, 1 H), 4.75–4.71 (m, 1 H), 4.54–4.34 (m, 4), 3.90 (dd, 1 H, J=11, 6), 3.82 (dd, 1 H, J=11, 6), 3.71–3.57 (m, 2 H), 3.36 (dd, 1 H, J=15, 5), 3.17 (dd, 1 H, J=15, 5), 3.05 (dd, 1 H, J=11, 6), 2.93 (dd, 1 H, J=11, 6), 2.81 (m, 2 H), 2.25–1.86 (m, 4 H), 2.11 (s, 3 H), 1.33 (s, 9 H), data for the minor conformer 2.01 (s, 3 H), 1.30 (s, 9 H); $^{13}$C NMR (75 MHz, MeOD-d$_6$) δ 175.5, 175.3, 175.0, 173.0, 172.7, 172.4, 172.0, 135.0, 62.9, 61.6, 57.1, 55.8, 53.5, 51.6, 49.8, 43.8, 37.7, 31.3 (3 C), 30.8, 27.9, 26.0, 24.3, 22.5; MS m/z $(C_{27}H_{43}N_9O_8S+H)^+$ 654.7; Anal. calcd for $C_{27}H_{43}N_9O_8S$: N, 19.28. Found: N, 16.25 (peptide content: 73%).

6.24 Example 24

Ac-Pro-Cys(SMe)-Asn-NH$_2$

This compound was prepared according to the procedure of Examples 2 and 4 starting from Fmoc-Asn-AM resin (SMO-072-054, 200 mg, 0.41 mmol/g), to give 13 mg (18.5 μmole, 22.5%) of the final product as a fine white powder. The NMR data indicated a mixture of two species in a ratio of about 2:1: $^1$H NMR (300 MHz, D$_2$O) δ 4.78–4.72 (m, 1H), 4.66–4.56 (m, 1H), 4.49–4.45 (m, 1H), 3.73–3.67 (m, 2H), 3.07–3.01 (m, 1H), 2.96–2.78 (m, 3H), 2.40–2.28 (m, 1H), 2.19 (d, 3H), 2.17 (s, 3H), 2.08–1.98 (m, 3H); $^{13}$C NMR (75 MHz, D$_2$O) δ 177.4(major), 177.4(minor), 177.1, 175.9, 174.9, 62.7, 55.4, 52.9, 51.3, 38.7, 36.8, 34.4, 32.5, 26.9, 24.0(major), 24.0(minor), 17.2(major), 17.1(minor); MS m/z $(C_{15}H_{25}N_5O_5S+H)^+$ 704; Anal. calcd for $C_{15}H_{25}N_5O_5S$: N, 18.08. Found: N, 13.56 (peptide content: 75.0%).

6.25 Example 25

Ac-His-His-Cys(SMe)-Asn-NH$_2$ (SEQ ID NO: 13)

This compound was prepared according to the procedure of Examples 2 and 4 starting from Fmoc-Asn-AM resin (200 mg, 0.41 mmol/g), to give 23 mg (40.8 μmole, 49.7%) of the final product as a fine white powder: $^1$H NMR (300 MHz, D$_2$O) δ 8.68–8.67 (m, 1H), 7.32 (s, 2H), 4.78–4.72 (m, 2H), 4.70–4.65 (dd, J=8.82, 5.91 Hz, 1H), 4.60–4.55 (dd, J=7.92, 6.18 Hz, 1H), 3.36–3.19 (m, 2H), 3.16–3.11 (m, 1H), 3.04–2.99 (m, 2H), 2.97–2.77 (m, 2H), 2.17 (d, 3H), 2.00 (s, 3H); $^{13}$C NMR (75 MHz, D$_2$O) δ 176.0, 175.7, 175.2, 173.1, 173.0, 172.5, 134.8, 134.7, 129.7, 129.5, 118.6, 118.4, 53.9, 53.6, 53.5, 51.6, 37.4, 35.9, 27.5, 27.4, 22.8, 15.9; MS m/z $(C_{22}H_{32}N_{10}O_6S+H)^+$ 565; Anal. calcd for $C_{22}H_{32}N_{10}O_6S$: N, 24.81. Found: N, 14.74 (peptide content: 59.4%).

6.26 Example 26

Ac-His-Ser-Cys(SMe)-Asn-NH$_2$ (SEQ ID NO: 14)

This compound was prepared according to the procedure of Examples 2 and 4 from Fmoc-Asn-AM resin (200 mg, 0.41 mmol/g), giving 14.1 mg (27.4 μmole, 33.4%) of the final product as a fine white powder: $^1$H NMR (300 MHz, D$_2$O) δ 8.67 (d, J=1.32 Hz, 1H), 7.36 (s, 1H), 4.78–4.72 (m, 2H), 4.64–4.60 (dd, J=7.71, 6.03 Hz, 1H), 4.55 (t, J=5.49 Hz, 1H), 3.98–3.85 (m, 2H), 3.34 (dd, J=15.51, 5.97 Hz, 1H), 3.19 (dd, J=15.57, 8.37 Hz, 1H), 3.04 (dd, J=13.98, 6.00 Hz, 1H), 2.96–2.75 (m, 2H), 2.18 (s, 3H), 2.05 (s, 3H); $^{13}$C NMR (75 MHz, D$_2$O) δ 176.0, 175.7, 175.4, 173.2 (2C), 173.0, 134.8, 129.7, 118.5, 62.3, 56.6, 54.2, 53.7, 51.6, 37.5, 35.8, 27.7, 23.0, 16.0; MS m/z $(C_{19}H_{30}N_8O_7S+H)^+$ 515; Anal. calcd for $C_{19}H_{30}N_8O_7S$: N, 21.78. Found: N, 14.53 (peptide content: 66.7%).

6.27 Example 27

Ac-Ser-Cys(SMe)-Asn-NH$_2$

This compound was prepared according to the procedure of Examples 2 and 4 starting from Fmoc-Asn-AM resin (200 mg, 0.41 mmol/g), giving 6.5 mg (17.2 μmole, 21.0%) of the final product as a fine white powder: $^1$H NMR (300 MHz, D$_2$O) δ 4.78–4.74 (dd, J=8.22, 5.61 Hz, 1H), 4.66–4.62 (dd, J=7.74, 6.18 Hz, 1H), 4.52 (t, J=5.61 Hz, 1H), 3.97–3.82 (m, 2H), 3.09–2.76 (m, 4H), 2.19 (s, 3H), 2.13 (s, 3H); $^{13}$C NMR (75 MHz, D$_2$O) δ 176.0, 175.8, 175.7, 173.5, 173.4, 62.3, 56.8, 54.2, 51.6, 37.5, 35.7, 23.0, 16.0; MS m/z $(C_{13}H_{23}N_5O_6S+Na)^+$ 400; Anal. calcd for $Cl_3H_{23}N_5O_6S$: N, 18.56. Found: N, 15.96 (peptide content: 86.0%).

6.28 Example 28

Ac-Cys(SMe)-Asn-NH$_2$

This compound was prepared according to the procedure of Examples 2 and 4 starting from Fmoc-Asn-AM resin (SMO-072-054, 200 mg, 0.41 mmol/g), giving 8.9 mg (30.7 μmole, 37.4%) of the final product WHY-36 as a fine white powder: $^1$H NMR (300 MHz, D$_2$O) δ 4.79–4.73 (m, 1H), 4.58–4.54 (dd, J=7.98, 6.60 Hz, 1H), 3.05–2.78 (dd, J=14.01, 6.09 Hz, 4H), 2.19 (s, 3H), 2.11 (s, 3H); $^{13}$C NMR (75 MHz, D$_2$O) δ 176.0, 175.9, 175.8, 173.8, 54.3, 51.6, 37.4, 35.8, 23.0, 16.0; MS m/z (C$_{10}$H$_{18}$N$_4$O$_4$S+Na)$^+$ 313; Anal. calcd for C$_{10}$H$_{18}$N$_4$O$_4$S: N, 19.30. Found: N, 16.8 (peptide content: 87.4%).

6.29 Example 29

Ac-Pro-His-Ser-Cys(SO$_2$Bn)-Asn-NH$_2$
(SEQ ID NO: 15)

10 mg of the compound of Example 11 (14.5 µmole) was dissolved in 2 mL of formic acid (96%), 0.4 mL of H$_2$O$_2$ (30% in H$_2$O) was added at room temperature and the mixture was stirred overnight. The solvent were removed in vacuo and the resulting white solid was purified according to the procedure of Example 2 to give 7.1 mg (9.87 µmole, 68%) of the desired sulfone WHY-37 as a fine white powder. The NMR data indicated a mixture of two species in a ratio of about 5:1: $^1$H NMR (300 MHz, D$_2$O) δ 8.66 (d, J=1.35 Hz, 1H, minor), 8.62 (d, J=1.38 Hz, 1H, major), 7.55–7.50 (m, 4H), 7.38 (s, 1H, minor), 7.34 (s, 1H, major), 5.12–5.07 (dd, J=8.52, 4.41 Hz, 1H), 4.90–4.83 (m, 1H), 4.77–4.72 (m, 1H), 4.67 (s, 2H), 4.52 (t, J=5.49 Hz, 1H), 4.41–4.37 (dd, J=8.82, 5.13 Hz, 1H), 3.76–3.64 (m, 3 H), 3.76–3.64 (m, 3H), 3.40–3.17 (m, 2H), 2.93–2.74 (m, 2H), 2.31–2.23 (m, 1H), 2.15 (s, 3H), 2.05–1.84 (m, 4H); $^{13}$C NMR (75 MHz, D$_2$O) δ 175.9, 175.7, 174.5, 172.8, 172.7, 170.9, 164.5, 134.7, 132.5, 130.8, 130.4, 129.7, 127.5, 118.5, 62.2, 61.4, 61.0, 56.7, 53.4, 52.7, 51.8, 50.0, 49.3, 37.4, 31.1, 27.4, 25.6, 22.7; MS m/z (C$_{30}$H$_{41}$N$_9$O$_{10}$S+H)$^+$ 720; Anal. calcd for C$_{30}$H$_{41}$N$_9$O$_{10}$S: N, 17.51. Found: N, 10.72 (peptide content: 61.2%).

6.30 Example 30

Ac-Pro-His-Ser-HoCys(SO$_2$Ph)-Asn-NH$_2$
(SEQ ID NO: 16)

This compound was prepared according to the procedure of Example 29 starting from 10 mg (14.5 µmole) of the sulfide precursor, giving 3.3 mg (4.58 µmole, 31.6%) of the desired sulfone as a fine white powder. The NMR data indicated a mixture of two species in a ratio of about 6:1: $^1$H NMR (300 MHz, D$_2$O) δ 8.71 (d, J=1.41 Hz, 1H, minor), 8.68 (d, J=1.41 Hz, 1H, major), 8.02–7.99 (m, 2H), 7.90–7.85 (m, 1H), 7.78–7.73 (m, 2H), 7.40 (bs, 1H, minor), 7.37 (bs, 1H, major), 4.87–4.82 (m, 1H), 4.73–4.68 (m, 1H), 4.60–4.55 (dd, J=8.85, 5.10 Hz, 1H), 4.48–4.44 (m, 1H), 4.40–4.35 (dd, J=8.70, 5.16 Hz, 1H), 3.96–3.85 (m, 2H), 3.69 (t, J=6.66 Hz, 2 H), 3.51 (t, J=7.38 Hz, 2H), 3.41–3.34 (dd, J=15.45, 5.55 Hz, 1H), 3.27–3.19 (dd, J=15.69, 8.70 Hz, 1H), 2.90–2.83 (dd, J=15.6, 5.49 Hz, 1H), 2.80–2.72 (dd, J=15.6, 8.28 Hz, 1H), 2.34–2.25 (m, 2H), 2.16 (s, 3H), 2.13–2.11 (m, 1H), 2.08–1.82 (m, 4H); $^{13}$C NMR (75 MHz, D$_2$O) δ 175.9, 175.7, 174.5, 172.8, 172.7, 170.9, 164.5, 134.7, 132.5, 130.8, 130.4, 129.7, 127.5, 118.5, 62.2, 61.4, 61.0, 56.7, 53.4, 52.7, 51.8, 50.0, 49.3, 37.4, 31.1, 27.4, 25.6, 22.7; MS m/z (C$_{30}$H$_{41}$N$_9$O$_{10}$S+H)$^+$ 720.

6.31 Example 31

Ac-Pro-His-Ser-HoCys(SOBn)-Asn-NH$_2$
(SEQ ID NO: 17)

10 mg of the compound of Example 11 (14.5 µmole) was dissolved in 1 mL of acetonitrile and 0.5 mL of Milli Q water. 2.5 mg of NaBO$_3$.4H$_2$O was added to the solution at room temperature and it was stirred over night. The reaction mixture was purified according to the procedure of Example 2 to give 3.6 mg (5.11 µmole, 35.2%) of the desired sulfoxide. The NMR data indicated a mixture of two species in a ratio of about 4:1: $^1$H NMR (300 MHz, D$_2$O) δ 8.65 (d, J=6.21 Hz, 1H, minor), 8.62 (d, J=6.21 Hz, 1H, major), 7.52–7.43 (m, 4H), 7.36 (s, 1H, minor), 7.34 (s, 1H, major), 4.95–4.84 (m, 1H), 4.76–4.72 (m, 1H), 4.53–4.49 (m, 1H), 4.43–4.36 (s, 1H), 4.27–4.21 (dd, J=13.2, 5.88 Hz, 1H), 4.00–3.88 (m, 2H), 3.67 (m, 3H), 3.37–3.17 (m, 4H), 2.92–2.74 (m, 2H), 2.33–2.24 (m, 1H), 2.16 (s, 3H), 2.05–1.83 (m, 4H); $^{13}$C NMR (75 MHz, D$_2$O) δ 175.9 (2C), 175.7, 174.5, 172.9, 172.9, 171.8, 134.7, 131.8, 130.4, 130.2, 129.7, 118.6, 118.5, 62.2, 61.4, 57.9, 56.7, 53.4, 51.7, 50.0, 37.5, 31.1, 27.4, 25.6, 22.7; MS m/z (C$_{30}$H$_{41}$N$_9$O$_9$S+H)$^+$ 704.

6.32 Example 32

Ac-Pro-His-Ser-HoCys(SOBn)-Asn-NH$_2$
(SEQ ID NO: 17)

10 mg of the sulfide (14.5 µmole) was dissolved in 2 mL of acetonitrile/water (3:5). Aqueous NaIO$_4$ solution (6.2 mg/100 µL) was added and the mixture was stirred for 24 hours at room temperature. The reaction mixture was concentrated to ca. 1 mL and purified according to the procedure of Example 2 to give 5.7 (8.10 µmole, 55.9%) of the desired sulfoxide. The NMR data indicated a mixture of two species in a ratio of about 6:1: $^1$H NMR (300 MHz, D$_2$O) δ 8.69 (bs, 1H, minor), 8.66 (m, 1H, major), 7.75–7.68 (m, 5H), 7.36 (bs, 1H, minor), 7.34 (bs, 1H, major), 4.86–4.82 (m, 1H), 4.74–4.68 (m, 1H), 4.61–4.46 (m, 2H), 4.36–4.34 (m, 1H), 3.93–3.86 (m, 2H), 3.67 (t, J=6.69 Hz, 2H), 3.38–3.31 (dd, J=15.33, 5.61 Hz, 4H), 3.24–3.13 (m, 3H), 2.91–2.71 (m, 2H), 2.33–2.24 (m, 2H), 2.16 (s, 3H), 2.13–1.83 (m, 5H); $^{13}$C NMR (75 MHz, D$_2$O) δ 175.9, 175.8, 174.4, 172.9, 172.8 (2C), 137.7, 136.1, 134.7, 130.9 (2C), 129.7, 129.0 (2C), 118.4, 62.1, 61.3, 56.8, 53.3, 53.0, 52.6, 51.4, 49.9, 37.4, 31.0, 25.5, 25.4, 22.6; MS m/z (C$_{30}$H$_{41}$N$_9$O$_9$S+H)$^+$ 704.

6.33 Example 33

Ac-PHSC(Bz)N-NH$_2$ (SEQ ID NO: 18)

This compound was prepared from Ac-PHSCN-NH$_2$ (SEQ ID NO: 19) (50 mg, 0.083 mmol) and benzoyl chloride (8.6 µL, 0.075 mmol) according to the method of Examples 2 and 5, except DMF was replaced by acetonitrile and the second equivalent of benzoyl chloride and NMM were added after the first hour. Yield: 18.7 mg (31.7%). $^1$H NMR (300 MHz, D$_2$O) δ 1.81–1.892 (m, 4H), 2.13 (s, 3H), 2.27 (m, 1H), 2.83 (m, 2H), 3.15 (m, 2H), 3.49–3.72 (m, 4H), 3.89 (m, 2H), 4.35 (dd, J=8.5 Hz, J=5.6 Hz, 1H), 4.51 (m, 1H), 7.27 and 7.28 (s, s, 1H), 7.56 (t, J=7.5 Hz, 2H), 7.72 (t, J=7.5 Hz, 1H), 7.99 (d, J=7.5 Hz, 2H), 8.61–8.64 (m, 1H); $^{13}$C NMR (75 MHz, D$_2$O) δ 22.5, 25.4, 27.2, 30.8, 30.9, 37.3, 49.8, 51.4, 53.1, 54.3, 56.7, 61.2, 62.0, 118.3, 128.3 (2C), 129.5, 130.1 (2C), 134.5, 135.6, 137.0, 172.2, 172.6, 172.9, 174.3, 175.5, 175.6, 175.7, 195.5; ES MS m/z (M+H)$^+$ calcd 702, obsd 702. Anal. Calc for C$_{30}$H$_{39}$N$_9$O$_9$S: N, 17.96. Found: N, 12.91 (peptide content: 71.8%).

6.34 Example 34

Ac-PHSC((phenylthio)acetyl)N-NH$_2$
(SEQ ID NO: 20)

This compound was prepared from Ac-PHSCN-NH$_2$ (SEQ ID NO: 19) (25 mg, 0.042 mmol) and (phenylthio)acetyl chloride (12.0 µL, 0.084 mmol) according to the procedure of Examples 2 and 5. Yield: 16.1 mg (51.2%). $^1$H NMR (300

MHz, D$_2$O) δ 1.93 (m, 4H), 2.15 (s, 3H), 2.23 (m, 1H), 2.76 (m, 2H), 3.23–3.48 (m, 4H), 3.65 (m, 2H), 3.86 (m, 2H), 4.03 (s, 2H), 4.42 (m, 2H), 4.57 (m, 1H), 4.70 (m, 1H), 7.28–7.41 (m, 6H), 8.72–9.0 (m, 1H); $^{13}$C NMR (75 MHz, D$_2$O) δ 22.5, 25.8, 27.5, 31.0, 31.2, 37.7, 45.3, 49.8, 51.6, 53.4, 54.7, 57.0, 61.5, 62.6, 118.7, 128.3, 130.4 (2C), 130.5, 130.6 (2C), 134.7, 135.7, 171.7, 172.3, 172.8, 173.4, 175.2 (2C), 175.4, 199.1; ES MS m/z (M+H)$^+$ calcd 748, obsd 748.

6.35 Example 35

Ac-PHSC(Alloc)N-NH$_2$ (SEQ ID NO: 21)

This compound was prepared from Ac-PHSCN-NH$_2$ (SEQ ID NO: 19) (25 mg, 0.042 mmol) and allyl chloroformate (4.2 μL, 0.050 mmol) according to procedure of Examples 2 and 8. Yield: 4.3 mg (15.0%). $^1$H NMR (300 MHz, D$_2$O) δ 1.85–1.93 (m, 4H), 2.16 (s, 3H), 2.28 (m, 1H), 2.82 (m, 2H), 3.21–3.53 (m, 4H), 3.68 (m, 2H), 3.91 (m, 2H), 4.41 (m, 1H), 4.51 (m, 1H), 5.37 (m, 2H), 6.00 (m, 1H), 7.38 and 7.41 (s, s, 1H), 8.68–8.71 (m, 1H); $^{13}$C NMR (75 MHz, D$_2$O) δ 21.4, 24.3, 26.1, 29.8, 31.6, 36.3, 48.7, 50.3, 52.1, 53.2, 55.4, 60.0, 61.0, 68.9, 117.2, 119.2, 128.4, 131.2, 133.5, 170.9, 171.5, 171.64, 171.68, 173.2, 174.4, 174.5; ES MS m/z (M+H)$^+$ calcd 682, obsd 682.

6.36 Example 36

Ac-PHSC(Piv)N-NH$_2$ (SEQ ID NO: 22)

This compound was prepared from Ac-PHSCN-NH$_2$ (SEQ ID NO: 19) (100 mg, 0.167 mmol) and pivaloyl chloride (41.0 μL, 0.334 mmol) according to the procedure of Examples 2 and 5. Yield: 65.7 mg (57.7%). $^1$H NMR (300 MHz, D$_2$O) δ 1.25 (s, 9H), 1.84–2.03 (m, 4H), 2.16 (s, 3H), 2.28 (m, 1H), 2.82 (m, 2H), 3.29 (m, 2H), 3.90 (m, 2H), 3.67 (m, 2H), 3.89 (m, 2H), 4.41 (m, 1H), 4.50 (m, 1H), 4.63 (m, 1H), 4.76 (m, 1H), 4.85 (m, 1H), 7.39 and 7.42 (s, s, 1H), 8.68–8.72 (m, 1H); $^{13}$C NMR (75 MHz, D$_2$O) δ 21.5, 24.4, 26.2, 26.6, 29.3, 29.9, 36.4, 46.5, 48.8, 50.4, 52.2, 53.2, 55.5, 60.2, 61.2, 117.3, 128.6, 133.6, 171.2, 171.6, 171.6, 173.3, 174.5, 174.7, 174.7, 210.8; ES MS m/z (M+H)$^+$ calcd. 682, obsd 682.

6.37 Example 37

Ac-PHSC(cyclohexanoyl)N-NH$_2$ (SEQ ID NO: 23)

This compound was prepared from Ac-PHSCN-NH$_2$ (SEQ ID NO: 19) (100 mg, 0.167 mmol) and cyclohexanoyl chloride (45.0 μL, 0.334 mmol) according to method E-B. Yield: 70.7 mg (59.8%). $^1$H NMR (300 MHz, D$_2$O) δ 1.37 (m, 5H), 1.75–2.04 (m, 9H), 2.16 (s, 3H), 2.31 (m, 1H), 2.66 (m, 1H), 2.84 (m, 2H), 3.25–3.32 (m, 2H), 3.37–3.43 (m, 2H), 3.68 (m, 2H), 3.90 (m, 2H), 4.41 (m, 1H), 4.49 (m, 1H), 4.65 (m, 1H), 7.39 and 7.42 (s, s, 1H), 8.69–8.73 (m, 1H); $^{13}$C NMR (75 MHz, D$_2$O) δ 21.5, 24.4, 25.0, 29.2, 29.4, 29.9, 36.4, 48.8, 50.4, 52.2, 52.4, 53.3, 55.5, 60.2, 61.1, 117.4, 128.6, 133.6, 171.2, 171.4, 171.6, 173.3, 174.5, 174.7, 207.3; ES MS m/z (M+H)$^+$ calcd 708, obsd 708. Anal. Calc for C$_{30}$H$_{45}$N$_9$O$_9$S: N, 17.81. Found: N, 14.14 (peptide content: 79.4%).

6.38 Example 38

Ac-PHSC(nicotinoyl)N-NH$_2$ (SEQ ID NO: 24)

This compound was prepared from Ac-PHSCN-NH$_2$ (SEQ ID NO: 19) (100 mg, 0.167 mmol) and nicotinoyl chloride (59 mg, 0.334 mmol) according to the method of Examples 2 and 5. Yield: 49.5 mg (42.0%). $^1$H NMR (300 MHz, D$_2$O/MeOD) δ 1.80–2.01 (m, 4H), 2.13 (s, 3H), 2.28 (m, 1H), 2.81 (m, 2H), 3.23 (m, 1H), 3.33 (m, 1H), 3.64 (m, 3H), 3.78 (dd, J=15 Hz, J=6 Hz, 1H), 3.89 (m, 2H), 4.39 (m, 1H), 4.48 (m, 1H), 4.74 (m, 1H), 7.36 and 7.39 (s, s, 1H), 8.27 (t, J=6 Hz, 1H), 8.66 and 8.70 (s, s, 1H), 9.07 (m, 2H), 9.36 (s, 1H); $^{13}$C NMR (75 MHz, D$_2$O) δ 21.0, 24.4, 26.0, 29.9, 30.1, 36.4, 48.8, 50.5, 52.2, 52.8, 55.6, 60.3, 61.2, 117.3, 127.9, 128.7, 133.6, 135.0, 140.9, 144.7, 145.2, 170.8, 171.7, 171.7, 173.4, 174.5, 174.6, 174.7, 188.9; ES MS m/z (M+H)$^+$ calcd 703, obsd 703. Anal. Calc for C$_{29}$H$_{38}$N$_{10}$O$_9$S: N, 19.93. Found: N, 13.95 (peptide content: 70.0%).

6.39 Example 39

Ac-PHSC(thiophene-2-carbonyl)N-NH$_2$ (SEQ ID NO: 25)

This compound was prepared from Ac-PHSCN-NH$_2$ (100 mg, 0.167 mmol) and 2-thiophenecarbonyl chloride (36.0 μL, 0.334 mmol) according to the procedure of Examples 2 and 5. Yield: 35.6 mg (30.1%). $^1$H NMR (300 MHz, D$_2$O) δ 1.83–2.04 (m, 4H), 2.14 (s, 3H), 2.28 (m, 1H), 2.83, (m, 2H), 3.13–3.31 (m, 2H), 3.52 (m, 1H), 3.68 (m, 3H), 3.90 (m, 2H), 4.39 (m, 1H), 4.51 (m, 1H), 7.24 (t, J=4.2 Hz, 1H), 7.32 and 7.33 (s, s, 1H), 7.92 (d, J=4.5 Hz, 1H), 7.98 (d, J=3.0 Hz), 8.64 and 8.67 (s, br s, 1H); $^{13}$C NMR (75 MHz, D$_2$O) δ 21.3, 24.2, 26.1, 29.7, 29.8, 36.2, 48.6, 50.2, 52.0, 53.3, 55.5, 60.0, 60.9, 117.2, 128.4, 128.7, 133.1, 133.4, 135.0, 140.1, 171.0, 171.5, 171.7, 173.1, 174.4, 174.5 (2C), 185.9; ES MS m/z (M+H)$^+$ calcd 708, obsd 708. Anal. Calc for C$_{28}$H$_{37}$N$_9$O$_9$S$_2$: N, 17.81. Found: N, 13.66 (peptide content: 76.6%).

6.40 Example 40

Ac-PHSC(allyl)N-NH$_2$ (SEQ ID NO: 26)

This compound was prepared from Ac-PHSCN-NH$_2$ (SEQ ID NO: 19) (25 mg, 0.042 mmol) and allyl bromide (3.6 μL, 0.042 mmol) according to the procedure of Examples 2 and 6, except that the product was prep purified two times. Yield: 11.9 mg (44.5%). 1H NMR (300 MHz, D$_2$O) δ 1.83–2.02 (m, 4H), 2.15 (s, 3H), 2.74–3.00 (m, 4H), 3.23–3.36 (m, 4H), 3.66 (m, 2H), 3.90 (m, 2H), 4.39 (m, 1H), 4.54 (m, 1H), 4.59 (m, 1H), 5.20 (m, 2H), 5.87 (m, 1H), 7.36 and 7.40 (s, s, 1H), 8.66–8.70 (m, 1H); $^{13}$C NMR (75 MHz, D$_2$O/MeOD) δ 22.5, 25.4, 27.2, 30.9, 32.3, 35.3, 37.3, 49.8, 51.4, 53.3, 54.3, 56.5, 61.2, 62.2, 118.4, 119.1, 129.7, 134.6, 134.7, 172.6 (2C), 172.7, 172.8, 174.2, 175.5, 175.7; ES MS m/z (M+H)$^+$ calcd 638, obsd 638. Anal. Calc for C$_{26}$H$_{39}$N$_9$O8S: N, 19.77. Found: N, 14.5 (peptide content: 73.3%).

6.41 Example 41

Ac-PHSC(methoxyethane)N-NH$_2$ (SEQ ID NO: 27)

This compound was prepared from Ac-PHSCN-NH$_2$ (SEQ ID NO: 19) (50 mg, 0.083 mmol) and 2-bromoethyl methyl-ether (8.0 μL, 0.083 mmol) according to the procedure of Examples 2 and 6. Yield: 22.4 mg (41.1%). $^1$H NMR (300 MHz, D$_2$O) δ 1.82–2.03 (m, 4H), 2.14 (s, 3H), 2.25 (m, 1H), 2.78–3.35 (m, 8H), 3.39 (s, 3H), 3.66 (m, 2H), 3.90 (br m, 2H), 4.38 (m, 1H), 4.52 (m, 1H), 4.61 (m, 1H), 4.71 (m, 1H), 7.36 and 7.39 (s, s, 1H), 8.66 and 8.69 (s, s, 1H); $^{13}$C NMR (75 MHz, D$_2$O) δ 22.5, 25.4, 27.2, 31.0, 32.3, 33.7, 37.4, 49.8, 51.4, 53.3, 54.5, 56.6, 59.0, 61.2, 62.2, 71.7, 118.4, 129.7, 134.6, 172.7 (2C), 172.9, 174.4, 175.6, 175.8, 175.9; ES MS m/z (M+H)$^+$ calcd 656, obsd 656. Anal. Calc for $C_{26}H_{41}N_9O_9S$: N, 19.22. Found: N, 13.83 (peptide content: 72.0%).

6.42 Example 42

Ac-PHSC(SMe)N-NH$_2$ (SEQ ID NO: 28)

This compound was prepared from Ac-PHSCN-NH$_2$ (SEQ ID NO: 19) (25 mg, 0.042 mmol) and S-methyl methanethiosulfonate (4.3 µL, 0.042 mmol) according to the procedure of Examples 2 and 7. Yield: 13.8 mg (51.1%). $^1$H NMR (300 MHz, D$_2$O) δ 1.84–2.03 (m, 4H), 2.15 (s, 3H), 2.27 (m, 1H), 2.46 (s, 3H), 2.79–2.86 (m, 2H), 3.07 (m, 1H), 3.24–3.36 (m, 3H), 3.67 (m, 2H), 3.92 (m, 2H), 4.41 (m, 1H), 4.54 (m, 1H), 7.36 and 7.39 (s, s, 1H), 8.67 and 8.70 (s, s, 1H); $^{13}$C NMR (75 MHz, D$_2$O) δ 22.5, 23.1, 25.4, 27.2, 31.0, 37.4, 38.5, 49.8, 51.5, 53.3, 54.0, 56.5, 61.2, 62.2, 118.4, 129.7, 134.6, 172.6, 172.9 (2C), 174.3, 175.5, 175.7 (2C); ES MS m/z (M+H)$^+$ calcd 644, obsd 644. Anal. Calc for $C_{24}H_{37}N_9O_8S_2$: N, 19.58. Found: N, 14.41 (peptide content: 73.6%).

6.43 Example 43

Ac-PHSC(SPh)N-NH$_2$ (SEQ ID NO: 29)

This compound was prepared from Ac-PHSCN-NH$_2$ (SEQ ID NO: 19) (25 mg, 0.042 mmol) and S-phenyl benzenethiosulfonate (10.5 mg, 0.042 mmol) according to the procedure of Examples 2 and 7. Yield: 9.9 mg (33.4%) ~90% pure by $^1$H NMR: $^1$H NMR (300 MHz, D$_2$O) δ 1.83–2.04 (m, 4H), 2.15 (s, 3H), 2.26 (m, 1H), 2.74–2.89 (m, 2H), 3.07–3.42 (m, 4H), 3.66 (m, 2H), 3.88 (m, 2H), 4.39 (m, 1H), 4.41 (m, 1H), 4.73 (m, 1H), 7.35–7.45 (m, 4H), 7.63 (s, 1H), 7.66 (s, 1H), 8.64 and 8.67 (s, s, 1H); $^{13}$C NMR (75 MHz, D$_2$O) δ 22.5, 25.5, 27.3, 31.0, 37.4, 39.8, 49.8, 51.5, 53.3, 54.1, 56.3, 61.2, 62.3, 62.4, 118.4, 129.0, 129.6 (2C), 129.7, 130.6 (2C), 134.6, 137.2, 172.5, 172.61, 172.66, 174.4, 175.6, 175.7, 175.8; ES MS m/z (M+H)$^+$ calcd 708, obsd 708.

6.44 Example 44

Ac-PHSC(SCH$_2$—(R)—CH(NH$_2$)CO$_2$H)N-NH$_2$ (SEQ ID NO: 30)

This compound was prepared from Ac-PHSCN-NH$_2$ (SEQ ID NO: 19) (50 mg, 0.083 mmol) and cysteine methylthiosulfonate (Toronto Research Chemicals) (16.6 mg, 0.083 mmol) according to the procedure of Examples 2 and 7. Yield: 37.2 mg (62.6%). $^1$H NMR (300 MHz, D$_2$O) δ 1.83–2.01 (m, 4H), 2.14 (s, 3H), 2.25 (m, 1H), 2.78–3.35 (m, 8H), 3.65 (m, 2H), 3.91 (m, 2H), 4.38 (m, 1H), 4.48 (m, 1H), 4.52 (m, 1H), 4.73 (m, 1H), 7.35 and 7.38 (s, s, 1H), 8.66 and 8.69 (s, s, 1H); $^{13}$C NMR (75 MHz, D$_2$O) δ 22.5, 25.4, 27.1, 31.0, 37.4, 38.1, 38.9, 49.8, 51.5, 53.0, 53.3, 53.8, 56.6, 61.3, 62.2, 118.4, 129.7, 134.6, 171.7, 172.6, 172.8, 172.9, 174.5, 175.5, 175.7, 175.8; ES MS m/z (M+H)$^+$ calcd 717, obsd 717. Anal. Calc for $C_{26}H_{40}N_{10}O_{10}OS_2$: N, 19.54. Found: N, 11.89 (peptide content: 60.9%).

6.45 Example 45

Ac-PHSHoC(Bz)N-NH$_2$ (SEQ ID NO: 31)

This compound was prepared from crude Ac-PHSHoCN-NH$_2$ (SEQ ID NO: 32) (50 mg, 0.082 mmol) and benzoyl chloride (19.0 µL, 0.163 mmol) according to the procedure of Examples 2 and 5. Yield: 9.8 mg (16.7%). $^1$H NMR (300 MHz, D$_2$O) δ 1.83–2.00 (m, 4H), 2.14 and 2.15 (s, s, 3H), 2.26 (m, 2H), 2.77–2.88 (m, 2H), 3.14–3.31 (m, 4H), 3.64 (m, 2H), 3.93 (m, 2H), 4.38 (m, 1H), 4.53 (m, 2H), 7.31–7.35 (s, 1H), 7.58 (m, 2H), 7.72 (m, 1H), 7.99 (m, 2H), 8.61–8.65 (s, 1H); $^{13}$C NMR (75 MHz, D$_2$O) δ 22.6, 22.7, 26.2 (2C), 27.2, 27.3, 31.1, 31.6, 31.8, 37.6 (2C), 50.0 (2C), 51.5, 51.6, 53.4, 54.1, 54.5, 56.8, 57.0, 61.4 (2C), 62.3, 62.4, 118.4, 128.3, 129.7, 129.8, 130.2, 134.7, 135.6 (2C), 137.6 (2C), 172.8, 172.9, 173.0, 173.1, 174.0, 174.2, 174.5, 174.55, 175.6, 175.7, 175.9, 176.0, 176.2; ES MS m/z (M+H)$^+$ calcd 716, obsd 716. Anal. Calc for $C_{31}H_{41}N_9O_9S$: N, 17.61. Found: N, 11.81 (peptide content: 67.1%).

6.46 Example 46

Ac-PHSHoC(Piv)N—NH$_2$ (SEQ ID NO: 33)

This compound was prepared from crude Ac-PHSHoCN-NH$_2$ (SEQ ID NO: 32) (SAH-15) (50 mg, 0.082 mmol) and pivaloyl chloride (20.0 µL, 0.163 mmol) according to the procedure of Examples 2 and 5. Yield: 12.5 mg (22.2%). $^1$H NMR (300 MHz, D$_2$O) δ 1.25 (s, 9H), 1.83–2.09 (m, 4H), 2.15 (s, 3H), 2.30 (m, 1H), 2.78–2.95 (m, 4H), D$_2$O) (m, 2H), 3.64 (m, 2H), 3.91 (m, 2H), 4.40–4.52 (m, 3H), 7.66 m (m, 1H), 8.66 (m, 1H); $^{13}$C NMR (75 MHz, D$_2$O) δ 22.6, 25.5, 25.55, 27.2, 27.7, 31.0, 31.6, 31.7, 37.4, 37.5, 47.5, 49.9, 51.42, 51.47, 53.3, 54.0, 54.2, 56.6, 56.8, 61.3, 62.25, 62.26, 118.4, 129.7, 134.6, 172.7, 172.9, 173.9, 174.2, 174.4, 175.5, 175.6, 175.85, 175.89, 176.1, 212.8; ES MS m/z (M+H)$^+$ calcd 696, obsd 696. Anal. Calc for $C_{29}H_{45}N_9O_9S$: N, 18.12. Found: N, 13.77 (peptide content: 76.0%).

6.47 Example 47

Ac-PHSHoC(thiophene-2-carbonyl)N-NH$_2$ (SEQ ID NO: 34)

This compound was prepared from crude Ac-PHSHoCN-NH$_2$ (SEQ ID NO: 32) (SAH-15) (50 mg, 0.082 mmol) and 2-thiophenecarbonyl chloride (17.5 µL, 0.163 mmol) according to the procedure of Examples 2 and 5. Yield: 11.4 mg (19.5%). $^1$H NMR (300 MHz, D$_2$O) δ 1.84–2.01 (m, 4H), 2.15 and 2.16 (s, s, 3H), 2.12–2.30 (m, 3H), 2.78–2.89 (m, 2H), 3.20 (m, 3H), 3.66 (m, 2H), 3.93 (m, 2H), 4.56 (m, 1H), 4.79 (m, 2H), 7.27 (m, 1H), 7.34–7.37 (m, 1H), 7.92 (m, 1H), 7.97 (m, 1H), 8.64–8.68 (m, 1H) $^{13}$C NMR (75 MHz, D$_2$O/MeOD) δ 22.5, 25.4, 26.2, 27.1, 27.2, 30.9, 31.7, 31.8, 37.4, 37.5, 49.8, 51.3, 51.4, 53.3, 53.9, 54.2, 54.3, 56.6, 56.9, 61.2, 62.1, 62.2, 64.9, 118.3, 129.7, 129.7, 133.7, 134.5, 135.6, 141.8, 172.6, 172.7, 172.9, 172.94, 173.7, 173.9, 174.2, 175.4, 175.5, 175.6, 175.7, 176.0, 187.9; ES MS m/z (M+H)$^+$ calcd 722, obsd 722. Anal. Calc for $C_{29}H_{39}N_9O_9S_2$: N, 17.46. Found: N, 13.54 (peptide content: 77.6%).

6.48 Example 48

Ac-PHSHoC(methoxyethane)N-NH$_2$ (SEQ ID NO: 35)

This compound was prepared from crude Ac-PHSHoCN-NH$_2$ (SEQ ID NO: 32) (100 mg, 0.163 mmol) and 2-bromoethyl methylether (15.5 µL, 0.163 mmol) according to the procedure of Examples 2 and 6. Yield: 53.3 mg (48.8%). $^1$H NMR (300 MHz, D$_2$O) δ 1.83–2.29 (m, 7H), 2.14 (s, 3H), 2.71–2.88 (m, 6H), 3.23–3.39 (m, 2H), 3.39 (s, 3H), 3.65 (m, 4H), 3.88 (m, 2H), 4.39 (m, 1H), 4.49 (m, 1H), 7.33–7.37(m, 1H), 8.64–8.69 (m, 1H); $^{13}$C NMR (75 MHz, D$_2$O) δ 22.5, 25.4, 27.2, 28.5, 31.0, 31.6, 37.4, 37.5, 49.9, 51.4, 53.3, 53.4, 56.7, 58.9, 61.3, 62.2, 62.3, 71.9, 118.4, 129.6, 129.7, 134.6, 172.7, 172.8, 172.9, 173.0, 174.2, 174.4 (2C), 175.5, 175.6, 175.8, 175.87, 176.1, 176.2; ES MS m/z (M+H)$^+$ calcd 670, obsd 670. Anal. Calc for C$_{27}$H$_{43}$N$_9$O$_9$S: N, 18.82. Found: N, 14.64 (peptide content: 77.8%).

6.49 Example 49

Ac-PHSHoC(Bn)N-NH$_2$ (SEQ ID NO: 36)

This compound was prepared from crude Ac-PHSHoCN-NH$_2$ (SEQ ID NO: 32) (SAH-15) (76.2 mg, 0.124 mmol) and benzyl bromide (14.8 µL, 0.124 mmol) according to the procedure of Examples 2 and 6, except that the reaction mixture was cooled in an ice water bath prior to addition of the BnBr. Yield: 29.4 mg (33.7%). $^1$H NMR (300 MHz, D$_2$O) δ 1.84–2.07 (m, 5H), 2.15 (s, 3H), 2.29 (m, 1H), 2.54–2.90 (m, 4H), 3.23–3.34 (m, 2H), 3.66 (m, 2H), 3.84–3.91 (m, 4H), 4.38–4.48 (m, 3H), 4.73 (m, 1H), 7.34–7.45 (m, 6H), 8.64–8.66 (m, 1H); $^{13}$C NMR (75 MHz, D$_2$O) δ 22.6, 25.4, 27.2 27.9 (2C), 31.0, 31.3, 36.33, 36.36, 37.4, 37.5, 49.8, 51.3, 51.4, 53.3 (2C), 54.0, 54.3, 56.6, 56.7, 61.3, 62.2, 62.3, 118.4, 128.4, 129.6 (2C), 130.00, 130.08, 134.6, 139.6, 172.7, 172.8, 172.9, 174.1, 174.3, 174.4 (2C), 175.5, 175.6, 175.8 (3C), 176.1; ES MS m/z (M+H)$^+$ calcd 702, obsd 702. Anal. Calc for C$_{31}$H$_{43}$N$_9$O$_8$S: N, 17.96. Found: N, 13.07 (peptide content: 72.2%).

6.50 Example 50

Ac-PHSHoC(SMe)N-NH$_2$ (SEQ ID NO: 37)

This compound was prepared from crude Ac-PHSHoCN-NH$_2$ (SEQ ID NO: 32) (50 mg, 0.081 mmol) and S-methyl methanethiosulfonate (8.4 µL, 0.081 mmol) according to the procedure of Examples 2 and 7. Yield: 24.6 mg (46.2%). 1H NMR (300 MHz, D$_2$O) δ 1.84–2.33 (m, 7H), 2.15 (s, 3H), 2.46 (s, 3H), 2.72–2.95 (m, 4H), 3.19–3.41 (m, 2H), 3.67 (m, 2H), 3.91 (m, 2H), 4.39 (m, 1H), 4.48–4.58 (m, 2H), 4.73 (m, 1H), 7.35–7.59 (m, 1H), 8.66–8.70 (m, 1H); $^{13}$C NMR (75 MHz, D$_2$O) δ 22.6, 23.3, 25.5, 27.2, 31.0, 31.1, 33.9, 34.0, 37.4, 37.5, 49.9, 51.42, 51.47, 53.3, 53.4, 53.7, 24.0, 56.71, 56.78, 61.3, 62.1, 62.2, 118.4, 129.6, 134.6, 172.7, 172.8, 172.9, 173.0, 174.1, 174.4, 175.5, 175.6, 175.83, 175.88, 176.2; ES MS m/z (M+H)$^+$ calcd 658, obsd 658. Anal. Calc for C$_{25}$H$_{39}$N$_9$O$_8$S$_2$: N, 19.16. Found: N, 14.48 (peptide content: 75.6%).

6.51 Example 51

Ac-PHSHoC(SPh)N—NH$_2$ (SEQ ID NO: 38)

This compound was prepared from crude Ac-PHSHoCN-NH$_2$ (SEQ ID NO: 32(SAH-15) (50 mg, 0.081 mmol) and S-phenyl benzenethiosulfonate (20.5 mg, 0.081 mmol) according to the procedure of Examples 2 and 7. Yield: 20.8 mg (35.6%). $^1$H NMR (300 MHz, D$_2$O) δ 1.83–2.31 (m, 7H), 2.14 (s, 3H), 2.66–2.93 (m, 4H), 3.15–3.35 (m, 2H), 3.65 (m, 2H), 3.85 (m, 2H), 4.36–4.52 (m, 3H), 7.32–7.47 (m, 4H), 7.62 (m, 1H), 8.64 and 8.67 (s, s, 1H); $^{13}$C NMR (75 MHz, D$_2$O) δ 22.6, 25.5, 27.2, 30.9, 31.0, 35.1, 35.3, 37.4, 37.5, 49.8, 51.3, 51.4, 53.3, 53.6, 53.9, 56.6, 56.8, 61.3, 62.23, 62.27, 118.3, 128.7, 129.33, 129.39, 129.6, 130.6, 130.61, 134.6, 137.7, 137.8, 172.7 (2C), 172.8, 173.9, 174.1, 174.42, 174.44, 175.5, 175.6, 175.7, 175.85, 175.88, 176.1; ES MS m/z (M+H)$^+$ calcd 720, obsd 720. Anal. Calc for C$_{30}$H$_{41}$N$_9$O$_8$S$_2$: N, 17.51. Found: N, 12.93 (peptide content: 73.9%).

6.52 Example 52

Fmoc-S-benzyl-L-cysteine sulfone-OH

S-benzyl-L-cysteine sulfone (Toronto Research Chemicals) (1.0 g, 4.11 mmol) was dissolved in 1,4-dioxane (3.0 mL) and 10% Na$_2$CO$_3$ (4.3 mL, 4.11 mmol). To this solution was added Fmoc-OSu (1.3 g, 3.90 mmol) dissolved in 5.0 mL 1,4-dioxane, via addition funnel. The reaction mixture was a thick white slurry. After 3 h of stirring, 1 N HCl was added until pH was about 3.0. The solids were not filterable, so ethyl acetate was added and the layers were shaken in a separatory funnel. The top, organic layer was decanted from the bottom precipitate. The organics were concentrated under reduced pressure to a solid of reasonable purity, by NMR, for use in the subsequent coupling. $^1$H NMR (300 MHz, DMSO-d6) δ 3.45 (dd, J=9.33 Hz, J=14.55 Hz, 1H), 3.59 (dd, J=3.0 Hz, J=14.5 Hz, 1H), 4.23–4.33 (m, 3H), 4.50 (m, 3H), 7.30 (q, J=8.97 Hz, J=16.3 Hz, 4H), 7.38 (br s, 5H), 7.69 (d, J=7.39 Hz, 2H), 7.86 (d, J=7.35 Hz, 2H); ES MS m/z (M+Na)$^+$ calcd 488, obsd 488.

6.53 Example 53

Ac-PHSA(β-SO$_2$Bn)N-NH$_2$ (SEQ ID NO: 39)

This compound was prepared from 200 mg (0.63 mmol/g) Fmoc-Asn(trt)-Rink, according to the procedure of Examples 2 and 9, except that it was prep purified twice. Fmoc-Ala(β-SO$_2$Bn)-OH (SAH-13) was coupled directly to the Asn. Yield: 22.9 mg (25.2%). $^1$H NMR (300 MHz, D$_2$O) δ 1.83–2.01 (m, 3H), 2.15 (s, 1H), 2.27 (m, 1H), 2.79–2.90 (m, 2H), 3.19–3.37 (m, 2H), 3.63–3.75 (m, 3H), 3.89–3.96 (m, 3H), 4.39 (m, 1H), 4.52 (m, 1H), 4.66 (s, 2H), 5.10 (m, 1H), 7.34 and 7.37 (s, s, 1H), 7.51 (br s, 5H), 8.62–8.66 (m, 1H); $^{13}$C NMR (75 MHz, D$_2$O) δ 22.7, 25.5, 27.3, 31.1, 37.4, 49.3, 50.0, 51.8, 52.7, 53.3, 56.7, 60.9, 61.4, 62.2, 118.5, 127.5, 129.7, 130.4, 130.7, 132.5, 134.7, 170.9, 172.7, 172.8, 173.0, 174.5, 175.7, 175.9; ES MS m/z (M+H)$^+$ calcd 721, obsd 721. Anal. Calc for C$_{30}$H$_{41}$N$_9$O$_{10}$S: N, 19.17. Found: N, 12.70 (peptide content: 66.3%).

6.54 Example 54

Ac-PHSHoCN-NH$_2$ (SEQ ID NO: 32)

This compound was prepared from 2.0 g (0.63 mmol/g) Fmoc-Asn(trt)-Rink, according to the procedure of Examples 2 and 9, to afford 764.5 mg (79.3%) of crude material. Fmoc-HoC(trt)-OH (Chem-Impex) was coupled to the Asn. The peptide was >90% of a 1:1 mixture of peaks, separated by 0.1 min, by analytical HPLC. It is assumed that the two peaks are conformational isomers. The crude material was used in the analog syntheses. ES MS m/z (M+H)$^+$ calcd 612, obsd 612.

6.55 Example 55

2-tert-Butoxycarbonylamino-4-phenylsulfanyl-butyric acid allyl ester

A round bottom flask was charged with nitrogen and NaSPh (61.5 mg, 0.465 mmol) and DMF (1 mL) were added.

The mixture was cooled in an ice water bath and 4-bromo-2-tert-Butoxycarbonylamino butyric acid allyl ester (100 mg, 0.310 mmol) dissolved in DMF (1 mL) was added. The mixture was transferred to a 0–5° C. refrigerator where it sat overnight. The next morning (16 h), the solution was concentrated in vacuo and the residue was diluted with EtOAc and water. The layers were separated and the organic layer was washed with water, 0.1 M KHSO$_4$ and brine and was dried over Na$_2$SO$_4$. Ethyl acetate was removed to afford an oil: 95.7 mg (87.8%). This compound was used without further purification. $^1$H NMR (300 MHz, CDCl$_3$) δ 1.51 (s, 9H), 2.02 (m, 1H), 2.24 (m, 1H), 3.0 (m, 2H), 4.50 (br s, 1H), 4.67 (t, J=1.29 Hz, 1H), 4.69 (t, J=1.29 Hz, 1H), 5.20 (br s, 1H), 5.34 (m, 2H), 5.93 (m, 1H), 7.25–7.41 (m, 5H); $^{13}$C NMR (75 MHz, CDCl$_3$) δ 22.2, 29.5, 31.0, 33.7, 61.6, 67.2, 120.2, 127.5, 129.2, 130.2, 130.6, 130.9, 132.6, 156.5, 173.0.

6.56 Example 56

2-(9H-Fluoren-9-ylmethoxycarbonylamino)-4-phenylsulfanyl-butyric acid

The TFA salt of (L)-4-phenylsulfanyl-butyric acid (156.6 mg, 0.481 mmol) was dissolved in water (1.0 mL). Na$_2$CO$_3$ (102 mg, 0.962 mmol) was added and a precipitate instantly formed. FmocOSu (162.2 mg, 0.481 mmol) dissolved in dioxane (2.0 mL) was added to the amino acid. An additional 2.0 mL of water was added to dilute the thick slurry. After 1 h, an additional 0.1 eq. of FmocOSu (16.2 mg, 0.0481 mmol) in dioxane (0.5 mL) was added. After 1.5 h, the reaction was diluted with ethyl acetate and washed with 1 N HCl and brine. The organic layer was concentrated to a residue and chromatographed (6.0 g SiO2, 10% MeOH/CH$_2$Cl$_2$) to afford a light yellow solid: 164.4 mg (78.8%). The material was ~90% pure by NMR: $^1$H NMR (300 MHz, CDCl$_3$/MeOD) δ 1.95 (m, 1H), 2.14 (m, 1H), 2.83 (m, 1H), 4.17 (br t, J=6.78 Hz, 1H), 4.36 (m, 3H), 7.13–7.72 (m, 13H).

6.57 Example 57

Ac-PHSHoC(Ph)N-NH$_2$ (SEQ ID NO: 40)

This compound was prepared from Fmoc-Asn(trt)-Rink (215 mg, 0.63 mmol/g), according to procedure of Examples 2 and 9, where the compound of Example 55 was coupled to Asn. Yield: 29.4 mg (33.7%). $^1$H NMR (300 MHz, D$_2$O) δ 1.83–2.32 (m, 6H), 2.14 (s, 3H), 2.71–2.90 (m, 2H), 3.02–3.37 (m, 4H), 3.65 (m, 2H), 3.90 (m, 2H), 4.36 (m, 1H), 4.48 (m, 1H), 4.61 (m, 1H), 4.73 (m, 1H), 7.29–7.48 (m, 6H), 8.64–8.67 (m, 1H); $^{13}$C NMR (75 MHz, D$_2$O) δ 22.6, 25.4, 27.2, 30.2, 31.0, 31.3, 37.4, 49.8, 51.4, 53.4, 53.9, 56.6, 61.3, 62.1, 118.3, 127.9, 129.6, 130.5, 130.59, 134.6, 135.7, 172.7, 172.9, 174.0, 174.4, 175.6, 175.8; ES MS m/z (M+H)$^+$ calcd 688, obsd 688. Anal. Calc for C$_{30}$H$_{41}$N$_9$O$_8$S: N, 18.33. Found: N, 13.30 (peptide content: 72.5%).

6.58 Example 58

Ac-Pro-His-Ser-Cys(β,β-dimethyl)-Asn-NH$_2$ (SEQ ID NO: 1)

This compound was prepared from Rink amide AM resin (0.550 mg, loading of 0.74 mmol/g, 0.407 mmol) according to procedures of Examples 1 and 2, but using the following number of equivalents in the double couplings: 2 equivalents of amino acid, 2 equivalents of HBTU, 2 equivalents of HOBt and 4 equivalents of NMM. PLG-94 (108 mg, 43%) was isolated as a white, fluffy solid, and as a mixture of two compounds in a ratio of 84:16: $^1$H NMR (300 MHz, DMSO-d6) δ 8.98–8.96 (m, 1H), 8.46–8.19 (m, 2H), 8.14–7.93 (m, 2H), 7.39–7.34 (m, 2H), 7.07 (s, 2H), 6.92 (s, 1H), 4.78–4.25 (m, 4H), 3.23–3.12 (m, 1H), 3.05–2.93 (m, 2H), 2.58–2.38 (m, 2H, overlapping with DMSO peak), 2.07–1.97 (m, 3H), 1.90–1.62 (m, 3H), 1.37 (s, 3H), 1.32 (s, 3H); ES MS m/z (M+H)$^+$ 626.6; Anal. calcd for C$_{25}$H$_{39}$N$_9$O$_8$S: N, 20.15. Found: 14.84 (peptide content, 74%).

6.59 Example 59

Effect of Peptides on Invasion In vitro

Peptides were tested for their ability to inhibit FGF-2 mediated angiogenesis in vivo in a Matrigel® Plug Model. Test native or derivatized peptides were added at a concentration of 1 μM into Matrigel plugs. The results are shown in the table below.

| Compound | % inhibition (± StdDev). |
|---|---|
| PHSSN | 20.8 ± 34.1 |
| PHSSN | 47.5 ± 13.6 |
| 15 | 71.7 ± 41.9 |
| 6 | 74.9 ± 5.8 |
| 3 | 25.3 ± 8.6 |
| 4 | 75.8 ± 38.3 |
| 16 | 72.0 ± 31.9 |
| 13 | 81.0 ± 50.0 |
| 14 | 73.3 ± 34.5 |
| 7 | 56.6 ± 22.4 |
| 1 | 88.2 ± 42.9 |

6.60 Example 60

Localization of Ac-PFSCNGGK(biotin)-NH$_2$

Mice were inoculated with 1×10$^6$ Lewis Lung carcinoma (3LL) cells in Matigel™, two per mouse. After 5 days, the mice were injected via the tail vein with either 50 μg of Ac-PFSCNGGK(biotin)-NH$_2$ (SEQ ID NO: 42) or PFSCN. (SEQ ID NO: 43) After two hours to clear non-bound peptide, the animals were sacrificed and the plugs and different organs were removed and placed in zinc fixative for 24 hours and 4 mm paraffin-embedded sections prepared. In some experiments, the animals were sacrificed after fours post-injection. Slides were deparaffinized in xylene, rehydrated and blocked in 1% BSA for 30 minutes. The slides were then incubated with a rat monoclonal antibody against CD31 (BD Biosciences) at a 1:50 dilution in PBS and an anti-biotin mouse monoclonal Cy3 conjugated antibody (Sigma) at a 1:500 dilution. In other experiments, anti-biotin goat polyclonal FITC conjugated antibody (Sigma) was used. The samples were incubated with a secondary antibody: anti-rat IgG FITC conjugated antibody (BD Biosciences) at 1:500 dilution in PBS and DAPI (300 nM) for 2 hours. Ac-PFSCNGGK(biotin)-NH$_2$ (SEQ ID NO: 42) at 40 μM in PBS was incubated with a 1:500 dilution of an anti-biotin goat polyclonal FITC conjugated antibody (Sigma) for 30 minutes on ice. The mixture is added to B16 melanoma cells that had previously been plated on cover slips in a 6-well plate and incubate on ice for four hours. The, cells were fixed and observed under the microscope, which demonstrated that Ac-PFSCNGGK(biotin)-NH$_2$ (SEQ ID NO: 42) localized to CD31 positive neovessels within the tumor and not with other cells and also showed that Ac-PFSCNGGK(biotin)-NH$_2$ (SEQ ID NO: 42) remains associated to tumor endothelium four hours after injection.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All publications and patents cited herein are incorporated by reference.

What is claimed is:

1. A compound of structural Formula (I):

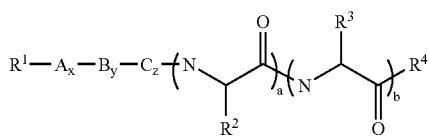

or a pharmaceutically available salt, solvate or hydrate thereof wherein:
  a, b, x, y and z are 1;
  A is proline;
  B is histidine;
  C is serine;
  $R^1$ is $C(O)CH_3$;
  $R^2$ is $—(CH_2)_m S(O)_n R^5$;
  m is 1;
  n is 0;
  $R^3$ is $—CH_2 CONH_2$;
  $R^4$ is $NH_2$;
  $R^5$ is methyl
(SEQ ID NO: 44).

2. A compound of structural Formula (I):

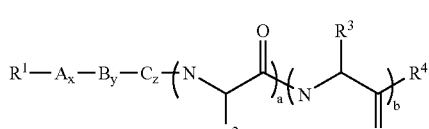

or a pharmaceutically available salt, solvate or hydrate thereof wherein:
  a, b, x, y and z are 1;
  A is proline;
  B is histidine;
  C is serine;
  $R^1$ is $C(O)CH_3$;
  $R^2$ is $—(CH_2)_m S(O)_n R^5$;
  m is 1;
  n is 0;
  $R^3$ is $—CH_2 CONH_2$;
  $R^4$ is $NH_2$;
  $R^5$ is acetyl;
(SEQ ID NO: 45).

3. A pharmaceutical composition comprising a compound of structural Formula (I):

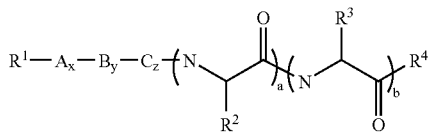

or a pharmaceutically available salt, solvate or hydrate thereof wherein:
  a, b, x, y and z are 1;
  A is proline;
  B is histidine;
  C is serine;
  $R^1$ is $—C(O)CH_3$;
  $R^2$ is $—(CH_2)_m S(O)_n R^5$;
  m is 1;
  n is 0 ;
  $R^3$ is $—CH_2 CONH_2$;
  $R^4$ is $NH_2$;
  $R^5$ is methyl
(SEQ ID NO: 44);
and a pharmaceitically acceptable vehicle.

4. A pharmaceutical composition comprising a compound of structural Formula (I):

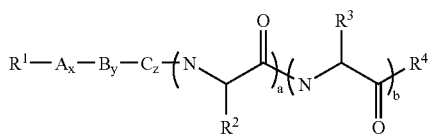

or a pharmaceutically available salt, solvate or hydrate thereof wherein:
  a, b, x, y and z are 1;
  A is proline;
  B is histidine;
  C is serine;
  $R^1$ is $—C(O)CH_3$;
  $R^2$ is $—(CH_2)_m S(O)_n R^5$;
  m is 1;
  n is 0 ;
  $R^3$ is $—CH_2 CONH_2$;
  $R^4$ is $NH_2$;
  $R^5$ is acetyl
(SEQ ID NO: 45);
and a pharmaceutically acceptable vehicle.

5. A method for treating lung cancer in a patient comprising administering to a patient having lung cancer a therapeutically effective amount of a compound of structural Formula (I):

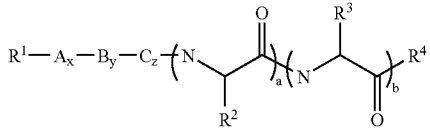

or a pharmaceutically available salt, solvate or hydrate thereof wherein:
a, b, x, y and z are 1;
A is proline;
B is histidine;
C is serine;
$R^1$ is —C(O)CH$_3$;
$R^2$ is —(CH$_2$)$_m$S(O)$_n$R$^5$;
m is 1;
n is 0;
$R^3$ is —CH$_2$ CONH$_2$;
$R^4$ is NH$_2$;
$R^5$ is methyl
(SEQ ID NO: 44).

6. A method for treating lung cancer in a patient comprising administering to a patient having lung cancer a therapeutically effective amount of a compound of structural Formula (I):

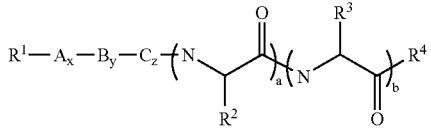

or a pharmaceutically available salt, solvate or hydrate thereof wherein:
a, b, x, y and z are 1;
A is proline;
B is histidine;
C is serine;
$R^1$ is —C(O)CH$_3$;
$R^2$ is —(CH$_2$)$_m$S(O)$_n$R$^5$;
m is 1;
n is 0;
$R^3$ is —CH$_2$ CONH$_2$;
$R^4$ is NH$_2$;
$R^5$ is acetyl
(SEQ ID NO: 45).

7. A method for treating lung cancer in a patient comprising administering to a patient having lung cancer a therapeutically effective amount of a pharmaceutical composition comprising a) a compound of structural Formula (I):

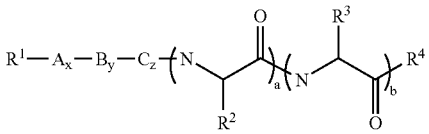

or a pharmaceutically available salt, solvate or hydrate thereof wherein:
a, b, x, y and z are 1;
A is proline;
B is histidine;
C is serine;
$R^1$ is —C(O)CH$_3$;
$R^2$ is —(CH$_2$)$_m$S(O)$_n$R$^5$;
m is 1;
n is 0;
$R^3$ is —CH$_2$ CONH$_2$;
$R^4$ is NH$_2$;
$R^5$ is methyl
(SEQ ID NO: 44); and
b) a pharmaceutically acceptable vehicle.

8. A method for treating lung cancer in a patient comprising administering to a patient having lung cancer a therapeutically effective amount of a pharmaceutical composition comprising a) a compound of structural Formula (I):

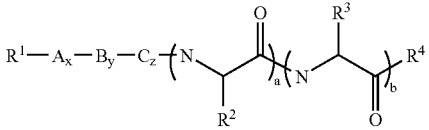

or a pharmaceutically available salt, solvate or hydrate thereof wherein:
a, b, x, y and z are 1;
A is proline;
B is histidine;
C is serine;
$R^1$ is —C(O)CH$_3$;
$R^2$ is —(CH$_2$)$_m$S(O)$_n$R$^5$;
m is 1;
n is 0;
$R^3$ is —CH$_2$ CONH$_2$;
$R^4$ is NH$_2$;
$R^5$ is acetyl
(SEQ ID NO: 45); and
b) a pharmaceutically acceptable vehicle.

9. The method of any one of claims 5-8 wherein the patient is a human.

* * * * *

```
                        SEQUENCE LISTING

<160> NUMBER OF SEQ ID NOS: 50

<210> SEQ ID NO 1
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(beta,beta-dimethyl)

<400> SEQUENCE: 1

Pro His Ser Xaa Asn
1               5

<210> SEQ ID NO 2
<211> LENGTH: 5
<212> TYPE: PRT
<213> ORGANISM: Artificial Sequence
<220> FEATURE:
<223> OTHER INFORMATION: synthesized peptide

<400> SEQUENCE: 2

Pro His Ser Cys Asn
1               5

<210> SEQ ID NO 3
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(benzyl)

<400> SEQUENCE: 3

Pro His Ser Xaa Asn
1               5

<210> SEQ ID NO 4
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
```

```
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(4-methyl-benzyl)

<400> SEQUENCE: 4

Pro His Ser Xaa Asn
1               5

<210> SEQ ID NO 5
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Met(O)

<400> SEQUENCE: 5

Pro His Ser Xaa Asn
1               5

<210> SEQ ID NO 6
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Met(O2)

<400> SEQUENCE: 6

Pro His Ser Xaa Asn
1               5

<210> SEQ ID NO 7
<211> LENGTH: 4
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 4
<220> FEATURE:
<221> NAME/KEY: VARIANT
<222> LOCATION: 4
<223> OTHER INFORMATION: Xaa = Cys(methyl)

<400> SEQUENCE: 7
```

Pro His Ser Xaa
1

<210> SEQ ID NO 8
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(4-MeO-Phenyl)

<400> SEQUENCE: 8

Pro His Ser Xaa Asn
1               5

<210> SEQ ID NO 9
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(parra-MeOBzl)

<400> SEQUENCE: 9

Pro His Ser Xaa Asn
1               5

<210> SEQ ID NO 10
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(Ph)

<400> SEQUENCE: 10

Pro His Ser Xaa Asn
1               5

<210> SEQ ID NO 11
<211> LENGTH: 5
<212> TYPE: PRT
<213> ORGANISM: Artificial Sequence
<220> FEATURE:

```
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(S-tBu)

<400> SEQUENCE: 11

Pro His Ser Xaa Asn
1               5

<210> SEQ ID NO 12
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(tBu)

<400> SEQUENCE: 12

Pro His Ser Xaa Asn
1               5

<210> SEQ ID NO 13
<211> LENGTH: 4
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 4
<220> FEATURE:
<221> NAME/KEY: VARIANT
<222> LOCATION: 3
<223> OTHER INFORMATION: Xaa = Cys(SMe)

<400> SEQUENCE: 13

His His Xaa Asn
1

<210> SEQ ID NO 14
<211> LENGTH: 4
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 4
<220> FEATURE:
<221> NAME/KEY: VARIANT
<222> LOCATION: 3
```

```
<223> OTHER INFORMATION: Xaa = Cys(SMe)

<400> SEQUENCE: 14

His Ser Xaa Asn
1

<210> SEQ ID NO 15
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(SO2Bn)

<400> SEQUENCE: 15

Pro His Ser Xaa Asn
1               5

<210> SEQ ID NO 16
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = HoCys(SO2Ph)

<400> SEQUENCE: 16

Pro His Ser Xaa Asn
1               5

<210> SEQ ID NO 17
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = HoCys(SOBn)

<400> SEQUENCE: 17

Pro His Ser Xaa Asn
1               5

<210> SEQ ID NO 18
<211> LENGTH: 5
```

```
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(Bz)

<400> SEQUENCE: 18

Pro His Ser Xaa Asn
1               5

<210> SEQ ID NO 19
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5

<400> SEQUENCE: 19

Pro His Ser Cys Asn
1               5

<210> SEQ ID NO 20
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys((phenylthio)acetyl)

<400> SEQUENCE: 20

Pro His Ser Xaa Asn
1               5

<210> SEQ ID NO 21
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(Alloc)
```

```
<400> SEQUENCE: 21

Pro His Ser Xaa Asn
1               5

<210> SEQ ID NO 22
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(Piv)

<400> SEQUENCE: 22

Pro His Ser Xaa Asn
1               5

<210> SEQ ID NO 23
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(cyclohexanoyl)

<400> SEQUENCE: 23

Pro His Ser Xaa Asn
1               5

<210> SEQ ID NO 24
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(nicotinoyl)

<400> SEQUENCE: 24

Pro His Ser Xaa Asn
1               5

<210> SEQ ID NO 25
<211> LENGTH: 5
<212> TYPE: PRT
```

```
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(thiophene-2-carbonyl)

<400> SEQUENCE: 25

Pro His Ser Xaa Asn
1               5

<210> SEQ ID NO 26
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(allyl)

<400> SEQUENCE: 26

Pro His Ser Xaa Asn
1               5

<210> SEQ ID NO 27
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(methoxyethane)

<400> SEQUENCE: 27

Pro His Ser Xaa Asn
1               5

<210> SEQ ID NO 28
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
```

```
<221> NAME/KEY: VARIANT
<222> LOCATION: 4
<223> OTHER INFORMATION: Xaa = Cys(SMe)

<400> SEQUENCE: 28

Pro His Ser Xaa Asn
1               5

<210> SEQ ID NO 29
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(SPh)

<400> SEQUENCE: 29

Pro His Ser Xaa Asn
1               5

<210> SEQ ID NO 30
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(SCH2-(R)-CH(NH2)CO2H)

<400> SEQUENCE: 30

Pro His Ser Xaa Asn
1               5

<210> SEQ ID NO 31
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = HoCys(Bz)

<400> SEQUENCE: 31

Pro His Ser Xaa Asn
1               5
```

```
<210> SEQ ID NO 32
<211> LENGTH: 8
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 8
<220> FEATURE:
<221> NAME/KEY: VARIANT
<222> LOCATION: 8
<223> OTHER INFORMATION: Xaa = Lys(biotin)

<400> SEQUENCE: 32

Pro Phe Ser Cys Asn Gly Gly Xaa
1               5

<210> SEQ ID NO 33
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = HoCys(Piv)

<400> SEQUENCE: 33

Pro His Ser Xaa Asn
1               5

<210> SEQ ID NO 34
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = HoCys(thiophene-2-carbonyl)

<400> SEQUENCE: 34

Pro His Ser Xaa Asn
1               5

<210> SEQ ID NO 35
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
```

```
<221> NAME/KEY: AMIDATION
<222> LOCATION: 5
<220> FEATURE:
<221> NAME/KEY: VARIANT
<222> LOCATION: 4
<223> OTHER INFORMATION: Xaa = HoCys(methoxyethane)

<400> SEQUENCE: 35

Pro His Ser Xaa Asn
1               5

<210> SEQ ID NO 36
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = HoCys(Bn)

<400> SEQUENCE: 36

Pro His Ser Xaa Asn
1               5

<210> SEQ ID NO 37
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = HoCys(SMe)

<400> SEQUENCE: 37

Pro His Ser Xaa Asn
1               5

<210> SEQ ID NO 38
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = HoCys(SPh)

<400> SEQUENCE: 38

Pro His Ser Xaa Asn
```

```
<210> SEQ ID NO 39
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Ala(beta-SO2Bn)

<400> SEQUENCE: 39

Pro His Ser Xaa Asn
1               5

<210> SEQ ID NO 40
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = HoCys(Ph)

<400> SEQUENCE: 40

Pro His Ser Xaa Asn
1               5

<210> SEQ ID NO 41
<211> LENGTH: 5
<212> TYPE: PRT
<213> ORGANISM: Artificial Sequence
<220> FEATURE:
<223> OTHER INFORMATION: synthesized peptide

<400> SEQUENCE: 41

Pro His Ser Ser Asn
1               5

<210> SEQ ID NO 42
<211> LENGTH: 8
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 8
<220> FEATURE:
<221> NAME/KEY: VARIANT
<222> LOCATION: 8
<223> OTHER INFORMATION: Xaa = Lys(biotin)
```

```
<400> SEQUENCE: 42

Pro Phe Ser Cys Asn Gly Gly Xaa
1               5

<210> SEQ ID NO 43
<211> LENGTH: 5
<212> TYPE: PRT
<213> ORGANISM: Artificial Sequence
<220> FEATURE:
<223> OTHER INFORMATION: synthesized peptide

<400> SEQUENCE: 43

Pro Phe Ser Cys Asn
1               5

<210> SEQ ID NO 44
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(Me)

<400> SEQUENCE: 44

Pro His Ser Xaa Asn
1               5

<210> SEQ ID NO 45
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
<222> LOCATION: 4
<223> OTHER INFORMATION: Xaa = Cys(acetyl)

<400> SEQUENCE: 45

Pro His Ser Xaa Asn
1               5

<210> SEQ ID NO 46
<211> LENGTH: 5
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5
<220> FEATURE:
<221> NAME/KEY: VARIANT
```

```
<222> LOCATION: 4
<223> OTHER INFORMATION: Xaa = Cys(acetamidomethyl)

<400> SEQUENCE: 46

Pro His Ser Xaa Asn
1               5

<210> SEQ ID NO 47
<211> LENGTH: 4
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 4
<220> FEATURE:
<221> NAME/KEY: VARIANT
<222> LOCATION: 3
<223> OTHER INFORMATION: Xaa = Cys(Me)

<400> SEQUENCE: 47

Pro Ser Xaa Asn
1

<210> SEQ ID NO 48
<211> LENGTH: 4
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 4
<220> FEATURE:
<221> NAME/KEY: VARIANT
<222> LOCATION: 3
<223> OTHER INFORMATION: X = Cys(ethyl)

<400> SEQUENCE: 48

Pro Ser Xaa Asn
1

<210> SEQ ID NO 49
<211> LENGTH: 4
<212> TYPE: PRT
<213> ORGANISM: Artificial Sequence
<220> FEATURE:
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 4

<400> SEQUENCE: 49

Pro His Ser Ala
1

<210> SEQ ID NO 50
<211> LENGTH: 5
<212> TYPE: PRT
<213> ORGANISM: Artificial Sequence
<220> FEATURE:
```

```
-continued
<223> OTHER INFORMATION: synthesized peptide
<220> FEATURE:
<221> NAME/KEY: ACETYLATION
<222> LOCATION: 1
<220> FEATURE:
<221> NAME/KEY: AMIDATION
<222> LOCATION: 5

<400> SEQUENCE: 50

Pro His Ser Met Asn
1               5
```